United States Patent
Giftakis et al.

(10) Patent No.: US 11,077,305 B2
(45) Date of Patent: Aug. 3, 2021

(54) IDENTIFICATION OF COMPROMISED COMPONENTS IN A MEDICAL SYSTEM

(71) Applicant: MEDTRONIC, INC., Minneapolis, MN (US)

(72) Inventors: Jonathon E. Giftakis, Maple Grove, MN (US); Timothy J. Denison, Minneapolis, MN (US); Paul H. Stypulkowski, North Oaks, MN (US); Scott R. Stanslaski, Shoreview, MN (US); Robert S. Raike, Minneapolis, MN (US); Mae Eng, Shoreview, MN (US); David E. Linde, Corcoran, MN (US); Thomas Adamski, Andover, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 663 days.

(21) Appl. No.: 15/699,873

(22) Filed: Sep. 8, 2017

(65) Prior Publication Data

US 2018/0071530 A1 Mar. 15, 2018

Related U.S. Application Data

(60) Provisional application No. 62/393,268, filed on Sep. 12, 2016.

(51) Int. Cl.
*A61N 1/36* (2006.01)
*A61N 1/05* (2006.01)
*A61N 1/08* (2006.01)

(52) U.S. Cl.
CPC ....... *A61N 1/3614* (2017.08); *A61N 1/36142* (2013.01); *A61N 1/0531* (2013.01);
(Continued)

(58) Field of Classification Search
CPC ................ A61N 1/0531; A61N 1/0534; A61N 1/36082; A61N 1/3614; A61N 1/36142; A61N 1/36185; A61N 2001/083
See application file for complete search history.

(56) References Cited

U.S. PATENT DOCUMENTS

| | | | |
|---|---|---|---|
| 6,920,359 B2 | 7/2005 | Meadows et al. | |
| 7,574,259 B1 * | 8/2009 | Pei | A61N 1/056 607/28 |

(Continued)

OTHER PUBLICATIONS

Gunderson: "An Algorithm to Predict Implantable Cardioverter-Defibrillator Lead Failure", JACC vol. 44, No. 9, Nov. 2, 2004:1898-902.

(Continued)

*Primary Examiner* — Amanda K Hulbert
(74) *Attorney, Agent, or Firm* — Withers & Keys, LLC

(57) ABSTRACT

In some examples of selecting a target therapy delivery site for treating a patient condition, a relatively high frequency electrical stimulation signal is delivered to at least two areas within a first region (e.g., an anterior nucleus of the thalamus) of a brain of a patient, and changes in brain activity (e.g., as indicated by bioelectrical brain signals) within a second region (e.g., a hippocampus) of the brain of the patient in response to the delivered stimulation are determined. The target therapy delivery site, an electrode combination, or both, may be selected based on the changes in brain activity.

31 Claims, 19 Drawing Sheets

(52) U.S. Cl.
CPC ........ *A61N 1/0534* (2013.01); *A61N 1/36082* (2013.01); *A61N 1/36185* (2013.01); *A61N 2001/083* (2013.01)

(56) References Cited

U.S. PATENT DOCUMENTS

| | | |
|---|---|---|
| 7,792,590 B1 | 9/2010 | Pianca et al. |
| 8,260,425 B2 | 9/2012 | Kokones et al. |
| 8,463,384 B2 | 6/2013 | Germanson et al. |
| 8,543,211 B2 | 9/2013 | Simon |
| 8,560,041 B2 * | 10/2013 | Flaherty ............... A61B 5/0031 600/373 |
| 8,676,342 B2 | 3/2014 | Kokones et al. |
| 8,751,000 B2 | 6/2014 | Miller et al. |
| 8,774,923 B2 | 7/2014 | Rom |
| 8,812,117 B2 | 8/2014 | Gerber et al. |
| 8,849,408 B1 | 9/2014 | Gilson et al. |
| 9,743,878 B2 | 8/2017 | Drew |
| 2006/0264777 A1 | 11/2006 | Drew |
| 2012/0150251 A1 | 6/2012 | Giftakis |
| 2013/0345774 A1 | 12/2013 | Paulus et al. |
| 2014/0171820 A1 | 6/2014 | Causevic |
| 2014/0257427 A1 | 9/2014 | Marnfeldt |

OTHER PUBLICATIONS

Baldauf: "Deep Brain Stimulation: A Pacemaker for Parkinson's Disease and More", http://health.usnews.com, Jul. 15, 2009.

\* cited by examiner

IDENTIFICATION OF COMPROMISED COMPONENTS IN A MEDICAL SYSTEM

RELATED APPLICATIONS

The present application claims priority to U.S. Prov. App. No. 62/393,268 filed on Sep. 12, 2016.

TECHNICAL FIELD

The disclosure relates to medical devices and, more particularly, to medical devices for therapeutic brain stimulation.

BACKGROUND

Implantable medical devices, such as electrical stimulators or therapeutic agent delivery devices, may be used in different therapeutic applications, such as deep brain stimulation (DBS) or the delivery of pharmaceutical agent to a target tissue site within a patient. A medical device may be used to deliver therapy to a patient to treat a variety of symptoms or patient conditions such as chronic pain, tremor, Parkinson's disease, other types of movement disorders, seizure disorders (e.g., epilepsy), obesity or mood disorders. In some therapy systems, an external or implantable electrical stimulator delivers electrical therapy to a target tissue site within a patient with the aid of one or more implanted electrodes, which may be deployed by medical leads or on a housing of the stimulator. In addition to, or instead of, electrical stimulation therapy, a medical device may deliver a therapeutic agent to a target tissue site within a patient with the aid of one or more fluid delivery elements, such as a catheter or a therapeutic agent eluting patch.

SUMMARY

In general, the disclosure relates to devices, systems, and methods for identifying a component failure in an implanted medical device system, such as a system implanted to deliver deep brain stimulation (DBS) therapy. One way to detect a failure is by using acutely-measured impedance data. Such data may provide impedance information regarding an implanted DBS system that may include an implantable device, a lead extension, and a lead. Such impedance information may provide information on how the system components are interacting with the tissue and/or with one another. For instance, the data may indicate whether a component has experienced a short of an open circuit. Not all out-of-range (e.g., unusually low or high) impedance values are associated with verifiable hardware complications. Sometimes high or low impedance values may be the result of unusually high or low tissue impedance values, for instance. Conversely, sometimes verifiable hardware problems may exist that do not result in acutely-measured out-of-range impedance values.

For instance, in the case of an intermittent open or short circuit, an acutely-measured impedance value may be in-range most of the time. The open or short circuit may only manifest itself when a system component undergoes a certain type of movement or is flexed into a certain shape or position. Such a fault may be difficult to detect when only acute measurements are used. In this latter case, a loss of DBS therapy benefit may result (at least intermittently) from this type of undetected electrical shunt or short.

In accordance with the foregoing, the current disclosure provides techniques to identify and diagnose DBS system connection integrity issues for gauging the impact on therapy and suggest potential solutions. In one embodiment, a system is disclosed comprising a sensor configured to sense a first signal at a first location of an anatomy of a patient, one or more processors configured to associate a portion of the first signal with a second signal introduced at a second location of the anatomy of the patient and to determine whether a fault exists in the system based on one or more characteristics of the associated portion of the first signal. As another example, a method of detecting a fault in an implantable medical device system is disclosed comprising sensing a first signal via an electrode at a first location of an anatomy of a patient, associating a portion of the first signal with a second signal introduced at a second location of the anatomy of the patient, and determining whether a fault exists in the system based on one or more characteristics of the associated portion of the first signal, wherein one or more of associating a portion of the first signal with a second signal introduced at a second location in the anatomy of the patient and determining whether a fault exists in the system are performed by one or more processors.

The details of one or more examples of the disclosure are set forth in the accompanying drawings and the description below. Other features, objects, and advantages will be apparent from the description and drawings, and from the claims.

DETAILED DESCRIPTION

Figure 1:
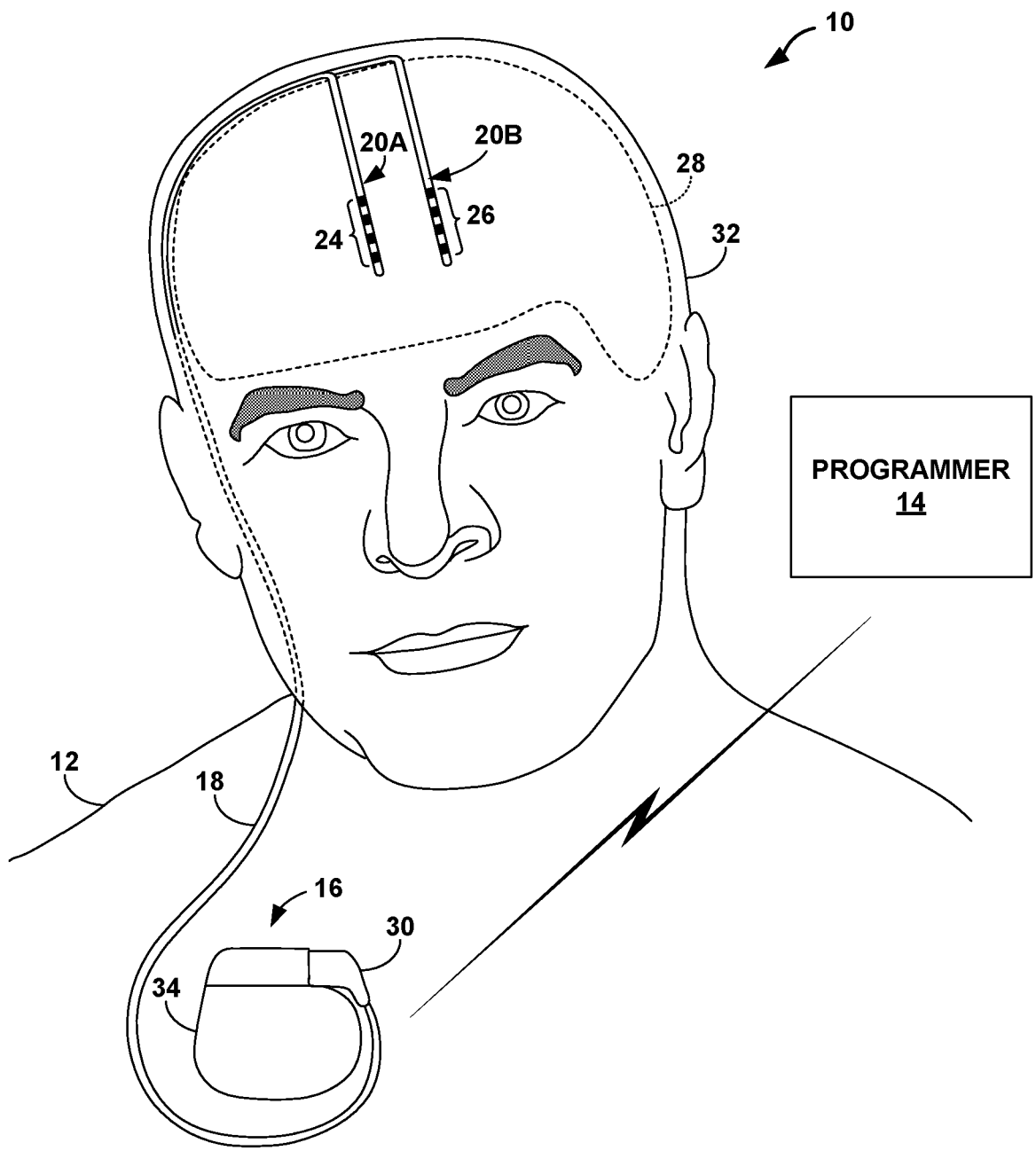
FIG. 1 is a conceptual diagram illustrating an example deep brain stimulation (DBS) system configured to deliver an example electrical stimulation therapy to a target tissue site within a brain of a patient.

The present disclosure relates to techniques for detecting and analyzing indicators of compromised DBS system components such as leads and lead extensions. Compromised components may involve those associated with short circuits or electrical shunts. Such faults may be indicated based on signals sensed from one or more DBS leads. Specifically, impedance values, evoked potential measurements (EPs), and identification of movement or ECG artifacts may be detected in the sensed brain signals. One or more of these sensed brain signals may be used to assess a failure of the system component(s). In one example, a DBS lead or lead extension is determined to be functioning or non-functioning based on an aggregate outcome of a plurality of these measures. According to this approach, failures may be detected that would otherwise go unidentified if failure analysis were based solely on acute impedance measurements. FIG. 1 is a conceptual diagram illustrating an example therapy system 10 that is configured to deliver therapy to patient 12 to manage a disorder of patient 12. In some examples, therapy system 10 may deliver therapy to patient 12 to manage a seizure disorder (e.g., epilepsy) of patient 12, which is characterized by the occurrence of seizures. Therapy system 10 may be used to manage the seizure disorder of patient 12 by preventing the onset of seizures, minimizing the severity of seizures, shortening the duration of seizures, minimizing the frequency of seizures, and the like. Patient 12 ordinarily will be a human patient. In some cases, however, therapy system 10 may be applied to other mammalian or non-mammalian non-human patients. While examples of the disclosure are described in some cases with regard to management of seizure disorders, in other examples, therapy system 10 may also provide therapy to manage symptoms of other patient conditions, such as, but not limited to, Alzheimer's disease, psychological disorders, mood disorders, movement disorders like Parkinson's disease or other neurogenerative impairment.

Therapy system 10 includes medical device programmer 14, implantable medical device (IMD) 16, lead extension 18, and one or more leads 20A and 20B (collectively "leads 20) with respective sets of electrodes 24, 26. IMD 16 includes a stimulation generator that is configured to generate and deliver electrical stimulation therapy to one or more regions of brain 28 of patient 12 via a subset of electrodes 24, 26 of leads 20A and 20B, respectively. In the example shown in FIG. 1, therapy system 10 may be referred to as a deep brain stimulation (DBS) system because IMD 16 provides electrical stimulation therapy directly to tissue within brain 28, e.g., a tissue site under the dura mater of brain 28. In other examples, leads 20 may be positioned to deliver therapy to a surface of brain 28 (e.g., the cortical surface of brain 28). In some examples, delivery of stimulation to one or more regions of brain 28, such as an anterior nucleus of the thalamus (also referred to herein as the "anterior nucleus," "anterior thalamic nucleus" or "AN"), the subthalamic nucleus (STN) or cortex of brain 28, may provide an effective treatment to manage a seizure or other disorder of patient 12.

Electrical stimulation generated from the stimulation generator (shown in FIG. 3) of IMD 16 may help prevent the onset of events associated with the patient's disorder or mitigate symptoms of the disorder. For example, electrical stimulation therapy delivered by IMD 16 to a target therapy delivery site within brain 28 may help minimize the occurrence of seizures or minimize the duration, severity or frequency of seizures if patient 12 has a seizure disorder.

IMD 16 may deliver electrical stimulation therapy to brain 28 of patient 12 according to one or more stimulation therapy programs. A therapy program defines one or more electrical stimulation parameter values for therapy generated and delivered from IMD 16 to brain 28 of patient 12. In examples in which IMD 16 delivers electrical stimulation in the form of electrical pulses, for example, the stimulation therapy may be characterized by selected pulse parameters, such as pulse amplitude, pulse rate, and pulse width. In addition, if different electrodes are available for delivery of stimulation, the therapy program may include one or more electrode combinations, which can include selected electrodes (e.g., selected from electrodes 24, 26) and their respective polarities. The exact therapy parameter values of the stimulation therapy that helps prevent or mitigate seizures, such as the amplitude or magnitude (electrical current or voltage) of the stimulation signals, the duration of each signal (e.g., in the case of stimulation pulses, a pulse width or duty cycle), the waveform of the stimuli (e.g., rectangular, sinusoidal or ramped signals), the frequency of the signals, and the like, may be specific for the particular target stimulation site (e.g., the area of the brain) involved as well as the particular patient and patient condition. While stimulation pulses are primarily described herein, stimulation signals may be of any form, such as continuous-time signals (e.g., sine waves) or the like.

In addition to delivering stimulation therapy to manage a disorder of patient 12, therapy system 10 is configured to monitor one or more bioelectrical brain signals of patient 12. For example, IMD 16 may include a sensing module that senses bioelectrical brain signals within one or more regions of brain 28. In some examples, the sensing module of IMD 16 may receive the bioelectrical signals from electrodes 24, 26 or other electrodes positioned to monitored brain signals of patient 12. In the example shown in FIG. 1, the signals generated by electrodes 24, 26 are conducted to the sensing module within IMD 16 via conductors within the respective lead 20A, 20B. Electrodes 24, 26 may also be used to deliver electrical stimulation from the therapy module to target sites within brain 28 as well as sense brain signals within brain 28. In some examples, the sensing module of IMD 16 may sense bioelectrical brain signals via one or more of the electrodes 24, 26 that are also used to deliver electrical stimulation to brain 28. In other examples, one or more of electrodes 24, 26 may be dedicated to sensing bioelectrical brain signals while one or more different electrodes 24, 26 may be dedicated to delivering electrical stimulation.

In some examples, a sensing module of IMD 16 may sense one or more first signals at a first location in the patient's anatomy (e.g., the brain) that contain some portion that may be associated with a second signal introduced into the patient's anatomy at a second location (e.g., a second location in the brain). That second signal may be, for instance, a stimulation signal delivered to the second location. This stimulation signal that is delivered to the second location may result in an evoked response (also referred to herein as an evoked potential) which may be detected within the one or more first signals.

As another example, the second signal introduced into the patient's anatomy may be associated with movement of a portion of the patient's body that results in motion artifacts being introduced at a second location. These motion artifacts may be evident in the one or more first signals sensed at the first location in the patient's anatomy, which is different from the second location. As yet another example, the second signal may be an artifact resulting from any other signal introduced into the body, such as an electrocardiogram (ECG) artifact introduced by activity (e.g., beating) of the patient's heart. A portion of the sensed signal at the first location may correspond with one or more characteristics of this signal introduced at this second location (within the patient's chest).

As discussed above, a portion of the sensed signal may be associated with this second signal that is introduced at the second location. In other words, a time correlation may exist or be determined between the portion of the sensed signal and the signal at the second location. For instance, the portion of the sensed signal may occur contemporaneously with introduction of the second signal at the second location. The portion of the sensed signal may be known to occur at the same time as, or within an expected time delay after, the second signal is introduced at this second location. Thus, this portion of the sensed signal has a temporal relationship with the second signal that may be used in some cases to determine whether there is a potential fault in one or more system components or interconnection between system components as will be discussed further below.

In some examples, bioelectrical signals sensed by IMD 16 within brain 28 of patient 12 or a separate sensing device implanted or external to patient 12 may be used to detect a compromised component or interconnection of the system. The compromised component can be, for example, a lead or lead extension that has a short or a leakage pathway. A leakage pathway may result when the insulation in the lead or lead extension has damage or imperfection that results in incomplete sealing and/or insulation of the lead conductors. A leakage pathway may also result when connections between the lead extension and the connector block 30 of the IMD 16 or the lead and the lead extension are not sealing properly such that fluid ingress in the connector block causes a low impedance pathway that compromises system operation. Similarly, a faulty connection between a lead 20 and the connector bock 30 of the IMD 16 (in those situations wherein a lead extension 18 is not used) may allow fluid ingress, again resulting in leakage paths that compromise signal transmission. Such faults can be detected by sensing bioelectrical signals according to techniques of the current disclosure.

Various combinations of electrodes may be used by IMD 16 for sensing purposes and for delivering stimulation to a patient. Moreover, sensing and delivery of stimulation may be performed at various locations in a patient's anatomy. For instance, IMD 16 may monitor brain signals and deliver electrical stimulation at the same region of brain 28 or at different regions of brain 28. In some examples, the electrodes used to sense bioelectrical brain signals may be located on the same lead used to deliver electrical stimulation, while in other examples, the electrodes used to sense bioelectrical brain signals may be located on a different lead than the electrodes used to deliver electrical stimulation. In some examples, a bioelectrical brain signal of patient 12 may be monitored with external electrodes, e.g., scalp electrodes positioned over a temporal lobe of brain 28. Moreover, in some examples, the sensing module that senses bioelectrical brain signals of brain 28 (e.g., the sensing module that generates an electrical signal indicative of the activity within brain 28) is in a physically separate housing from outer housing 34 of IMD 16. However, in the example shown in FIG. 1 and the examples primarily referred to herein for ease of description, the sensing module and therapy module of IMD 16 are enclosed within a common outer housing 34.

As previously stated, bioelectrical brain signals sensed by IMD 16 may reflect potential faults in system components. Examples of the sensed bioelectrical brain signals include, but are not limited to, electroencephalogram (EEG) signals, electrocorticogram (ECoG) signals, local field potentials (LFP) sensed from within one or more regions of a patient's brain and/or action potentials from single cells within brain 28.

In the example shown in FIG. 1, IMD 16 may be implanted within a subcutaneous pocket above the clavicle of patient 12. In other examples, IMD 16 may be implanted within other regions of patient 12, such as a subcutaneous pocket in the abdomen or buttocks of patient 12 or proximate the cranium of patient 12. Implanted lead extension 18 is coupled to IMD 16 via connector block 30 (also referred to as a header), which may include, for example, electrical contacts that electrically couple to respective electrical contacts on lead extension 18. The electrical contacts electrically couple the electrodes 24, 26 carried by leads 20 to IMD 16. Lead extension 18 traverses from the implant site of IMD 16 within a chest cavity of patient 12, along the neck of patient 12 and through the cranium of patient 12 to access brain 28. IMD 16 is constructed of a biocompatible material that resists corrosion and degradation from bodily fluids. IMD 16 can comprise a hermetic outer housing 34, which substantially encloses components, such as a processor, therapy module, and memory. In the example shown in FIG. 1, leads 20 are implanted within the right and left hemispheres, respectively, of brain 28 in order deliver electrical stimulation to one or more regions of brain 28, which may be selected based on many factors, such as the type of patient condition for which therapy system 10 is implemented to manage. Other implant sites for leads 20 and IMD 16 are contemplated. For example, IMD 16 may be implanted on or within cranium 32 or leads 20 may be implanted within the same hemisphere or IMD 16 may be coupled to a single lead that is implanted in one or both hemispheres of brain 28.

Leads 20 may be positioned to deliver electrical stimulation to one or more target tissue sites within brain 28 to manage patient symptoms associated with a condition of patient 12. Leads 20 may be implanted to position electrodes 24, 26 at a target implantation site within brain 28 via any suitable technique, such as through respective burr holes in a skull of patient 12 or through a common burr hole in the cranium 32. Leads 20 may be placed at any location within brain 28 such that electrodes 24, 26 are capable of providing electrical stimulation to one or more target therapy delivery sites within brain 28 during treatment.

Different neurological or psychiatric disorders may be associated with activity in one or more of regions of brain 28, which may differ between patients. For example, in the case of a seizure disorder or Alzheimer's disease, leads 20 may be implanted to deliver electrical stimulation to regions within the Circuit of Papez, such as, e.g., the anterior nucleus (AN) of the thalamus, the internal capsule, the cingulate, the fornix, the mammillary bodies, the mammillothalamic tract (mammillothalamic fasciculus), and/or hippocampus. Regions of brain 28 may be functionally connected to one another via neurological pathways such that activity within one region of brain 28 may affect activity within another region of brain 28. For example, electrical stimulation delivered by IMD 16 to a particular region of brain 28 may influence brain signals in one or more other regions of brain 28. In some examples, brain activity can be indicated by a signal characteristic (e.g., an amplitude, frequency, and/or frequency domain characteristic) of a bioelectrical brain signal. As an example, the signal characteristic of a bioelectrical brain signal sensed within a particular region of brain 28 may change as the brain activity in the region changes.

One example of functionally connected regions of brain 28 includes the Circuit of Papez (described below with respect to FIG. 5). Electrical stimulation delivered from IMD 16 to a particular region of the Circuit of Papez may influence brain signals in one or more other regions of the Circuit of Papez. In other words, a brain signal sensed at one location in the Circuit of Papez may contain one or more characteristics that are indication of a response to stimulation in another different location in this circuit. In some examples, the one or more characteristics comprise a waveform that is indicative of an evoked response (i.e., an evoked potential) that occurred within the brain because of stimulation in another different location in the circuit.

As described in further detail below, in some examples, a potential system fault may be detected based on one or more characteristics of a signal sensed in a first region (first location) of the brain as the result of electrical stimulation delivered to a second region of brain 28 that is different than the first region, but functionally connected to the first region. The electrical stimulation delivered to the second region of the brain 28 may be relatively low frequency stimulation which, in one example, may have a frequency ranging between 1 and 20 Hz, and in more particular examples between 2 and 10 Hz. Delivery of low frequency stimulation at one location in the anatomy (e.g., at a second region of the brain) may be associated with at least a portion of a biological signal sensed in the first location in the anatomy (e.g., a first region or location of the brain). For instance, a portion of the sensed biological signal that was sensed during delivery of this stimulation and/or within some predetermined time delay thereafter may be the portion that is associated with this stimulation signal, because it is the portion the sensed biological signal that has the possibility of being affected by this stimulation. This portion of the sensed biological signal may possess characteristics on which a determination concerning the possibility of a system fault may be based.

In some examples described herein, a first signal sensed by one or more of electrodes 24, 26 of leads 20 is sensed within a first region of the Circuit of Papez. This first signal may be sensed sometime during or after (e.g., immediately after or within some predetermined duration of time thereafter) a relatively low frequency electrical stimulation signal is delivered to a different second region of the Circuit of Papez. Based on the sensed signal, a potential fault may be detected in a component of the medical system.

According to example techniques, a target site for delivering stimulation within the second region of the brain in the manner discussed above is the site selected for treating a seizure disorder of patient 12. This site may be selected by delivering a relatively low frequency stimulation (e.g., between 1 and 20 Hz, or between 2 and 10 Hz) to a region of brain 28 and determining an evoked potential in a region believed to be the seizure focus. For example, a relatively low frequency stimulation may be delivered to an area of the AN of brain 28 and the local field potential (LFP) in the HC that is evoked by the delivery of stimulation to the area of AN may be determined. This local field potential may be sensed immediately, or after a short delay, following the delivery of stimulation to the area of AN, and may be referred to as the evoked potential (EP). This evoked potential may be characterized by the peak amplitude of a sensed bioelectrical brain signal, which results when the brain activity in the thalamus propagates to the HC. Thus, the evoked potential is an excitatory response of the HC to the stimulation delivered to the thalamus. The relatively low frequency stimulation within the AN generates a spike in brain activity in the HC. The target location for delivering stimulation may be selected as that location that results in an evoked potential in the HC having a particular characteristic.

In example techniques, the stimulation site in the AN that results in the greatest evoked potential in the HC (e.g., the brain signal with the greatest average peak amplitude for a time period following the delivery of the stimulation to the thalamus) is selected as the target stimulation site. This is because the area of the AN associated with the greatest evoked potential in the HC may have the strongest functional connection to the HC, such that delivery of stimulation to the area of the AN may provide efficacious stimulation therapy for managing the seizure disorder of patient 12. In other cases, the characteristic of the sensed response in the HC that is used to select the target stimulation location in the AN may be some other characteristics. The characteristic may be a frequency domain characteristic or a time domain characteristic of the bioelectrical brain signal. Examples of a time domain characteristic include, but are not limited to, a mean, median, instantaneous, peak or lowest amplitude of the bioelectrical brain signal within a predetermined period of time. Examples of a frequency domain characteristic include, but are not limited to, a power level in one or more frequency bands of a bioelectrical brain signal sensed over a predetermined period of time or a ratio of power levels in at least two frequency bands of the bioelectrical brain signal.

Once this target location for delivery of therapeutic stimulation has been determined, a lead may be located at this site to provide chronic stimulation to treat the patient's disorder (e.g., seizure disorder). Another, second lead may be located within the AN to continue to monitor the seizure focus location. According to aspects of this disclosure, these two leads may be used to detect the possible existence of component failures or faults within the medical device system. For instance, it may be known that a particular response is generated within the HC by stimulation delivered to the AN when no fault is present in the system. That is, it may be known that a biological signal having a particular waveform envelope, amplitude, duration, etc. may be expected to be sensed in the HC when low-frequency stimulation is delivered to the AN. This particular biological signal sensed within the HC may be unique to a given patient, or in some cases may be common to a given patient population that has a similar disorder, has a lead placement similar to that of the current patient, and so on. This biological signal may be the signal that is expected to be sensed in the absence of a system fault and may be considered a baseline signal for system diagnostic purposes. In one example, such a signal is recorded at a time when system components may be assumed, or are known, to be defect-free. For instance, this type of baseline signal may be recorded after it has been determined that impedance measurements of system components are all within normal ranges and patient response to stimulation are as expected for an operational system. At such a time, the baseline biological signal may be obtained and stored within a memory (e.g., a memory of IMD 34) for later use.

In some cases, the baseline signal may be obtained by processing multiple instances of a patient's measured response signal. For instance, at multiple times throughout a predetermined time period, stimulation (e.g., low frequency stimulation) may be delivered to the AN and an evoked response may be recorded in the HC. Signal processing may be performed on the multiple signal recordings to generate a mean, median, or some other signal that is representative of, or a composite of, the multiple signal recordings. In another example, the baseline signal may be obtained, at least in part, from an expected response derived from patient population data, wherein the population data is derived from patients having a similar demographic data (e.g., same sex, similar age, similar/same disorder and disease progression, etc.), a similar system configuration, similar lead placement and/or are receiving a similar therapy as compared to the current patient.

Sometime later after one or more baseline response signals have been obtained, it may be determined that stimulation delivered to the AN is not resulting in a signal that is the same as, or similar to, the same previously-obtained baseline biological signal. For instance, stimulation that is similar to, or the same as, that delivered to the AN to obtain the baseline signal may be delivered to the AN and a signal may be sensed within the HC. At least a portion of that sensed signal may be associated with delivery of stimulation to the AN. For instance, a portion of the sensed signal that is sensed at the same time as, and/or after some expected delay following stimulation of the AN may be associated with the stimulation. This may be the portion of the sensed signal in which the expected response may be located. Template matching techniques may be used to determine whether the stored baseline signal is similar to the newly-recorded signal, or whether one or more characteristics of the sensed signal are different from the stored baseline signal. Characteristics used in the comparison may include amplitude of the response, response duration, waveform morphology of the response, and so on. In other examples, frequency domain data may be used in addition to, or instead of, time domain data to compare the previously-recorded baseline signal to the newly-recorded response. In such cases, the power level in one or more frequency bands may be compared between the baseline and newly-recorded signal to determine if discrepancies are evident. In some scenarios, a ratio between the baseline and newly-recorded signal may be derived and compared to a threshold to determine if discrepancies are present.

If no fault exists in the system, it is likely that characteristics of the associated portion of the sensed signal will be similar to the baseline signal such that a match is indicated.

However, if a fault exists in the system, the associated portion of the sensed signal may be degraded as compared to the baseline signal. For instance, the amplitude of the signal or the waveform characteristics may be degraded in comparison to those of the baseline biological signal as will be discussed further below. Alternatively, none of the characteristics of an evoked response may be present within the associated portion of the signal, indicating that there is no detectable response present in this portion of the sensed signal at all. In such a situation, the expected response to the stimulation is not detected, pointing to the possibility that some component (a lead, lead extension, or an associated connector) in the path delivering stimulation or detecting the response has a fault such as an open pathway preventing signal conduction.

The foregoing describes a situation wherein a functional connection between the AN and HC allows a signal sensed in the HC to detect an evoked response (or evoked potential) resulting from stimulation delivered in the AN. The functional connection within the brain between the AN and HC also allows stimulation delivered in the HC to result in a response that may be sensed within the AN. Thus, in a manner similar to that described above for obtaining a baseline signal in the HC during a time when it is known that faults are absent in the system, a baseline signal may additionally or alternatively be recorded or generated from signals sensed in the AN. For instance, a generated signal may be derived from one or more instances of signals sensed in the AN during, and/or shortly after, stimulation provided in the HC. Alternatively, some population data may be used to derive or obtain this baseline signal. This baseline signal may be indicative of the expected response when no fault is present in the system. This baseline signal may be stored within memory 62 of the IMD 16, memory of programmer 14, or some other system memory for later use.

Sometime later, the stored signal may be retrieved and compared to a signal recorded in the AN that is contemporaneous with stimulation in the HC. If the later-obtain signal in the AN does not reflect the presence of an evoked response at all, or signal characteristics indicative of an evoked response have degraded, a potential fault may have occurred within the system. In the foregoing manner, functional connections within the brain such as those in the circuit of Papez may allow stimulation at a first location and sensing at a second location and/or stimulation at the second location and sensing at the first location to be used to determine whether a fault may exist within the system.

Using sensing at both a first location and at a second location may provide more information than sensing at just one location. In other words, it may be advantageous to sense a possible evoked response at a first location during and/or after stimulation at a second location as well as to sense for a possible evoked response at the second location during and/or after stimulation at the first location. This additional information may help to further analyze and pinpoint the location and nature of the potential fault as will be discussed further below.

While examples in which a target therapy delivery site within the AN of brain 28 is used in conjunction with sensing of a brain signal within the HC to detect a potential fault, in other examples, the techniques described herein may also be used to select a target stimulation site within other regions of brain 28. For instance, in some cases, stimulation may be delivered to the subthalamic nucleus (STN) and a signal may be detected from the motor cortex using cortical electrodes. In such an example, electrocorticogram (ECoG) signals may be sensed by the cortical electrodes to determine whether a response is detected as a result of stimulation delivered to the STN.

Conversely, in some cases, the cortical electrodes may be used to deliver stimulation to the motor cortex to determine whether a signal sensed elsewhere within the brain, such as within the STN, is indicative of an evoked response. In yet other examples, one or more electrodes may be placed subgaleally between the skull and the scalp. For instance, a Reveal LINQ® device commercially available from Medtronic, plc is a battery-powered loop recorder having a housing carrying multiple electrodes. This device may be injected into the subgaleal space to sense a signal that may contain one or more characteristics of an evoked response occurring because of stimulation delivered at a different location in the brain, such as stimulation delivered by lead 20 coupled to IMD 34. Such stimulation may be delivered to the STN or the AN of the thalamus, for example. The delivery of the stimulation by IMD may be wirelessly synchronized with recording by the LINQ device of the sub-Q signal so that a portion of the recorded signal may be associated with the stimulation. By such synchronization, the portion of the signal in which a potential response to the stimulation may be recorded and analyzed (if such a response is indicated by the recorded signal). The recorded signals may be stored within the LINQ device itself, and/or may be wireless transferred to an external device such as programmer 14 or even to IMD 34. Additionally or alternatively, such recordings may be uplinked to a "cloud-based" server system for analysis and retention.

In still other cases, one or more electrodes placed external to the patient's body may be used to sense an EEG signal based on stimulation delivered to a location in the brain. For instance, EEG electrodes that are coupled (either in a wired or wireless manner) to a recording device can be used to record signals from the patient's scalp in a conventional manner. The recording of these signals can be synchronized to stimulation delivery in a manner similar to that described in the foregoing paragraph. Recordings may be compared to baseline EEG recordings that were obtained when it was known that the system did not contain faults. In a manner similar to any of the above-described examples, the EEG recordings may be used to determine whether an expected evoked response signal is evidenced by signal characteristics present in a portion of the recorded signals that are associated with stimulation delivered to the brain. Such stimulation may be delivered by one or more electrodes 24, 26 of leads 20 that are coupled to IMD 34 (FIG. 1). Stimulation may be delivered to the STN or AN of the thalamus, as one example, and recorded signals may be obtained from various locations on the scalp. The EEG electrodes may record what is known as an "EP recruitment rhythm" which is indicative of the response being evoked by the stimulation.

In some examples, stimulation and sensing may occur within the same hemisphere of the brain, but this need not be the case. For example, stimulation in the HC of a first hemisphere of the brain can evoke a response in the HC of a second hemisphere via the dorsal hippocampal commissure. In a manner similar to that discussed above, baseline signals may be derived or recorded at a location of a second hemisphere at which recording will be performed for comparison to later-obtained recordings.

As may be appreciated from the foregoing, various combinations of sensing and stimulation are possible, with stimulation occurring at locations that are known to be functionally coupled to the sensing locations. Such locations may be in the same, or different, hemispheres of the brain. Sensing and stimulation locations may comprise those within deep brain structures, cortical structures, locations within the subgaleal space, and locations on a surface of the body (e.g., the scalp).

In a manner described above, at least a portion of a signal sensed at a first location may be associated with a signal introduced at a second location, such as a stimulation signal delivered at a second location. The portion of the signal that is so associated may be analyzed to determine whether characteristics of an expected evoked response signal are present in that signal portion, as may be expected if no faults have occurred within the system. If such characteristics are degraded, or not present at all, it may indicate a potential failure in the system.

As may be appreciated, when expected characteristics are either degraded or not present at all, a fault may exist within a stimulation path, such as within a lead, lead extension and/or electrode(s) that deliver the stimulation and/or a fault may exist within a sensing path, such as within a lead, lead extension and/or electrode(s) that sense the response. To further determine in which path the fault may reside, additional information may be needed. For instance, in the case in which characteristics of the expected evoked response signal are absent from an associated portion of the sensed signal, it may further be determined whether the sensed signal is indicated of physiological activity that may be expected to be obtained from the sensed location in the absence of such a response. As a particular example, a signal sensed within the AN may reflect a relatively high level of theta activity. This theta activity will typically be present in the absence of stimulation in the HC and will result in a sensed signal having a characteristic signature indication of such activity. If a signal sensed in the AN during, or just after, stimulation is delivered to the HC is devoid of any characteristics of an expected evoked response due to the stimulation but yet reflects the characteristic signature indication of theta activity expected in the AN, it may be determined that the fault lies in the stimulation path. On the other hand, if both characteristics of the evoked response as well as characteristics of the expected theta wave signature are missing from the signal sensed in the AN, it may be likely that a fault lies in the sensing pathway.

Once a determination of the type described above has been made, the stimulation/sensing roles of the various lead/electrode pathways may be reversed so that, for instance, an electrode positioned within the AN delivers the stimulation while an electrode in the HC senses a corresponding signal. If it had been determined in the first iteration described in the foregoing paragraph that a fault likely exists in the path involving the electrode(s) in the HC rather than in the AN, then sensing by that path in the second iteration will likely reveal degraded or non-existent characteristics of an evoked response, and will also indicate that the expected HC signal (that is, the signal that is expected to be sensed in the absence of the evoked response) is also degraded, or does not include the expected signal characteristics. Conversely, if it had been determined in the first iteration that a fault likely exists in the path involving the electrode(s) in the AN, then sensing by the electrode(s) in the HC will likely reveal degraded or non-existent characteristic of an evoked response, but will reflect the expected HC signal characteristics. In this manner, switching the stimulation/sensing roles of the pathways helps to further confirm a likely location and cause (e.g., pathway) of a fault.

In some examples, a lead shift may be the result of a loss of an expected evoked response signal rather than a system fault. In this case, an electrode combination that had previously been used to generate a baseline signature for use in detecting evoked responses may no longer be as capable of sensing characteristics of such a response because the lead has shifted upward or downward in the anatomy. In such cases, it is likely that a different electrode combination may be able to sense the characteristics of the evoked response. This would likely not be the case if the cause of the loss of the evoked potential signal were instead an open, short, or leakage path in the sensing pathway. By cycling through different electrode combinations to obtain different sense signals while stimulation is delivered at a second location in the brain, it may be determined whether a system failure (e.g., failure in a lead, lead extension, electrode, etc. in the sensing pathway) or a shift in lead location is the cause of the signal loss.

In a similar manner, if it is determined that a likely fault may exist somewhere within a stimulation pathway, multiple different combinations of available electrodes in the stimulation pathway may be tried to determine if all such combinations fail to elicit a sensed evoked response in a sensing pathway. If all such combinations fail in this regard, it may be likely that a fault exists in a component that is common to all electrode combinations, such as faulty connection between a lead and lead extension 18, a lead and connector block 30, lead extension and connector block 30, and so on. If only some of the stimulation electrode combinations fail to result in an evoked response, the fault may likely be in some component that is not common to all combinations such as a fault in one of the electrodes of the failing combination or a failure in one or more conduction paths that are solely coupled to the failing electrode combination(s).

As may be appreciated, various combinations of sensing and stimulation, including stimulation using various electrode combinations, may be used to gather information that is useful to further analyze a likely fault occurring in a component of a medical device system.

When a likely fault is detected, it may be desirable to further confirm and/or analyze the fault using additional signal data. For instance, it may be desirable to evaluate a sensed signal, such as a biological signal sensed in the brain, to determine whether some other signal that originated elsewhere in the patient's body (e.g., an artifact) may provide more information on whether a potential fault has occurred in a system component. As an example, a signal such as a local field potential signal may be sensed within a location of a brain of a patient at a time the patient performs a motion task. This motion task may involve the patient turning his or her head from side to side, or nodding his or her head up and down. It may instead involve swinging the arms around the torso, repeatedly bending at the waist or some other task that may flex the lead extension or lead body. In another example, it may involve palpating the site of the IMD implant. This motion may cause a motion artifact that is present in the sensed signal (e.g., local field potential signal) because of leakage pathways resulting from insulation breaks or incomplete sealing of the system components. Such artifacts may be intermittent and may coincide with a particular location of the head, for example, as the patient continues with head rotation. Such artifacts may evidence a regular frequency that coincides with the frequency at which the patient is moving, further providing confirmation of a break/open or a short that is being exposed by the motion. An artifact of this type may be a notable spike, or amplitude increase, that occurs at a regular frequency and/or time associated with the motion. This likely time correlation with the movement will provide an indication that this activity is not associated with a physiological signal (e.g., not the result of a seizure or after discharge event) but rather is associated with a component fault in the system.

Such motion artifacts in a sensed signal may correspond to a particular portion of the sensed signal that is associated with the motion. For instance, a local field potential signal may be sensed over a predetermined time period. The patient may be directed to enter into motion only during a portion of this time period. The portion of the sensed signal obtained during the time when motion was occurring may be compared to the portion of the sensed signal when no motion was occurring to determine if motion artifacts are present in the signal. In some cases, other characteristics of the signal may be analyzed with respect to the motion. As discussed above, the analysis may determine whether a frequency at which the patient is turning his or her head corresponds to a frequency of a characteristic of the sensed signal. In this manner, it may be determined whether a motion artifact has been introduced into the sensed signal such that a component failure may exist.

In the foregoing manner, one or more processors within the system are configured to associated a portion of the sensed signal (e.g., the LFP signal sensed in the brain during motion of the patient) with a second signal introduced at a second location of the anatomy (e.g., a motion signal resulting from twisting of the torso, turning of the head, etc.). Characteristics of the sensed signal may be indicative of whether a fault exists in the system. As discussed above, such characteristics may comprise characteristics obtained from a sensed time-domain signal, such as an increased amplitude of a portion the signal or an envelope of the signal. This may comprise, for instance, characteristic signal spikes. Alternatively or additionally, a duration of the signal may be indicative of the fault. For instance, a very narrow spike may occur because of an intermittent fault that manifests itself only during a short portion of the motion. As another example, a frequency of the signal (e.g., the frequency at which spikes occur) may coincide with frequency of motion and may provide another confirmation that the signal indeed is the result of the motion.

In some cases, a baseline time domain signal may be obtained at a time when the system is known to be free of faults. As in the case discussed above related to evoked responses, this baseline time domain signal may be obtained while the patient is moving but while no faults are suspected to exist within the system. Such a signal, which may be an LFP signal sensed from an electrode within a patient's brain, may be stored, for instance, in a memory within the system for comparison to a later-obtained signal that is obtained when some fault may be present within the system. Comparison of the later-obtained signal to this baseline may be used to determine whether a fault exists. Additional or alternatively, characteristics of the sensed signal obtained during patient motion may comprise those determined based on a frequency domain signal. That is, a transformation such as a FFT transformation may be performed on the sensed time domain signal (e.g., the LFP signal) to generate a frequency domain signal. A characteristic of that frequency domain signal may be used to determine whether a fault exists. For instance, a notable increase in the power level of a particular frequency or frequency band that is present during motion but absent when the patient is not moving may indicate the presence of an open or short in the system component. In this manner, characteristics from the time- and/or frequency-domain signals may be used to perform fault analysis.

In some examples, a baseline frequency domain signal may be obtained from the baseline time-domain signal. Such a signal may be indicative of the signal obtained during patient motion but when it is known that no fault is present in the system. Such a signal may be obtained, for instance, by performing a transformation such as an FFT transformation on a time-domain signal LFP sensed while a patient was undergoing motion and while it is known that the system is free of faults. This baseline frequency domain signal may be compared to the frequency domain signal obtained later when a fault may be present in the system. Comparison between the baseline and the later-obtained signal may be used to analyze whether the system may be subject to a fault.

Although the foregoing discussed use of LFP signals obtained during patient movement to analyze a failure in one or more components (or interconnections between components) of a system, other types of signals may be used for this purpose, such as EEG signals, ECoG signals, and/or any of the other types of signals described herein or otherwise known to be suitable in regards to evoked potentials.

The foregoing discusses use of patient movement to introduce a signal into the patient's body that may be used to further analyze system faults. Still other types of signals may be introduced into the body for this purpose. By way of another example, and in a manner similar to the foregoing, a brain signal such as an LFP signal may be sensed to determine whether it exhibits characteristics of a cardiac activity, such as a cardiac artifact (e.g., an ECG artifact.) Generally, when no fault has occurred within the system, electrodes 24, 26 will not exhibit characteristics of cardiac activity. However, when fluid ingress has caused a leakage pathway into the system, the relatively large waveforms (e.g., ECG waveforms) generated by electrical activity of the heart contaminate or completely mask out the relatively small neural signals that would otherwise be sensed by electrodes 24, 26 in the brain. This is because the cardiac signals have amplitudes in the millivolt range, whereas neural signals have a much smaller amplitude, generally in the microvolt range). The presence of an ECG signal that is overlaying, or completely masking a neural signal may be an indication of a leakage pathway in a header block of IMD 34, in a connector that couples a lead 20 to a lead extension 18, a pathway resulting from a breach in a lead or lead extension insulating body, and so on.

Other larger signals introduced into the patient's body may likewise by used in addition to motion artifacts and cardiac activity artifacts to determine the existence of faults in the system. For instance, "tapping" on the housing of the IMD located under the skin may generate a relatively large signal that will travel through the body and be picked up by a system component if a fault is present. Such a signal will likely not be sensed within a brain signal if no such fault exists. Similar types of introduced signals may also be used for this purpose, such as asking the patient to clap their hands, and so on. Thus, a variety of different types of signals may be introduced at a second location within the body while sensing is occurring a different first location in the body (e.g., within or on the brain) that can be used to perform fault analysis.

As may be appreciated, when any of the types of signals are introduced into the body, it may be beneficial to determine whether only one, or both leads in a dual lead system, are detecting any resulting artifacts. If both leads are detecting these artifacts, it may be an indication that a header block of IMD 34 has experienced a leakage path that is affecting both sensing pathways provided by both leads. On the other hand, if only one of the leads is detecting these artifacts, the fault is likely in a component of that pathway (e.g., the lead, lead extension, a connector component affecting connections in this pathway, or some other component in the pathway.)

The aforementioned techniques provide mechanisms for detecting a fault in an implantable medical device system. According to an example method, a first signal is sensed via a sensor (e.g., an electrode) at a first location of an anatomy of a patient. A portion of this first signal is associated with a second signal introduced at a second location of the anatomy of the patient. This second signal introduced at a second location may comprise a stimulation signal, a motion artifact, a cardiac artifact, or any other signal that may be present or introduced in the patient's body that may result in signal characteristics sensed in the signal sensed at the first location. In one example, a portion of the first signal is associated with the second signal by time-correlating the occurrence of the second signal with the portion of the first signal. That is, a portion of the first signal is so associated if that portion is obtained contemporaneously with the occurrence of the second signal (either at the same time or at a time thereafter, where this time may be associated with an expected delay in the transmission of the signal from the second to first location.) The method further comprises determining whether a fault exists in the system based on one or more characteristics of the associated portion of the first signal. For instance, such characteristics may indicate a loss or degradation of an expected evoked response signal that would otherwise have been present in the sensed signal. Such a loss or degradation can be detected, for instance, by comparison of the associated portion of the first signal with a baseline signal, which may be a signal stored in memory of IMD 34, programmer 14, or stored somewhere else and used as a template for comparison against the first signal. The characteristics may be time- or frequency-domain characteristics.

In another example, a system is disclosed that comprises a sensor configured to sense a first signal at a first location of an anatomy of a patient, and one or more processors configured to associate a portion of the first signal with a second signal introduced at a second location of the anatomy of the patient and to determine whether a fault exists in the system based on one or more characteristics of the associated portion of the first signal.

Figure 3:
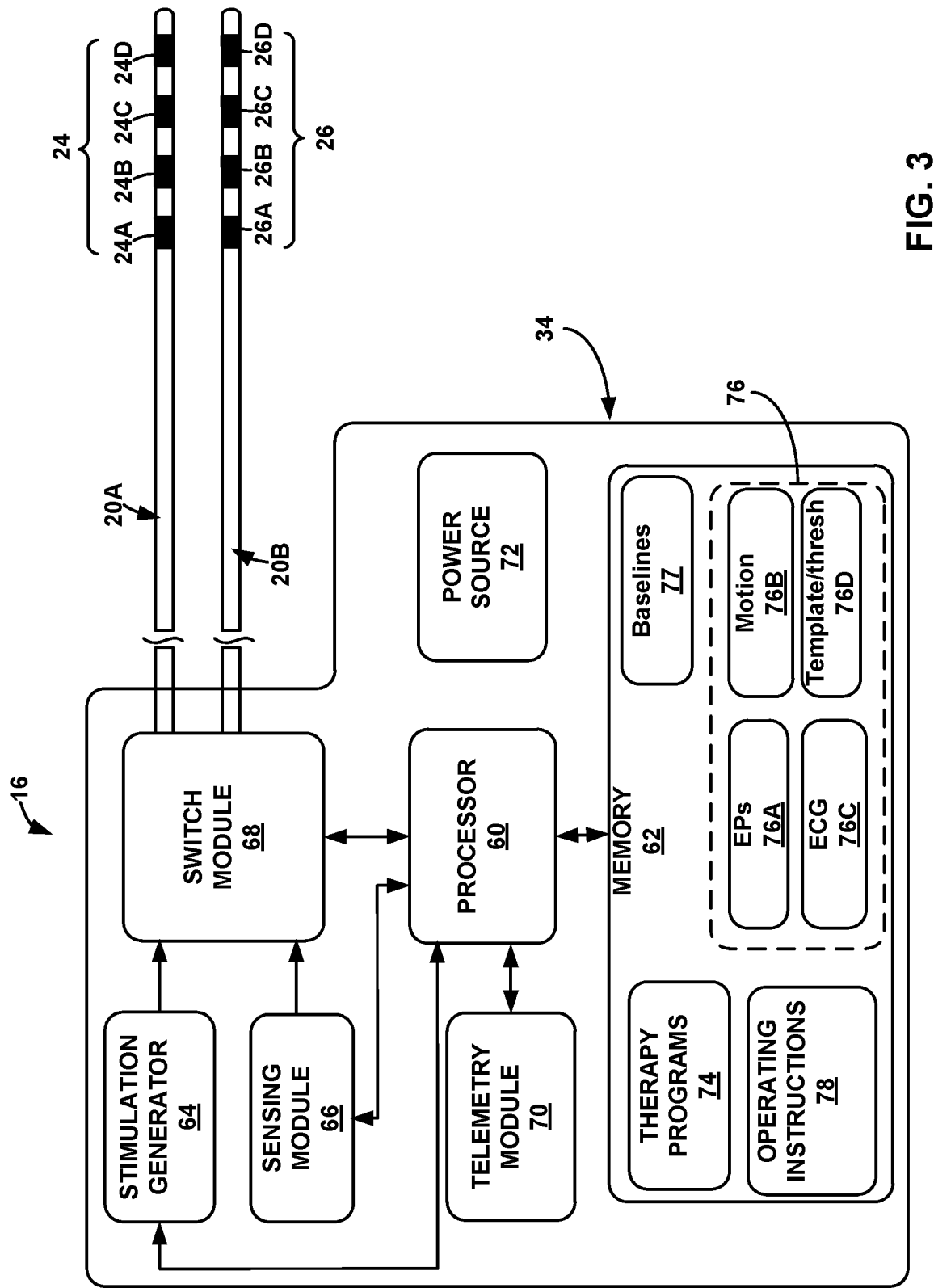
FIG. 3 is functional block diagram illustrating components of an example medical device.

In some examples, it may be beneficial to utilize impedance measurements in conjunction with sensed signals for use in system fault determinations. Impedance measurements may be used to determine the impedance existing within a particular sensing pathway, for instance. Such a measurement takes into account the tissue impedance as well as impedance resulting from the components in that pathway, such as the conductors, the electrodes, and any other circuit components in that pathway. One example way in which to determine such an impedance is for IMD 34 to output a current via electrodes 24, 26 coupled to the tissue, and to then determine a voltage caused by the flow of current through the tissue. The voltage value may be divided by the current to determine the tissue resistance. Such operations may be performed, for example, by processor 60 of IMD 34 (FIG. 3). Conversely, the IMD 34 may output a voltage via electrodes 24, 26 coupled to the tissue, determine a current caused by the voltage applied to the tissue, and divide the voltage by the current to determine the impedance of the path.

Various techniques, circuits, and systems for sensing and measuring impedance generally, and in particular for measuring impedance in medical applications, are described in U.S. Patent Application No. 62/084,252 entitled "Tissue Resistance Measurement" filed Nov. 25, 2014 and U.S. patent application Ser. No. 14/952,675 entitled "Tissue Resistance Measurement" filed Nov. 25, 2015. Such techniques, circuits, and system are further described in U.S. patent application Ser. No. 12/872,552 filed Aug. 31, 2010, now U.S. Pat. No. 9,615,744, U. S. Pat. Nos. 7,391,257, 7,622,988, and 9,197,173, all of which are entitled "Chopper-Stabilized Instrumentation Amplifier for Impedance Measurement" and all of which are assigned to the assignee of the present disclosure. All of the foregoing documents are incorporated herein by reference in their entireties.

In some of the example impedance sensing circuits referenced herein, the impedance measurements can be taken in substantially real-time. That is, a succession or sequence of impedance values may be obtained over time as, for instance, the patient is undergoing motion. The impedance measurements may be time-correlated with the patient's motion so that opens and shorts occurring as the patient moves will be reflected in the time-sequence of measurements obtained for a particular circuit pathway (e.g., the pathway including multiple electrodes and the conductors coupled to these electrodes.)

As a particular example of the foregoing, a user such as a clinician or patient may provide input such as by interacting with a user interface of a programmer or some other external device and/or by tapping on the IMD 34 in a way that may be detected by an on-board accelerometer. Such user input may be provided at a time that corresponds with the turning of a patient's head or some other movement. Such input may cause a timestamp to be stored in memory to indicate time(s) of patient motion. Corresponding timestamps may be introduced into a stream of impedance values by a system clock (e.g., a clock of IMD 34 and/or a clock of programmer 14). If such impedance values are obtained in real-time or substantially in real-time, the timestamps introduced into the stream of measurement data may be correlated to the stored timestamps associated with patient movement. In this way, it may be possible to determine that each time a patient performs a certain type of motion an out-of-range impedance value is detected on one or more sets of electrodes 24, 26. Such an out-of-range value may indicate an unusually high impedance value (e.g. an impedance value that is above some selected impedance value threshold for the particular system) or an unusually low impedance value (e.g., an impedance value that is below some selected impedance value threshold for the system). In some cases, these high and low threshold values may be programmable or otherwise selectable values, and in other cases these may be determined by, for instance, a supplier of the medical system or a clinician. In any event, a stream or sequence of such impedance values can be used to confirm the suspected presence of an open or short in the system, particularly when coupled with other information such as that described above.

A time-correlated stream, or sequence, of impedance values obtained in real- or substantially real-time may be stored in memory of IMD 34, stored within programmer 14, stored in some other external device (e.g., a clinician workstation a cell phone or PDA, or some other device), and/or uploaded to "the cloud" for storage on a central database. This data may further be used to generate information that may be presented to a clinician. For instance, a display on a screen of programmer 14 may be used to illustrate in a graphical or other format the variation in impedance over time. This graphical or other display could be annotated to indicate the times at which patient movement occurred (e.g., the times of head movement) so that the clinician can determine whether a likely short or open is occurring intermittently with some type of movement.

A display of the type discussed above may also be correlated (e.g., on a common time axis) with a graphical representation of the patient's movement (e.g., a representation of a head performing rotational movements at the same frequency as was performed by the patient) along with a rolling window displaying the stream of impedance data so that a clinician can determine a likely rotational position of a patient's head at the time of an intermittent short of open, and thereby aid in the diagnosis of the system fault.

In some examples, graphical motion and/or impedance data may be presented on a common timeline with sensed data of the type discussed above. Sensed data may include LFPs, ECoGs, EEGs or some other physiological sensed signal that may reflect a motion artifact resulting from the patient's movement. If such data has been time-stamped during collection so that it can be cross-correlated with the stream of impedance data, a clinician may be able to readily correlate high- or low-impedance values that occur at the same time as (or substantially the same time as) as motion artifacts that are present in the sensed signals. Again, such motion artifacts may be manifested as short, high-amplitude, spikes in the system that are non-physiological in nature. Such signals may be characterized as non-physiological because of their consistent non-physiological frequency (e.g., corresponding to frequency of patient motion rather than any frequency naturally occurring within the physiological signal). This may allow the user to more readily determine the likelihood of a fault, and may provide further confirmation of a motion-induced open or short in the system.

Other types of information may also be useful in further diagnosing a potential system fault. For instance, it may be determined whether a patient has experienced a potential loss in therapy efficacy. As one example, a patient suffering from Parkinson's disease may be receiving stimulation to an area of the STN to treat symptoms such as bradykinesia or dyskinesia. The clinician may note that based on recorded therapy modification made by the patient to stimulation amplitude, as may be recorded in an electronic therapy diary stored within memory of IMD 34, the patient has systematically requested ever-increasing stimulation amplitudes while obtain less relief from their symptoms. This loss or degradation in therapy efficacy may point to a short or open in a pathway providing the stimulation to the STN. When taken in conjunction with other information gathered according to one or more of the aforementioned techniques, this information involving a change in therapy efficacy may be used to pinpoint the source of the failure. Returning now to a discussion of FIG. 1, IMD 16 may deliver therapy to the brain 28 in a manner that influences the brain signals within one or more regions of brain 28. For example, IMD 16 may deliver therapy to the AN, HC, STN, or other suitable region of brain 28 to control a brain state of patient 12 in a manner that effectively treats a disorder of patient 12. For example, in the case of a seizure disorder, IMD 16 may deliver therapy to a region of brain 28 via a selected subset of electrodes 24, 26 (referred to herein as an electrode combination) to suppress a level of brain activity within the AN, HC, or another brain region associated with the occurrence of seizures (e.g., a seizure focus of brain 28). IMD 16 may deliver therapy to brain 28 via a selected subset of electrodes 24, 26.

Although leads 20 are shown in FIG. 1 as being coupled to a common lead extension 18, in other examples, leads 20 may be coupled to IMD 16 via separate lead extensions or directly coupled to IMD 16. Moreover, although FIG. 1 illustrates system 10 as including two leads 20A and 20B coupled to IMD 16 via lead extension 18, in some examples, system 10 may include one lead or more than two leads.

In the examples shown in FIG. 1, electrodes 24, 26 of leads 20 are shown as ring electrodes. Ring electrodes may be relatively easy to program and are typically capable of delivering an electrical field to any tissue adjacent to leads 20. In other examples, electrodes 24, 26 of leads 20 may have different configurations. For example, electrodes 24, 26 of leads 20 may have a complex electrode array geometry that is capable of producing shaped electrical fields. The complex electrode array geometry may include multiple electrodes (e.g., partial ring or segmented electrodes) alone, or in combination with ring electrodes. The partial ring or segmented electrodes may be provided around the perimeter of each lead 20, (in contrast to a full ring electrode which extends around the entire circumference of the lead body.) In this manner, electrical stimulation may be directed to a specific direction from leads 20 to enhance therapy efficacy and reduce possible adverse side effects from stimulating a large volume of tissue. In some examples, outer housing 34 of IMD 16 may include one or more stimulation and/or sensing electrodes. For example, housing 34 can comprise an electrically conductive material that is exposed to tissue of patient 12 when IMD 16 is implanted in patient 12, or an electrode can be attached to housing 34. In other examples, one or both leads 20 may have a shape other than elongated cylinders as shown in FIG. 1. For example, leads 20 may be paddle leads, spherical leads, bendable leads, or any other type of shape effective in treating patient 12.

External programmer 14 is configured to wirelessly communicate with IMD 16 as needed to provide or retrieve therapy information. Programmer 14 is an external computing device that the user, e.g., the clinician and/or patient 12, may use to communicate with IMD 16. For example, programmer 14 may be a clinician programmer that the clinician uses to communicate with IMD 16 and program one or more therapy programs for IMD 16. Alternatively, programmer 14 may be a patient programmer that allows patient 12 to select programs and/or view and modify therapy parameters. The clinician programmer may include more programming features than the patient programmer. In other words, more complex or sensitive tasks may only be allowed by the clinician programmer to prevent an untrained patient from making undesired changes to IMD 16. Programmer 14 may be a hand-held computing device with a display viewable by the user and an interface for providing input to programmer 14 (i.e., a user input mechanism).

For example, programmer 14 may include a small display screen (e.g., a liquid crystal display (LCD) or a light emitting diode (LED) display) that presents information to the user. In addition, programmer 14 may include a touch screen display, keypad, buttons, a peripheral pointing device or another input mechanism that allows the user to provide input. If programmer 14 includes buttons and a keypad, the buttons may be dedicated to performing a certain function, e.g., a power button, or the buttons and the keypad may be soft keys that change in function depending upon the section of the user interface currently viewed by the user. In some examples, the screen (not shown) of programmer 14 may be a touch screen that allows the user to provide input directly to the user interface shown on the display. The user may use a stylus or their finger to provide input to the display.

In other examples, programmer 14 may be a larger workstation or a separate application within another multi-function device, rather than a dedicated computing device. For example, the multi-function device may be a notebook computer, tablet computer, workstation, cellular phone, personal digital assistant or another computing device that may run an application that enables the computing device to operate as a secure medical device programmer 14. A wireless adapter coupled to the computing device may enable secure communication between the computing device and IMD 16.

When programmer 14 is configured for use by the clinician, programmer 14 may be used to transmit initial programming information to IMD 16. This initial information may include hardware information, such as the type of leads 20, the arrangement of electrodes 24, 26 on leads 20, the position of leads 20 within brain 28, initial programs defining therapy parameter values, and any other information that may be useful for programming into IMD 16. Programmer 14 may also be capable of completing functional tests (e.g., measuring the impedance of electrodes 24, 26 of leads 20).

The clinician may also store therapy programs within IMD 16 with the aid of programmer 14. During a programming session, the clinician may determine one or more therapy programs that may provide efficacious therapy to patient 12 to address symptoms associated with the seizure disorder (or other patient condition). During the programming session, patient 12 may provide feedback to the clinician as to the efficacy of the specific program being evaluated or the clinician may evaluate the efficacy based on one or more physiological parameters of patient (e.g., heart rate, respiratory rate or muscle activity).

Programmer 14 may also assist the clinician in the analysis of fault information of the type described herein. For example, sensed signals sensed by lead 20 and electrodes 24, 26 may be transmitted via telemetry transmissions to programmer 14 for storage and analysis. Programmer 14 may display portions of the sensed waveforms for viewing by a user. In some examples, multiple types of data may be displayed at once. For instance, in systems in which a stream of impedance values are obtained in real- or substantially real-time while a patient is moving, this stream of impedance values may be displayed along a common timeline that is annotated with times of patient motion and that further correlates a sensed LFP or some other sensed physiological signal with the impedance data. Such a display may show how periodic "blips" that appear in the waveform are time-correlated with out-of-range impedance values, thereby confirming that a failure within a system component is resulting in signal characteristics within the sensed physiological signal.

Other types of interfaces may be provided, such as an interface to display a waveform representative of delivered stimulation at a second location that is time-correlated with an associated portion of a sensed signal that is sensed at a time during or somewhat after, the stimulation. The sensed signal may be overlaid in one example with a baseline signal to allow for easy comparison between the two. This may allow a clinician to determine the likelihood of a fault within the system.

Programmer 14 may also be configured for use by patient 12 in some examples. When configured as a patient programmer, programmer 14 may have limited functionality (compared to a clinician programmer) in order to prevent patient 12 from altering critical functions of IMD 16 or applications that may be detrimental to patient 12. In this manner, programmer 14 may only allow patient 12 to adjust values for certain therapy parameters or set an available range of values for a particular therapy parameter.

Whether programmer 14 is configured for clinician or patient use, programmer 14 is configured to communicate to IMD 16 and, optionally, another computing device, via wireless communication. Programmer 14, for example, may be configured to communicate via wireless communication with IMD 16 using radio frequency (RF) telemetry techniques known in the art. Programmer 14 may also communicate with another programmer or computing device via a wired or wireless connection using any of a variety of local wireless communication techniques, such as RF communication according to the 802.11 or Bluetooth specification sets, infrared (IR) communication according to the IRDA specification set, or other standard or proprietary telemetry protocols. Programmer 14 may also communicate with other programming or computing devices via exchange of removable media, such as magnetic or optical disks, memory cards or memory sticks. Further, programmer 14 may communicate with IMD 16 and another programmer via remote telemetry techniques known in the art, communicating via a local area network (LAN), wide area network (WAN), public switched telephone network (PSTN), or cellular telephone network, for example.

Therapy system 10 may be implemented to provide chronic stimulation therapy to patient 12 over the course of several months or years. However, system 10 may also be employed on a trial basis to evaluate therapy before committing to full implantation. If implemented temporarily, some components of system 10 may not be implanted within patient 12. For example, patient 12 may be fitted with an external medical device, such as a trial stimulator, rather than IMD 16. The external medical device may be coupled to percutaneous leads or to implanted leads via a percutaneous extension. If the trial stimulator indicates DBS system 10 provides effective treatment to patient 12, the clinician may implant a chronic stimulator within patient 12 for relatively long-term treatment. In addition, the trial stimulator can be used to select a target therapy delivery site for patient 12.

Figure 2:
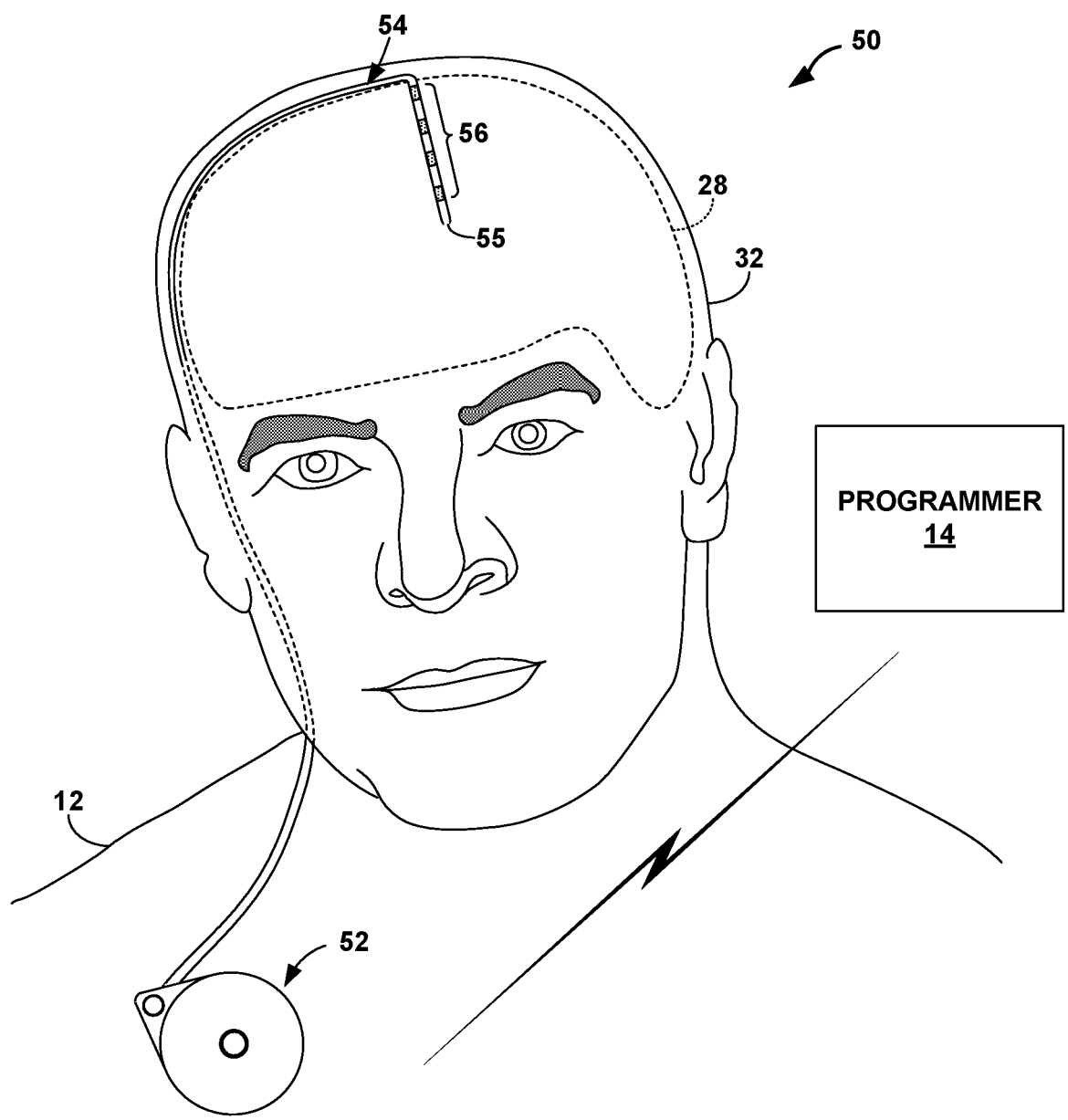
FIG. 2 is a conceptual diagram illustrating an example therapy system configured to deliver a therapeutic agent to a tissue site within a brain of a patient.

FIG. 2 is a conceptual diagram illustrating an example therapy system 50 for delivery of a therapeutic agent to a tissue site within brain 28 of a patient 12. Therapy system 50 includes IMD 52 and catheter 54, which includes a plurality of electrodes 56 for sensing one or more bioelectrical brain signals within brain 28 of patient 12. IMD 52 is configured to deliver at least one therapeutic agent, such as a pharmaceutical agent (e.g., anti-seizure medication), anti-inflammatory agent, gene therapy agent, or the like, to a target tissue site within brain 28 of patient 12 via catheter 54, which is in fluid communication with IMD 52. Catheter 54 may be coupled to IMD 52 either directly or with the aid of an extension (not shown in FIG. 1).

In some examples, IMD 52 includes a fluid pump or another device that delivers a therapeutic agent in some metered or other desired flow dosage to the therapy site within patient 12 from a reservoir within IMD 52 via catheter 54. For treatment of a seizure disorder, drug therapy may be intended to minimize the severity, duration or frequency of seizures. Examples of pharmaceutical agents that IMD 52 may deliver to patient 12 to manage a seizure include, but are not limited to, adenosine, lorazepam, carbamazepine, oxcarbazepine, valproate, divalproex sodium, acetazolamide, diazepam, phenytoin, phenytoin sodium, felbamate, tiagabine, levetiracetam, clonazepam, lamotrigine, primidone, gabapentin, phenobarbital, topiramate, clorazepate, ethosuximide, and zonisamide. In other examples, IMD 52 delivers a therapeutic agent to tissue sites within patient 12 other than brain 28. Electrodes 56 are configured to sense bioelectrical signals within brain 28 of patient 12 to allow system 50 to monitor one or more bioelectrical brain signals within brain 28. In some examples, electrodes 56 may be substantially similar to one or more of electrodes 24, 26 (FIG. 1). Although FIG. 2 illustrates catheter 54 including four sense electrodes 56, in other examples, a catheter may include any suitable number of sense electrodes, such as one, two, three or greater than four. In addition, although sense electrodes 56 are located proximal to the fluid delivery port 55 of catheter 54 in the example shown in FIG. 2, in other examples, one or more of sense electrodes 56 may be distal to fluid delivery port 55 of catheter 54. Catheter 54 may include more than one fluid delivery port. Thus, in some examples, one or more sense electrodes 56 may be located between fluid delivery ports of catheter 54.

In some embodiments, another therapy delivery device, such as a lead or another catheter carrying electrodes, may be located at a different region of the patient's body that is remote from fluid delivery port 55. This second therapy delivery device may sense a response to delivery of a therapeutic agent by catheter 54 and/or delivery of electrical stimulation by electrodes 56. The sensing of the response may be similar to sensing of the evoked response caused by delivery of electrical stimulation as discussed above. Characteristics of this sensed response may be used to determine whether a fault may exist in the system using techniques similar to those discussed above in regards to FIG. 1. Thus, therapeutic stimulation may comprise electrical stimulation, stimulation by a therapeutic agent, or some other type of stimulation, such as optical or ultrasound stimulation. FIG. 3 is functional block diagram illustrating components of IMD 16. In the example shown in FIG. 3, IMD 16 includes processor 60, memory 62, stimulation generator 64, sensing module 66, switch module 68, telemetry module 70, and power source 72. Memory 62 may include any volatile or non-volatile media, such as a random access memory (RAM), read only memory (ROM), non-volatile RAM (NVRAM), electrically erasable programmable ROM (EEPROM), flash memory, and the like. Memory 62 may store computer-readable instructions that, when executed by processor 60, cause IMD 16 to perform various functions described herein.

In the example shown in FIG. 3, memory 62 stores therapy programs 74 and operating instructions 78, which may be stored in separate memories within memory 62 or separate areas within memory 62. Each stored therapy program 74 defines a particular program of therapy in terms of respective values for electrical stimulation parameters, such as a stimulation electrode combination, electrode polarity, current or voltage amplitude, and, if stimulation generator 64 generates and delivers stimulation pulses, the therapy programs may define values for a pulse width, and pulse rate of a stimulation signal. In examples when IMD 16 delivers electrical stimulation therapy on a cyclic basis (as compared to a substantially continuous basis), memory 62 stores, e.g., as part of therapy programs 74, cycle parameter information, such as, on cycle time duration and off cycle duration. In some examples, the therapy programs may be stored as a therapy group, which defines a set of therapy programs with which stimulation may be generated. The stimulation signals defined by the therapy programs of the therapy group may be delivered together on an overlapping or non-overlapping (e.g., time-interleaved) basis.

Operating instructions 78 guide general operation of IMD 16 under control of processor 60 and may comprise instructions to control how signals are sensed from electrodes 24, 26, and how the signals are thereafter processed to determine fault detection, and so on.

In some example, processor 60 and/or a processor of programmer 14 may perform the steps to perform the methods disclosed herein, such that these methods may be partially, or fully, automated. Thus, while in some cases, analysis of fault data may be performed in whole or in part, by a clinician, in other cases, such analysis may be performed according to techniques described herein in whole or in part may one or more processors including processor 60 of IMD 16.

Sensing information 76 is also stored by memory 62. This information may include evoked potentials (EPs) 76A resulting from sensing the result of delivered stimulation, and may include information pertaining to whether or not characteristics of expected evoked potentials (or evoked responses) are present within the sensed signals. The evoked potentials could be LFP signals, or any other type of signals that indicate the response to stimulation. Sensing information 76 may further include motion data 76B, which is data that may result from sensing during periods of patient motion and may include information pertaining to whether a motion artifact is reflected in the sensed signal. Such information may further include data pertaining to when and what types of motion were associated with the sensed data. Sensing information 76 may further include ECG data 76C that may be sensed to determine whether an ECG artifact is present in a sensed signal, such as a sensed brain signal. These are examples of data only, and other artifact data may be stored instead of, or in addition to, the illustrated data, including artifact data related to tapping on the housing of the IMD 16.

Memory 62 may also store baselines 77, which may provide baseline evoked response signals, and further may provide baseline signals for structures in which electrodes 24, 26 are located, such as baseline signals for the AN, HC, and STN. Such signals may be indicative of those signals expected to be received in the corresponding structures in the absence of an evoked potential signal. These signals may be compared, for instance, to sensed signals to determine whether, in the absence of an evoked potential signal, an expected signal is being received on a particular electrode combination. This may be useful in further performing fault isolation using techniques described herein. When used together, these two types of baseline signals may be used to determine whether a fault is likely in a stimulation or a sensing path as discussed above.

Baselines 77 may also include other baseline signals, such as baseline signals expected to be obtained during a particular patient motion in the absence of a system fault. In some examples, these types of baseline signals are the same as the baseline signals obtained for the various brain structures (AN, HC, STN, etc.) in the absence of an evoked potential. That is, if the motion does not have any effect on the sensed brain signal in the absence of the fault, there is no need for this additional baseline signal, and the baseline signals discussed above may be used as a comparison to those obtained during motion.

Memory may also store templates and thresholds 76D that may be used to compare to evoked potential signals. Templates might provide the waveform shape or a signature expected to be associated with a particular type of fault. If template matching techniques indicate this template does favorably compare, or "match" with a sensed signal that is obtained during motion, a fault may exist within the system.

Template and threshold data 76D may further include thresholds. In one example, a threshold may indicate an upper or lower bound of the amplitude of a signal (either in the time- or frequency-domain) that would be expected to be sensed in the absence of a system fault, such as a voltage, current, or power-level amplitude. In some cases, the threshold may indicate an upper or lower bound of a value determined as a ratio between an amplitude of the sensed signal to that of the baseline signal. In some cases, the threshold may indicate a power-level of a frequency domain signal, or a duration (e.g., width of a signal characteristic) in a time-domain signal. Other types of thresholds are possible within the scope of this disclosure. Also shown in FIG. 3 is stimulation generator 64. Under the control of processor 60, stimulation generator 64 generates stimulation signals for delivery to patient 12 via selected combinations of electrodes 24, 26. In some examples, during therapy delivery to manage a disorder, stimulation generator 64 generates and delivers stimulation signals to one or more target regions of brain 28 (FIG. 1), e.g., the AN, of patient 12 via a select combination of electrodes 24, 26 (referred to herein as a stimulation electrode combination) where the stimulation signals have a frequency in a range of about 1 Hertz (Hz) to about 10,000 Hz (or in some cases, between 2 Hz and 1200 Hz), a voltage of about 0.1 volts to about 10.5 volts, and a pulse width of about 60 microseconds to about 450 microseconds. In some examples, the stimulation signals have a frequency of 120 Hz, a voltage of about 4 volts, and a pulse width of about 100 microseconds. In addition, in some examples, the stimulation signals have a frequency of 145 Hz, a voltage of about 5 volts, and a pulse width of about 145 microseconds.

In some examples, stimulation is delivered to generate an evoked potential that can be associated with a portion of a sensed signal that is sensed at a location other than that at which the stimulation was delivered. The associated portion of the sensed signal may then be used to diagnose a system fault. The stimulation signals used for this purpose may be low frequency stimulation signals, such a stimulation having a frequency of between 2 and 10 Hz.

As a specific example, stimulus frequencies below approximately 40 Hz (such as, e.g., between approximately 1 Hz and 40 Hz, or between approximately 2 Hz and 10 Hz, may be delivered to the AN to evoke (or to try to evoke) a potential in the HC or vice versa. Any evoked potential may be sensed to determine whether the sensed signal, or a portion of the sensed signal that has been associated with the stimulation, exhibits an expected morpholophy, amplitude, and so on. This may be done by comparing the associated portion of the sensed signal to a baseline signal representing the shape, amplitude, duration, and so on of a signal that would be sensed if no fault existed within the system, as discussed above. In other examples, the associated portion of the sensed signal may be analyzed to determine whether it meets one or more predetermined criteria, such as whether the portion of the signal has a characteristic having an amplitude, width, frequency, a power-level in one or more frequency bands, or some other predetermined characteristic of at least a predetermined threshold, a characteristic with a time-duration that meets some length criteria, a power level in one or more frequency bands that is within some predetermined amplitude range or is above a predetermined power level, a waveform shape that substantially matches some expected shape, and so on. The predetermined criteria may be determined using template-matching techniques.

Processor 60 may include any one or more of a microprocessor, a controller, a digital signal processor (DSP), an application specific integrated circuit (ASIC), a field-programmable gate array (FPGA), discrete logic circuitry, and the functions attributed to processor 60 herein may be embodied as firmware, hardware, software or any combination thereof. Processor 60 is configured to control stimulation generator 64 according to therapy programs 74 stored in memory 62 to apply particular stimulation parameter values specified by one or more programs, such as amplitude, pulse width, and pulse rate.

In the example shown in FIG. 3, the set of electrodes 24 of lead 20A includes electrodes 24A, 24B, 24C, and 24D, and the set of electrodes 26 of lead 20B includes electrodes 26A, 26B, 26C, and 26D. Processor 60 may control switch module 68 to apply the stimulation signals generated by stimulation generator 64 to selected combinations of electrodes 24, 26. In particular, switch module 68 may couple stimulation signals to selected conductors within leads 20, which, in turn, deliver the stimulation signals across the electrodes 24, 26 of the selected stimulation electrode combination. Switch module 68 may be a switch array, switch matrix, multiplexer, or any other type of switching module configured to selectively couple stimulation energy to selected electrodes 24, 26 and to selectively sense bioelectrical brain signals with selected electrodes 24, 26. Hence, stimulation generator 64 is coupled to electrodes 24, 26 via switch module 68 and conductors within leads 20. In some examples, however, IMD 16 does not include switch module 68.

Stimulation generator 64 may be a single channel or multi-channel stimulation generator. In particular, stimulation generator 64 may be capable of delivering, a single stimulation pulse, multiple stimulation pulses or continuous signal at a given time via a single electrode combination or multiple stimulation pulses at a given time via multiple electrode combinations. In some examples, however, stimulation generator 64 and switch module 68 may be configured to deliver multiple channels on a time-interleaved basis. For example, switch module 68 may serve to time divide the output of stimulation generator 64 across different electrode combinations at different times to deliver multiple programs or channels of stimulation energy to patient 12.

Sensing module 66 is configured to sense bioelectrical brain signals of patient 12 via a sense electrode combination, which can include a selected subset of electrodes 24, 26 or with one or more electrodes 24, 26 and at least a portion of a conductive outer housing 34 of IMD 16, an electrode on an outer housing of IMD 16 or another reference. Processor 60 may control switch module 68 to electrically connect sensing module 66 to selected electrodes 24, 26. In this way, sensing module 66 may selectively sense bioelectrical brain signals with different combinations of electrodes 24, 26 (and/or a reference other than an electrode 24, 26).

In some examples, processor 60 may select an electrode combination for delivering efficacious stimulation therapy to patient 12 based on one or more characteristics of the bioelectrical brain signals monitored by sensing module 66. In addition, in some examples, a diagnostic method may be performed to determine the possible presence of a fault in the system based on characteristics of the bioelectrical brain signals monitored by sensing module 66. Although sensing module 66 is incorporated into a common outer housing 34 with stimulation generator 64 and processor 60 in FIG. 3, in other examples, sensing module 66 is in a separate outer housing from outer housing 34 of IMD 16 and communicates with processor 60 via wired or wireless communication techniques.

Processor 60 may also be configured to control stimulation generator 64 to deliver stimulation to diagnose a potential system fault and to further control sensing module 66 to sense a signal at the same time as, and/or sometime thereafter, to determine whether an evoked response was determined based on the delivered stimulation, and if so, whether it was degraded (e.g., had a reduced amplitude, duration, an unexpected morphology, etc.).

Processor 60 may, in some cases, receive a signal from sensing module 68, associate a portion of that sensed signal with a stimulation signal delivered by stimulation generator 64, retrieve a template and compare the portion of the sensed signal to the template. The result of the comparison may then be used to determine whether a fault may exist in a component in the system. Instructions for controlling these functions of processor 60 may be stored with memory 62 as operating instructions 77. In some examples, the sensed evoked potentials may be stored within memory 62 as EPs 76A. These sensed evoked potentials may be transferred to an external device such as programmer 14 via telemetry module 70 for analysis by programmer 14 or some other external device to determine whether a fault may exist in the system.

In other examples, processor 60 may control sensing module 66 to sense a signal that may contain an artifact introduced based on some activity in, or a signal introduced into, another portion of the patient's body remote from the sensing location (e.g. remote from a location in the brain.) For instance, processor 60 may control sensing module 66 to sense a signal during, and/or sometime just after, the patient undergoes movement. Such movement may also move, or put strain on, a system component. As one example, turning or nodding of the patient's head may result in stresses and/or motion placed on a lead 20A, 20B and/or a lead extension that extends along the side of a patient's neck. As another example, a clinician may perform "tapping" on the can of IMD 16 to introduce a vibrational signal into the patient's body. As another example, the beating of the patient's heart likewise introduces a signal into the patient's body.

In any of the foregoing cases, processor 60 may control sensing module 66 to sense a signal at the same time, and/or a predetermined time delay after, motion, vibrational, or other types of signals are introduced into the body. Whether, and how, artifacts from these introduced signals are present in the sensed signal may be useful in diagnosing a potential system fault. Processor 60 may control sensing module 66 based on a command received from programmer 14 via telemetry module 70, for instance, or from another signal. In some cases, a clinician may "tap" on the can of IMD 16 to communicate that processor should initiate sensing by sensing module 86. For instance, the clinician may tap on the can of IMD 16 while, or just before, the patient is instructed to turn his/her head. Such tapping may be detected by an on-board sensor such as an accelerometer (not shown), which triggers processor 60 to initiate the sensing operation via sensing module 66. The sensed signal or a portion thereof may be associated with the signal being introduced at the second location (i.e., the motion artifact being introduced at the point of the motion, which is in the patient's neck region.

Telemetry module 70 supports wireless communication between IMD 16 and an external programmer 14 or another computing device under the control of processor 60. Processor 60 of IMD 16 may receive, as updates to programs, values for various stimulation parameters such as amplitude and electrode combination, from programmer 14 via telemetry module 70. The updates to the therapy programs may be stored within therapy programs 74 portion of memory 62. Telemetry module 70 in IMD 16, as well as telemetry modules in other devices and systems described herein, such as programmer 14, may accomplish communication by RF communication techniques. In addition, telemetry module 70 may communicate with external medical device programmer 14 via proximal inductive interaction of IMD 16 with programmer 14. Accordingly, telemetry module 70 may send information to external programmer 14 on a continuous basis, at periodic intervals, or upon request from IMD 16 or programmer 14. For example, processor 60 may transmit brain state information 76 to programmer 14 via telemetry module 70.

Power source 72 is configured to deliver operating power to various components of IMD 16. Power source 72 may include, for example, a small rechargeable or non-rechargeable battery and a power generation circuit to produce the operating power. Recharging may be accomplished through proximal inductive interaction between an external charger and an inductive charging coil within IMD 16. In some examples, power requirements may be small enough to allow IMD 16 to utilize patient motion and implement a kinetic energy-scavenging device to trickle charge a rechargeable battery. In other examples, traditional batteries may be used for a limited period of time.

Figure 4:
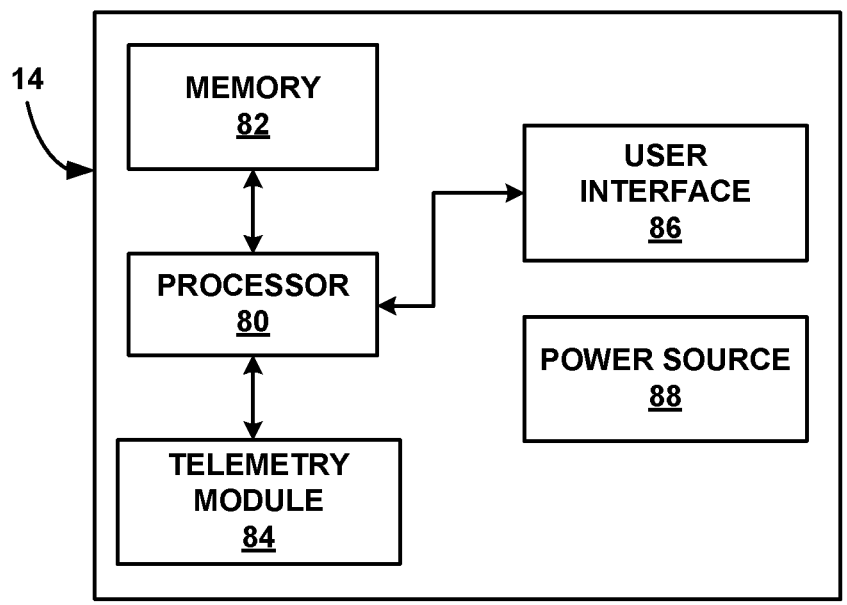
FIG. 4 is a functional block diagram illustrating components of an example medical device programmer.

FIG. 4 is a functional block diagram illustrating components of an example medical device programmer 14 (FIG. 1). Programmer 14 includes processor 80, memory 82, telemetry module 84, user interface 86, and power source 88. Processor 80 controls user interface 86 and telemetry module 84, and stores and retrieves information and instructions to and from memory 82. Programmer 14 may be configured for use as a clinician programmer or a patient programmer. Processor 80 may comprise any combination of one or more processors including one or more microprocessors, DSPs, ASICs, FPGAs, or other equivalent integrated or discrete logic circuitry. Accordingly, processor 80 may include any suitable structure, whether in hardware, software, firmware, or any combination thereof, to perform the functions ascribed herein to processor 80. Processor 80 may operate in conjunction with processor 60 to perform analysis on an associated portion of a sensed signal or may operate alone to perform such analysis to determine whether a system fault has occurred.

A user, such as a clinician or patient 12, may interact with programmer 14 through user interface 86. User interface 86 includes a display (not shown), such as a LCD or LED display or other type of screen, to present information related to the therapy, such as information related to bioelectrical signals sensed via a plurality of sense electrode combinations in response to the delivery of stimulation to brain 28. In addition, user interface 86 may include an input mechanism to receive input from the user. The input mechanisms may include, for example, buttons, a keypad (e.g., an alphanumeric keypad), a peripheral pointing device or another input mechanism that allows the user to navigate through user interfaces presented by processor 80 of programmer 14 and provide input.

As discussed above, if programmer 14 includes buttons and a keypad, the buttons may be dedicated to performing a certain function, or the buttons and the keypad may be soft keys that change function depending upon the section of the user interface currently viewed by the user. In addition, or instead, the screen (not shown) of programmer 14 may be a touch screen that allows the user to provide input directly to the user interface shown on the display. The user may use a stylus or their finger to provide input to the display. In other examples, user interface 86 also includes audio circuitry for providing audible instructions or sounds to patient 12 and/or receiving voice commands from patient 12, which may be useful if patient 12 has limited motor functions. Patient 12, a clinician or another user may also interact with programmer 14 to manually select therapy programs, generate new therapy programs, modify therapy programs through individual or global adjustments, and transmit the new programs to IMD 16.

In one example, as user may provide input via one or more of the input mechanisms to indicate that some signal is being introduced into the system. For instance, the user may push a button, speak a command, perform some tactile function on a pressure sensitive screen, and so on, to communicate that the patient has started undergoing motion. This information may be communicated to IMD 16 so that processor 60 may control sensing module 66 to sense corresponding signals. The corresponding signals may be temporally associated with the introduced signals and then associated portions of the sensed signals may be analyzed (e.g., by processor 60 and/or processor 80) to determine whether they indicate that a potential failure or component fault may exist within the system. In some examples, at least some of the control of stimulation delivery by IMD 16 may be implemented by processor 80 of programmer 14. For example, in some examples, processor 80 may control stimulation generator 64 of IMD 16 to generate and deliver electrical stimulation to a plurality of areas of AN of brain 28 and may further control sensing module 66 to sense a bioelectrical brain signal within brain 28 that is indicative of the brain activity level within the HC of brain 28 and that may further be used to determine whether a fault exists within the system. In other examples, stimulation may be delivered to the HC and sensed in the AN, or stimulation may be delivered to any first location that is functionally connected to a second location such that stimulation at the first location will evoke a response in the second location.

Memory 82 may include instructions for operating user interface 86, and telemetry module 84, and for managing power source 88. Memory 82 may also store any therapy data retrieved from IMD 16, such as, but not limited to, brain activity information.

Operating instructions may guide general operation of programmer 14 under control of processor 80 and may comprise instructions to control how signals that are sensed from electrodes 24, 26 of IMD 16 are processed to determine fault detection. In some example, processor 80 of programmer 14, alone or with processor 60 of IMD 16, may perform the steps to perform the methods disclosed herein, such that these methods may be partially, or fully, automated. Thus, while in some cases, analysis of fault data may be performed in whole or in part, by a clinician, in other cases, such analysis may be performed according to techniques described herein in whole or in part may one or more processors including processor 80 of programmer 14.

Memory 82 may store evoked potentials resulting from sensing by IMD 16 the result of delivered stimulation, and may include information pertaining to whether or not characteristics of expected evoked potentials (or evoked responses) are present within the sensed signals.

The evoked potentials could be LFP signals, or any other type of signals that indicate the response to stimulation. This information may further include motion date sensed by IMD 16 which is data that may result from sensing during periods of patient motion and may include information pertaining to whether a motion artifact is reflected in the sensed signal. Such information may further include data pertaining to when and what types of motion were associated with the sensed data. Other information stored by memory 82 may include ECG data that may be sensed by IMD 16 to determine whether an ECG artifact is present in a sensed signal, such as a sensed brain signal. Other artifact data may be stored instead of, or in addition to, ECG artifact data such as data related to tapping on the housing of the IMD 16.

Memory 82 may also store baselines which provide baseline evoked response signals and/or baseline signals sensed during motion. Other baseline signals may include baseline signals when no stimulation is present. Different signals may be provided for different anatomical structures in some cases and may be indicative of those signals expected to be received for the corresponding structures in the absence of an evoked potential signal.

These signals may be compared, for instance, to sensed signals to determine whether in the absence of an evoked potential signal an expected signal is being received on a particular electrode combination. In some cases, different baseline signals may be provided for different electrode combinations, as may be obtained just after implantation of a lead when it is known that no fault is present in the system. Such baseline signals may be used to determine whether a lead or electrode shifted position sometime after the baseline signals was acquired. The various baseline signals may be useful in further performing fault isolation using techniques described herein.

Memory 82 may also store templates and thresholds that are of a type similar to those discussed above in regards to templates and thresholds 76D. Thus, memory 82 may store some or all of the information shown in FIG. 3 in reference to memory 62 instead of, or in addition to, memory 62 of IMD 16 storing this information.

Memory 82 may include any volatile or nonvolatile memory, such as RAM, ROM, EEPROM or flash memory. Memory 82 may also include a removable memory portion that may be used to provide memory updates or increases in memory capacities. A removable memory may also allow sensitive patient data to be removed before programmer 14 is used by a different patient.

Wireless telemetry in programmer 14 may be accomplished by RF communication or proximal inductive interaction of external programmer 14 with IMD 16. This wireless communication is possible through the use of telemetry module 84. Accordingly, telemetry module 84 may be similar to the telemetry module contained within IMD 16. In alternative examples, programmer 14 may be capable of infrared communication or direct communication through a wired connection. In this manner, other external devices may be capable of communicating with programmer 14 without needing to establish a secure wireless connection.

Power source 88 is configured to deliver operating power to the components of programmer 14. Power source 88 may include a battery and a power generation circuit to produce the operating power. In some examples, the battery may be rechargeable to allow extended operation. Recharging may be accomplished by electrically coupling power source 88 to a cradle or plug that is connected to an alternating current (AC) outlet. In addition, recharging may be accomplished through proximal inductive interaction between an external charger and an inductive charging coil within programmer 14. In other examples, traditional batteries (e.g., nickel cadmium or lithium ion batteries) may be used. In addition, programmer 14 may be directly coupled to an alternating current outlet to operate. Power source 88 may include circuitry to monitor power remaining within a battery. In this manner, user interface 86 may provide a current battery level indicator or low battery level indicator when the battery needs to be replaced or recharged. In some cases, power source 88 may be capable of estimating the remaining time of operation using the current battery.

Figure 5:
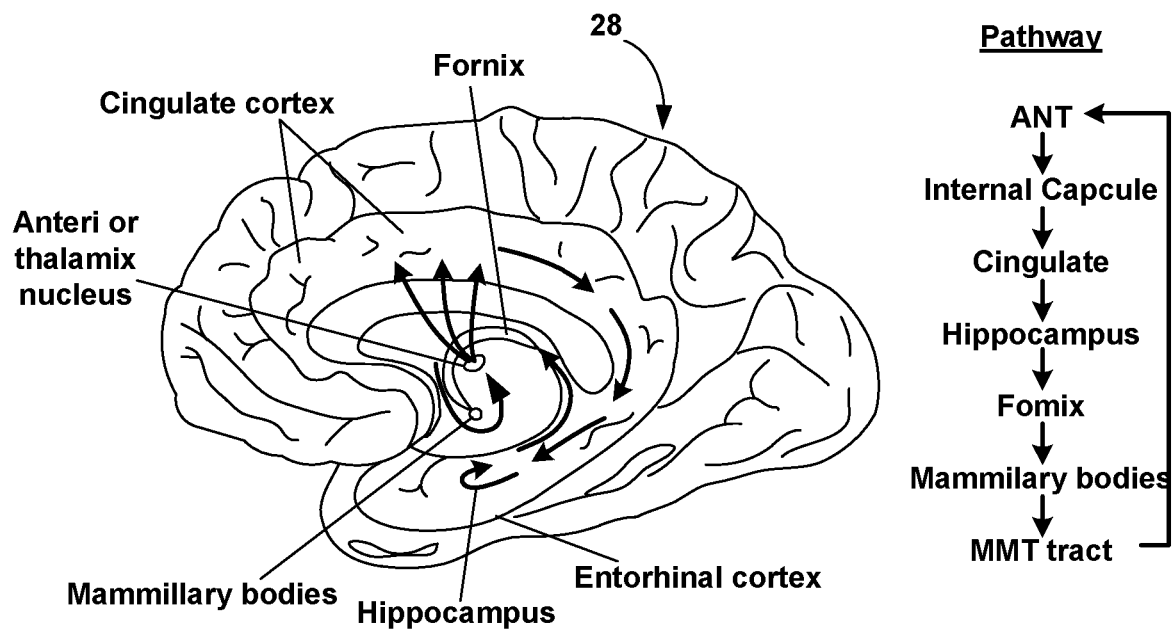
FIG. 5 is a conceptual diagram illustrating example regions of a brain of a patient, and, in particular, regions of the brain included in the Circuit of Papez.

FIG. 5 is a conceptual diagram illustrating example regions of brain 28 of patient 12 and, in particular, regions of brain 28 included in the Circuit of Papez (also referred to as the Papez Circuit). The regions of the brain 28 within the Circuit of Papez are believed to be involved in the generation and spread of seizure activity. The Circuit of Papez is one of the major pathways of the limbic system, and the regions of brain 28 within the Circuit of Papez includes the AN, internal capsule, cingulate (labeled as the cingulate cortex in FIG. 5), HC, fornix, entorhinal cortex, mammillary bodies, and mammillothalamic tract (MMT). The regions of brain 28 within the Circuit of Papez may be considered to be functionally related (also referred to herein as functionally connected), such that activity within one part of the Circuit of Papez may affect activity within another part of the Circuit of Papez. In this way, the delivery of stimulation to one region (e.g., the AN) of the Circuit of Papez may be used to evoke a response, and to affect the brain activity level, within another region of the Circuit of Papez (e.g., the HC). In some examples, electrodes 24, 26 are implanted to deliver electrical stimulation therapy generated via stimulation generator 64 (FIG. 3) to and/or monitor bioelectrical brain signals within one or more regions of the brain in the Circuit of Papez, such as, e.g., the AN, the internal capsule, the cingulate, the fornix, the mammillary bodies, the mammillothalamic tract, and/or HC. In some examples, a disorder of patient 12 may be effectively managed by controlling or influence the brain activity level within one or more regions of the Circuit of Papez. For example, with respect to seizure disorders, therapy may be delivered from IMD 16 to regions within the Circuit of Papez to suppress brain activity (also referred to as cortical activity) within regions of the Circuit of Papez, such as, e.g., the HC. Suppression of brain activity within the HC via therapy may reduce the likelihood of a seizure by patient 12. As another example, for treatment of Alzheimer's disease, therapy may be delivered from IMD 16 to regions within the Circuit of Papez to increase cortical activity within the regions of the Circuit of Papez, such as, e.g., the HC. Increasing brain activity within the HC via therapy may reduce symptoms of Alzheimer's disease, such as memory loss. The delivery of stimulation to the AN of brain 28 may be useful for managing a seizure disorder because the AN is a central site of the Circuit of Papez, and, as a result, stimulating the AN may help target a plurality of seizure foci that may be present in the Circuit of Papez even if the seizure focus is not in the AN. Such a relationship may help minimize the burden on a clinician in identifying a useful target stimulation site by locating the exact seizure focus. This can be referred to as a remote stimulation approach. Moreover, stimulating in the AN can be less invasive to the patient because the leads can be relatively easily implanted in the AN compared to, e.g., the HC, although leads can be implanted in the HC as well in some examples.

For some patients, the HC of brain 28 may be a seizure focus. Accordingly, for at least some of those patients, reducing a brain activity level within the HC may be desirable for managing a seizure disorder. The reduced brain activity level within the HC may help mitigate symptoms of the seizure disorder, such as by lowering likelihood of an occurrence of a seizure, reducing the severity or duration of seizures, and/or reducing the frequency of seizures. Stimulation (or another type of therapy) may be delivered directly to the AN rather than directly to the HC for various reasons, such as to reduce invasiveness of the therapy system.

The level of a functional connection between the AN and the HC may be characterized by the effect of stimulation delivery on an area of the AN on the brain activity level within the HC. As illustrated in FIG. 5, regions within the Circuit of Papez may be connected to one another via neurological pathways such that activity within one region of brain 28 may affect activity within another region of brain 28. As such, electrical stimulation delivered from IMD 16 to a particular region of the Circuit of Papez may influence brain signals, or evoke a response, in one or more other regions of the Circuit of Papez. Due to, for example, the neural pathways between the different parts of brain 28, different areas within a first region (e.g., the AN or the HC) of the Circuit of Papez may have a functional connection to a second region (e.g., the HC or AN) of the Circuit of Papez, such that the effect of the stimulation delivery to the first region may evoke a response to the second region. This response may provide a therapeutic benefit, as described in commonly-assigned U.S. Pat. No. 8,706,181 entitled "Target Therapy Delivery Site Selection", which is assigned to the applicant of the present disclosure and which is incorporated herein by reference in its entirety. Alternatively or additionally, the presence of this functional connection may be used to diagnose system faults, as described herein.

According to one technique, a relatively low frequency stimulation (e.g., 2 Hz-10 Hz) is delivered to an area of the AN of brain 28 and a response may be evoked within the HC. Assuming that the sensing circuit, including the sensing pathway comprising a lead, any lead extension, and the electrodes used for sensing, are properly functioning, a local field potential sensed within the HC may detect the evoked response. As discussed above, this local field potential sensed immediately following the delivery of stimulation to the area of AN can be referred to as the evoked potential (e.g., characterized by the peak amplitude of a sensed bioelectrical brain signal), which results when the brain activity in the thalamus propagates to the HC. Thus, the evoked potential is an excitatory response of the HC to the stimulation delivered to the thalamus; the relatively low frequency stimulation generates a spike in brain activity in the HC. However, if such a response is not present in the sensed signal, or it is present but in a degraded fashion, it may be determined that a fault may have occurred either in the stimulation circuit, including the stimulation pathway such that no stimulation (or stimulation at reduced levels) was delivered to the AN or a fault may exist within the sensing circuit, including the sensing pathway.

The foregoing is merely one example of delivering stimulation to the AN and sensing in the HC, and instead stimulation may be delivered to the HC and sensed in the AN, or delivered at some other site in the circuit of Papez or in some other circuit in the brain and sensed at a location functionally coupled to the location of stimulation delivery.

In some examples, the evoked response (such as the response in the HC of brain 28 of patient 12) can be determined based on at least one characteristic of a sensed bioelectrical brain signal which can be a frequency domain characteristic or a time domain characteristic of the bioelectrical brain signal. Examples of a time domain characteristic include, but are not limited to, a mean, median, instantaneous, peak or lowest amplitude of the bioelectrical brain signal within a predetermined period of time. Examples of a frequency domain characteristic include, but are not limited to, a power level in one or more frequency bands of a bioelectrical brain signal (e.g., sensed within the AN or HC) sensed over a predetermined period of time or a ratio of power levels in at least two frequency bands of the bioelectrical brain signal. In some currently proposed techniques, a target therapeutic stimulation site within the thalamus is selected to be the area of the thalamus that resulted in the greatest evoked potential in the HC (e.g., the brain signal with the greatest average peak amplitude for a time period following the delivery of the stimulation to the thalamus). It is believed that the area of the thalamus that is associated with the greatest evoked potential has the strongest functional connection to the HC, such that delivery of stimulation to the area of the thalamus may provide efficacious stimulation therapy for managing the seizure disorder of patient 12. Such a site selection may also prove beneficial when analyzing faults, since stimulation at this site should, barring the existence of faults, provide a response that is readily apparent in the sensed signal. Example methods for selecting a site for stimulation in one area for sensing in another area of the patient's body are disclosed in U.S. Pat. No. 8,706,181 referenced above and incorporated herein by reference.

Figure 6:
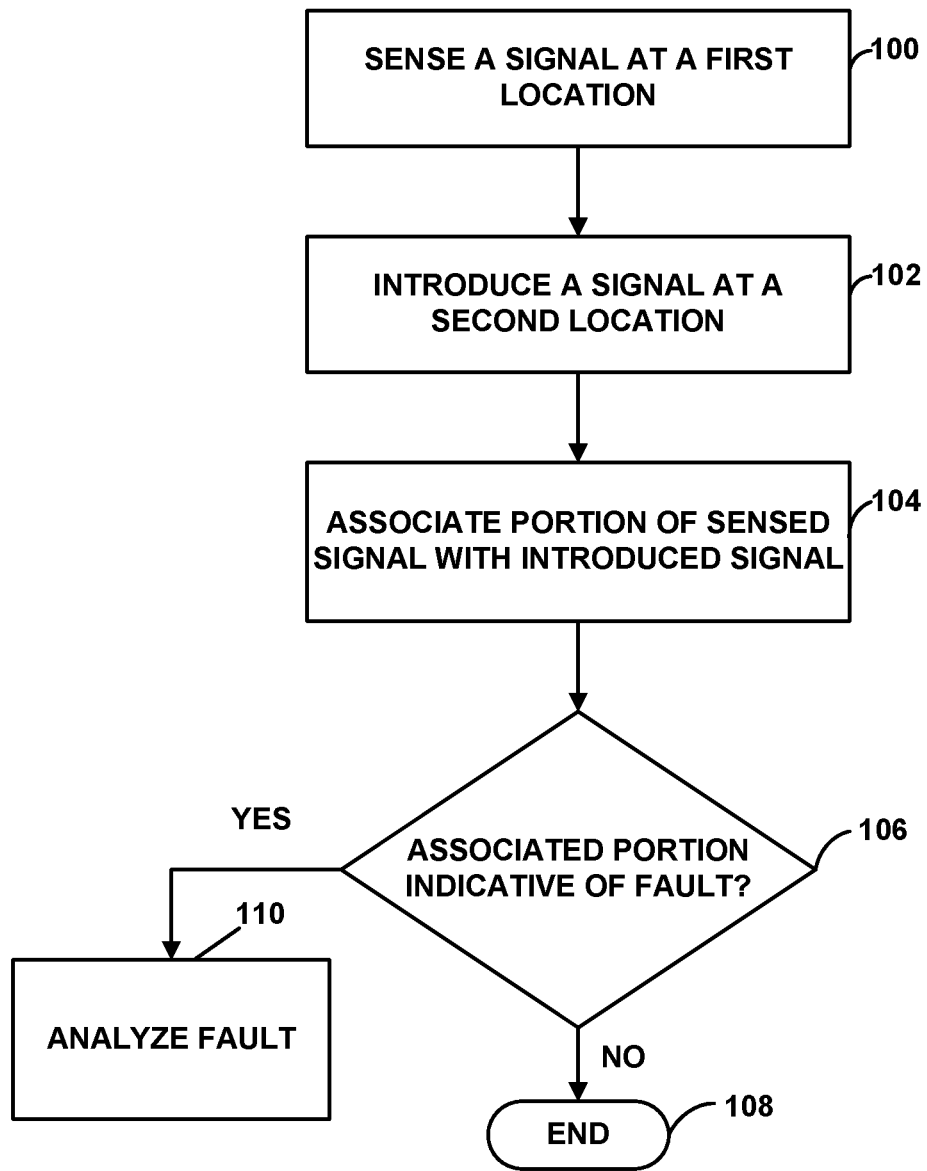
FIG. 6 is a flow diagram illustrating an example technique for using sensed signals to determine whether a potential fault may exist within the system.

FIG. 6 is a flow diagram illustrating an example technique for using sensed signals to determine whether a potential fault may exist within the system. A signal may be sensed at a first location (100). The signal may be an LFP, an EEG and ECoG, a microelectrode recording signal (MER), or some other type of signal sensed by the system. The first location may be a location on the patient's body, such as within brain tissue, on the cortex, within the subgaleal space, on the scalp, or some other location within the body.

A signal may be introduced at a second location different from the first location (102). The introduction of the signal may involve a signal introduced by motion of the patient's body. For instance, the patient may undergo some movement such as head turning, arm swinging, movement of the torso, or some other movement that is performed by the patient. Such motion may be performed at the direction of a clinician for the purpose of diagnosing a potential fault, or may be motion undertaken by the patient for another purpose. In one example, the motion may be physiological activity that is not consciously controlled by the patient, such as beating of the patient's heart. In still another example, the signal is an acoustic signal resulting from tapping on the housing of IMD 16 or otherwise manipulating a component of the system such as palpating, moving, pushing on, and so on, a lead or lead extension that is under the skin of the patient.

In any event, the second location of the body at which the signal is introduced may be a portion of the body undergoing or affected by the motion. The second location may be the neck, the arms, the torso, the beating heart, and so. The signal may be a vibrational signal, an acoustic signal (e.g., introduced by a heartbeat), a pressure signal, a signal resulting from stresses and strains placed on a lead, lead extension, or some other component in the system, or some other signal introduced at the second location. The signal may be introduced before, during, or after sensing at the first location has commenced. A portion of the sensed signal may be associated with the introduced signal (104).

This may involve determining a portion of the sensed signal that is contemporaneous with the introduced signal. For instance, a portion of the sensed signal that was sensed during, a predetermined time within, or a predetermined time after, the introduction of the signal at the second location may be associated with the introduced signal. In some cases, this may involve providing, by a user of the system, some indication that motion has been commenced, is underway, or has just stopped. Such an indication may involve providing input to the system that can be used by the system to timestamp or otherwise annotate the sensed signal. Input may be provided via a patient or clinician programmer, tapping on a housing of the IMD 16 in a way that can be sensed by an on-board sensor such as an accelerometer, or using some other input mechanism.

In some cases, the association may be performed automatically. For instance, when a portion of the sensed signal is determined to have a particular characteristic that is known to originate outside the first location, the system may automatically perform the association. Such a characteristic may be a signal amplitude that is above some threshold that is known to be expected in a signal sensed from brain tissue. As other examples, the characteristic may be a frequency, a waveform morphology, a pattern or timing of the reoccurrence of a characteristic that is not otherwise expected to manifest itself in the tissue. Detection of these types of characteristics may cause the system to automatically associate the sensed signal with a signal introduced at a second location.

The portion of sensed signal that has been associated with the introduced signal may be identified in various ways. In some cases, the sensed signal may be stored within a memory of IMD 16 or programmer 14, with the associated portion of this signal being stored along with timestamps or other annotations. In some cases, only the associated portions may be stored, with other portions of the signal being discarded or stored in another location of memory. The associated portions may be stored along with some indication that describes the introduced signal. The description may involve a recording of the introduced signal recorded at the second location (e.g., via electrodes on the patient's body), a description of the signal provided by a user, and so on. The sensed signal, or an associated portion thereof, which is stored for later analysis may include "raw" data such as data that is converted from an analog to a digital signal but which is otherwise unprocessed, or a signal that has undergone A/D conversion and has further undergone some other type of processing, such as some filtering to remove some unwanted noise. Such signal data may be stored within memory 62 of IMD 16 and/or memory 82 of programmer 14.

After a portion of the sensed signal is associated with the introduced signal, it may be determined if the associated portion is indicative of a fault (106). Such analysis may involve comparing a time domain feature of the signal, such as an amplitude, waveform shape, the rhythmic nature of the signal (e.g., whether spikes or other characteristics are known to be occurring at a frequency of the introduced signal), and so on. In some cases, a signal may be compared to one or more thresholds to determine whether the signal is outside of expected ranges. For instance, a sensed signal sensed within brain tissue that has an amplitude within a millivolt range may be known to be outside of expected physiological signals, since physiological signals originating in brain tissue are expected to be in a microvolt range. This may indicate the presence of a fault. As another example, spikes in the signal occurring at a regular interval that is known to correspond to a frequency of patient motion, frequency of tapping on the "can" of IMD 16, or the frequency of the patient's beating heart may be determined to be the result of an introduced signal. Typically such signals would not be sensed within brain tissue by leads implanted within the brain. However, the occurrence of faults such as leakage pathways that allow for fluid ingress at connection points in the system may allow such signals to be sensed by leads, obscuring any signal that would otherwise be sensed within the tissue. The detection of this type of signal may be an indication that a fault may have occurred within the system. Baseline signals may be used to determine whether a fault likely exists. As an example, an associated portion of the sensed signal may be compared to a baseline signal that reflects how the introduced signal is expected to look in a system without faults. Such a baseline signal may reflect the complete absence of any artifact in the signal if, when no fault is present, the motion is not expected to affect the sensed signal. In another example, the baseline signal may reflect low levels of the artifact. This baseline signal may be obtained when motion is introduced into the system when a fault is known to be absent. In some cases, the baseline signal may be patient-specific in that it is derived from signals sensed by the system currently being verified when it was known that the system way free of faults. In this case, a match between the sensed signal and the baseline indicates that the comparison does not point to the likely existence of a fault in the system.

According to another scenario, a template may reflect how the introduced signal might be expected to look if a fault likely exists in the system. Such a template may be obtained by sensing a signal in a system known to have a fault when the particular type of motion is introduced into the system. In this case, the template may, for instance, include one or more noise "spikes" or other disturbances that are likely to occur when the predetermined type of motion is introduced when a fault is present. Different templates may be provided for different types of motion, different system components and configurations, and so on.

Based on any combination of techniques described herein, if it is determined that a sensed signal is not likely indicative of a fault (108), this information may be provided to a user, as via information presented on a display of a user interface of programmer 14. If, on the other hand, a sensed signal is likely indicative of a fault (110), additional analysis may be performed. In some cases, this may be accomplished using different templates that may be developed for different fault types. Such templates could be determining by recording signals in a system known to have the particular type of failure. As an example, in a system known to have an IMD header block that is allowing fluid ingress, a signal may be recorded by a lead implanted in the brain while the patient turns their head. Any number of fault types may be used to develop respective artifact templates.

In some cases, a templates may be derived based on a combination of one or more factors, including fault types, the system configuration (i.e., types of components in use in the system), location of the sensing lead, the type of artifact that is introduced into the system and/or any other aspect that would affect the template. The templates may be derived by sensing a signal in a system having a known type of fault, and further having the type of configuration, and experiencing the type of artifact that is associated with the template.

During use, a particular set of templates may be selected for comparison to a sensed signal based on a type of artifact being analyzed, system configuration (i.e., the selected set of templates was derived using a system similar to that in use with this patient), and so on. That set of templates may then be used to diagnosis the likely cause of the fault. For instance, a signal sensed while the type corresponding type of artifact is introduced into the system may best match the template associated with fluid ingress between the lead and lead extension (versus other templates associated with other types of faults). This match may be used to diagnose a likely problem with one the connection between these two components.

Figure 7:
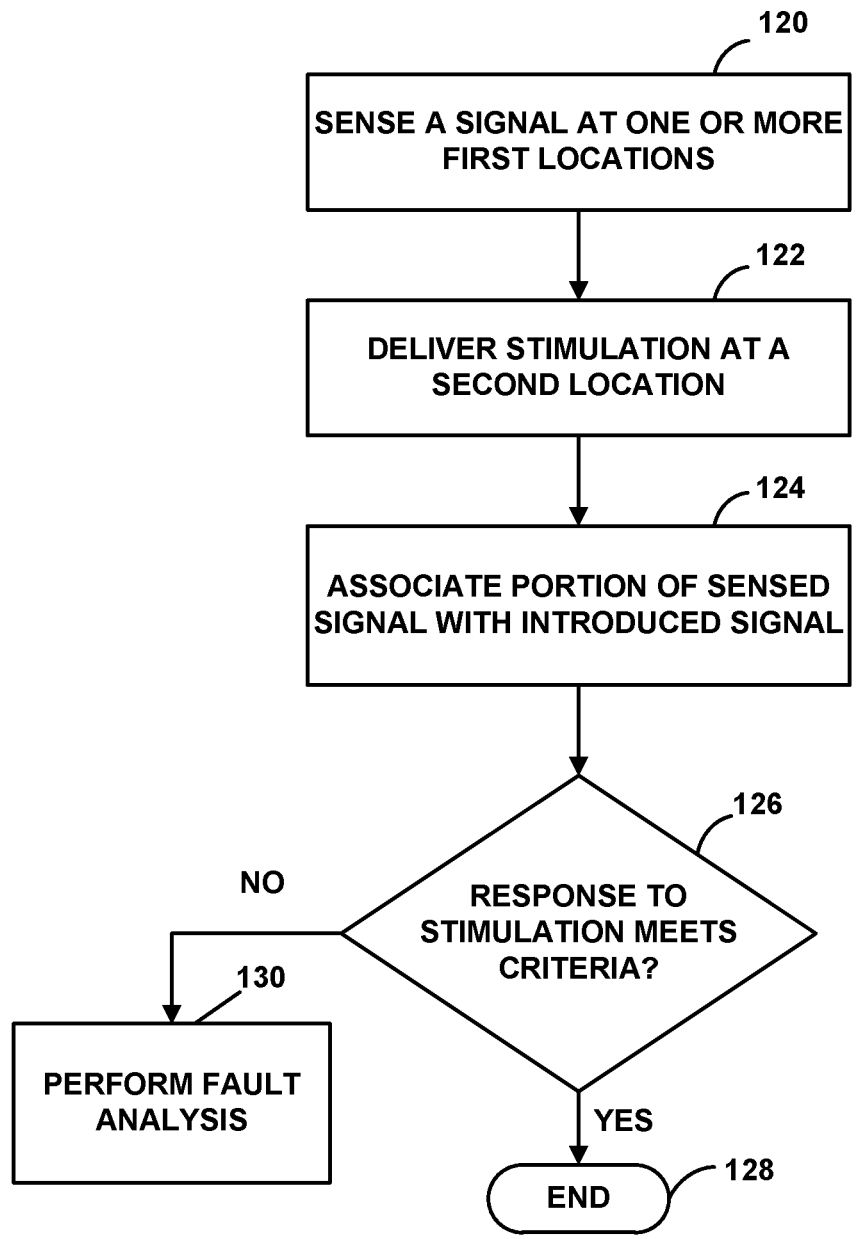
FIG. 7 is a flow diagram illustrating sensing an evoked potential at a first location when stimulation is delivered to a second location.

Analyzing the fault (110) may be performed by processor 60 of IMD 16 and/or processor 80 of programmer 14. Results of the fault analysis may be provided to the user via a display of programmer or via some other user interface mechanism. In some embodiments, this may involve displaying the sensing signal with the introduced signal for the user to analyze. The display may include time stamps to indicate when the artifact was introduced relative to the sensed signal. In some embodiments, multiple waveforms may be overlaid on one another to provide a time correlation, with a first waveform representing the sensed signal at the first location and the second waveform representing the introduction of the signal at the second location. In some cases, the fault analysis (110) may be provided automatically to a user. This outcome may be provided as a "yes/no" indication as to whether a fault likely exists within the system. Instead, the outcome could be provided quantitatively, such as using a percentage likelihood that a fault has occurred. In some cases, guidance as to the likely root cause of the fault may be provided. For instance, as discussed above, different types of faults may be associated with different templates or signatures that are stored in memory. By comparing different ones of these templates to the sensed signal and determining whether the sensed signal matches any of the templates, it may be determined whether a likely match occurs that indicates the type of fault. In some cases, such a match may be achieved by the comparison meeting some predetermined confidence level as determined by the template matching algorithm in use (e.g., there is a 90% chance that a match occurred). In this manner, the system may automatically provide guidance as to the likely cause of the fault and/or may even recommend an action to be taken to remedy the fault. Further fault analysis (110) may be performed using information obtained from various sources. For instance, as discussed above, additional information may be obtained by determine if, or what type of, an evoked response is being sensed at a first location when stimulation is introduced at a second location, as discussed in reference to FIG. 7. This type of information may be used to further isolate the source of the fault. FIG. 7 is a flow diagram illustrating sensing an evoked potential at a first location when stimulation is delivered to a second location. Specifically, a signal may be sensed at one or more first locations (120). Stimulation may be delivered at a second location (122). The second location may be location having some type of functional connectivity to the first location. This second location which has a functional connectivity to the first location may be determined using techniques discussed below.

The sensing and stimulation may occur contemporaneously with one another. For instance, sensing may occur throughout the entire period of time stimulation is delivered or may commence after a delay corresponding to the time required for the stimulation signal to travel from the first to the second location. In other cases, sensing may commence prior to stimulation, and stimulation may occur only during a portion of the time of the sensing.

In any event, a portion of the sensed signal may be associated with introduction of the signal at the second location (124). The associated portion of the sensed signal may be that portion that would be expected to be affected by the introduction of the stimulation at the second location assuming there is some type of functional connectivity that physiologically exists between the first and second locations. For instance, this may be the time segment of the sensed signal which was sensed in the HC that is expected to exhibit an evoked response because of stimulation delivered to the AN of the thalamus of the patient. This time segment of the sensed signal may be determined based on an expected delay between delivery of stimulation to the AN and detection of the evoked potential in the HC, which may be a patient-specific delay.

Next, it may be determined whether a response to stimulation as may be determined by the associated portion of the sensed signals meets predetermined criteria (126). This may be determined in any of the ways discussed herein, including comparing a time-domain or frequency-domain characteristic of the signal to a baseline signal, a template or a threshold. For instance, a baseline signal may be stored in memories 60 and/or 80 that correspond to evoked potentials that are expected to occur in systems that do not have any faults. This baseline signal may be patient-specific in that it was sensed, or otherwise derived from a sensed signal, during an evoked response at the first locations that resulted from stimulation at the second location when the system was known to be fault free.

If the response does meet expected criteria, it may be determined that a fault does not likely exist within the system (128). Otherwise, fault analysis may be performed (130) to further identify a likely cause of the fault. Further fault analysis may be performed automatically or with the help of the clinician. For instance, the associated portion of the sensed signal may be displayed on a screen of programmer 14 for viewing by a clinician who may determine a likely cause of the fault. Alternatively or additionally, the system may automatically perform further fault analysis.

In some cases, the system may compare the associated portion of the sensed signal to multiple templates, each associated with a different type of fault in a similar manner to that described in regards to FIG. 6 step 110. For instance, the associated portion of the sensed signal may be compared to different templates with the closest match indicating a type of fault. Alternatively, or additionally, the portion of the sensed signal may be compared to a baseline signal of the evoked response.

Figure 8:
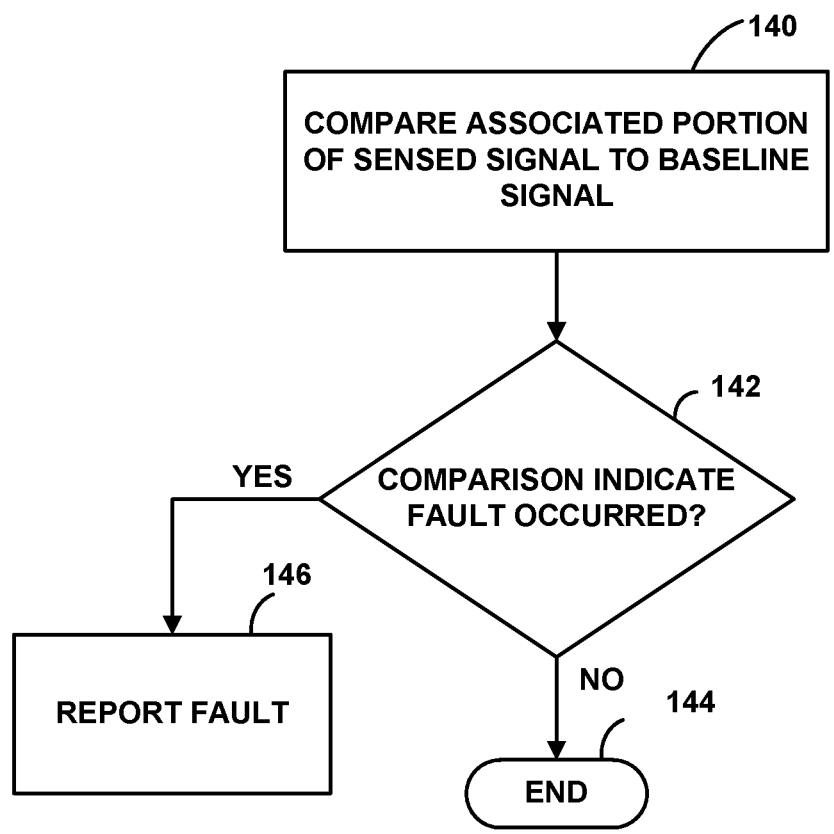
FIG. 8 is a flow diagram illustrating used of a baseline signal in analyzing whether a system fault has occurred within the system.

FIG. 8 is a flow diagram illustrating used of a baseline signal in analyzing whether a system fault has occurred within the system. The associated portion of a sensed signal may be compared to a baseline signal (140). The baseline signal may be indicative of an evoked response signals that is sensed when it was known that a fault does not exist in the system. The baseline signal may be obtained from the patient or may instead represent a signal obtained from patient population data. It may be determined whether the sensed signal indicates a fault occurred (142). For instance, if the sensed signal deviates by a certain amount, percentage, or in certain ways (e.g., does not have similar waveform shape, deflection points, or other signal characteristics) from the baseline, it may be determined that a fault has occurred in the system. In some examples, the way in which the sensed signal deviates from the baseline may be informative of the type of fault. For instance, if an evoked response appears to be present within the sensed signal but is degraded or does not have characteristics that are expected, it may be determined that some stimulation was delivered at the second location, but a fault may exist within the sensing path to compromise the signal sensed at the first location. A similar conclusion may be drawn if no evoked response is sensed at all and a comparison of the associated portion of the sensed signal to a baseline signal obtained when no stimulation is delivered at the second location results in a favorable comparison. In this case, the sensed signal is representative of what would be expected in the absence of stimulation, again leading to a conclusion that sensing is occurring fault free but some fault may be present in the stimulation pathway. On the other hand, the sensed signal may not compare favorably to either the baseline signal associated with an evoked response or the baseline signal expected when no stimulation is delivered. In this case, it may be that the sensing path contains the fault.

If the comparison (142) results in a "match" of the associated portion of the sensed signal to a baseline, as determined be known pattern matching techniques such as those discussed above, no fault is determined to occur (144) as may be reported to a user via a user interface, such as a display of programmer 14. Otherwise, if the evoked response is not detected or appears to deviate from the baseline in a manner that is indicative of a likely fault, the fault may be reported (146). In some instances, it may be possible to suggest a likely cause of the fault based on analysis such as discussed above.

In some cases, further fault analysis may be performed by repeating the method of FIG. 7 but stimulating at the first location while sensing at the second location (assuming a functional physiological relationship exists between the first and second location that allows stimulation at the first location to cause an evoked response at the second location.) For instance, if the first comparison in step 142 of FIG. 8 suggested that the fault is likely in the stimulation path, repeating the steps of FIG. 7 but stimulating at the first location while sensing at the second location may help confirm the initial fault diagnosis if the fault now appears to be in the sensing pathway, and so on.

Figure 9A:
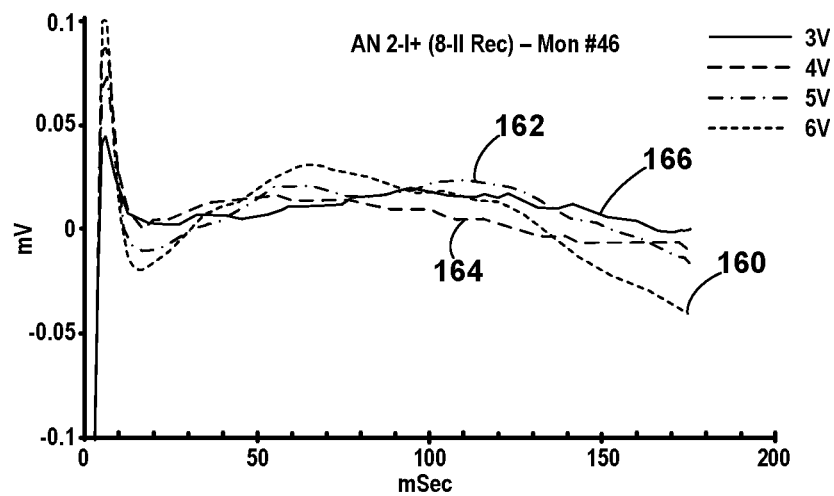
FIGS. 9A and 9B are examples of waveforms representing signals sensed in the brain of a patient during a fault condition and during a non-fault condition, respectively.
Figure 9B:
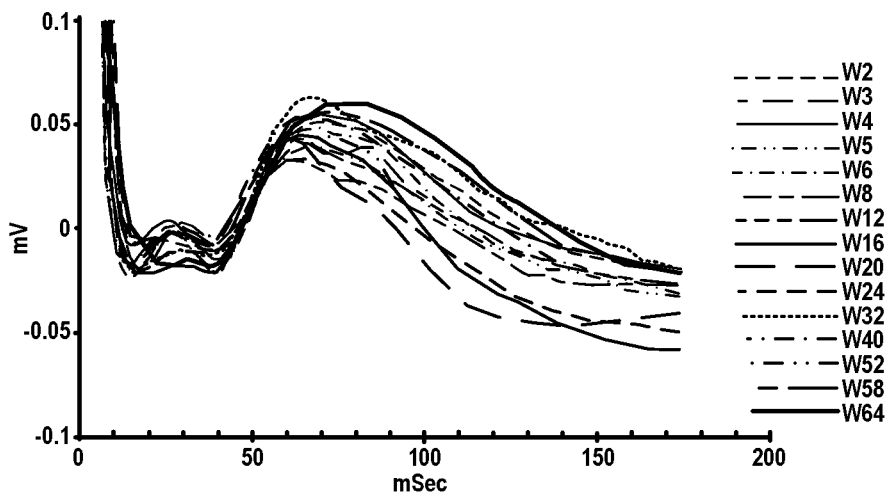

FIGS. 9A and 9B are examples of waveforms representing signals sensed in the brain of a patient during a fault condition and during a non-fault condition, respectively. In both figures, the Y axis indicates signal amplitude in millivolts, and the X axis represents time over which the signal was sensed. The location of sensing in this example is the HC.

In FIG. 9A, the four waveforms are shown, each corresponding to electrical stimulation delivered to the AN while sensing occurred in the HC. The portion of the waveform shown may be described as the associated portion of the sensed signal, since it is the portion that would correspond temporally to the delivery of the stimulation. That is, the portion may be sensed substantially simultaneously with, or in some cases after a predetermined time delay of, the delivery of the stimulation.

The four waveforms 160, 162, 164, and 166 each correspond to delivery of stimulation at the AN at a respectively different stimulation amplitude of 6V, 5V, 4V, and 3V. In all cases, waveforms 160-166 indicate that the stimulation resulted in some type of response, but the response is not as would be expected in a system free of faults. This may be appreciated by comparing waveforms 160-166 to the waveforms of FIG. 9B, which are evoked responses sensed within a system over a period of 64 weeks in a system known to be free of faults. The waveforms of FIG. 9B all commence with a rather sharp negative slope followed by a local minimum value, a local maximum value (a small "peak") that occurs between 20 and 40 milliseconds, another local minimum value, followed by a maximum peak value occurring between 60 and 90 milliseconds. These characteristics are seen to be attenuated in the four waveforms 160-164 of FIG. 9A. In fact, each of the waveforms of FIG. 9A commence with a sharp positive-going slope and a maximum peak value occurring around 10 milliseconds, followed by a local minimum value occurring around 20 milliseconds. The peak value occurring between 60 and 90 milliseconds is degraded from those appearing in the waveforms of FIG. 9B.

The signals of FIG. 9A are examples of baseline signals that may be recorded from a patient in a system known to be free of faults. The baseline signals may be recorded over a period of time as shown in FIG. 9A. The baseline signals may be averaged or processed in some other manner to derive a single baseline that may be stored for comparison to the associated portion of sensed signal. Comparison may include comparing characteristics of the baseline such as timing, amplitude, and length of inflection points, local maximum and minimum points, absolute maximum and minimum points, slopes of certain points of the waveform and so on. Faults may be detected in some cases based on an absolute amount of deviation from the baseline, a percentage deviation, the lack of expected characteristics, and so on.

In some instances, as discussed above, evoked responses may be entirely lost. This may occur when an open circuit condition occurs, such as if a conductive pathway in a lead is broken, or a contact becomes disconnected or broken. In these circumstances, the complete loss of an evoked potential may correspond to very high impedance values that can be measured between one or more pathways in the system. The high impedance values may be consistently present and measurable within the system (as when the fault is a "hard" failure that is not transient), or instead may be intermittent as when the fault is transient. Impedance values may be determined to be too high, or "out-of-range" by comparing them to baseline impedance values that are expected to occur when impedance values are in-range. Comparing measured impedance values to baseline impedance values may help confirm the presence of a fault in the system that is suspected based on the evoked response data. The impedance values may further help to pin-point which component in the system may be failing, as discussed in regards to FIGS. 10A-10D below.

Figure 10A:
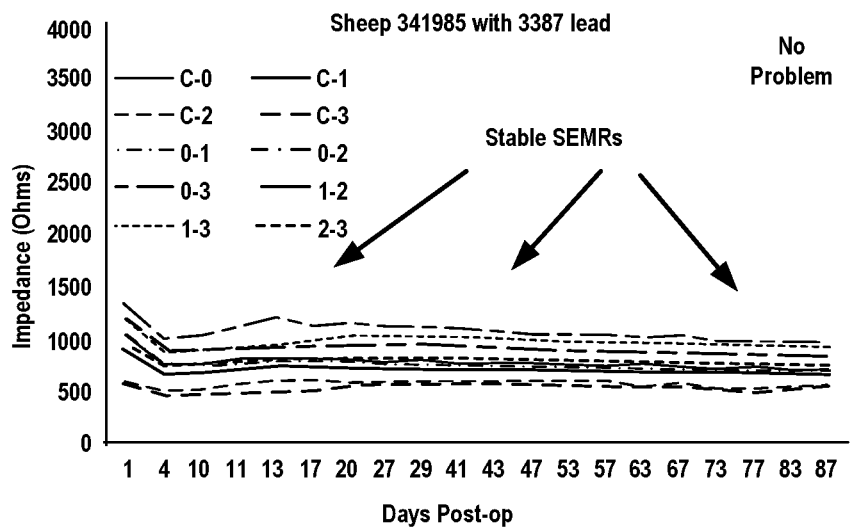
FIG. 10A illustrates multiple plots of impedance values measured between various electrode pairs of an implantable 3387 model lead, which is commercially available from Medtronic, Inc., that has been implanted in an ovine subject.

FIG. 10A illustrates multiple plots of impedance values measured between various electrode pairs of an implantable 3387 model lead, which is commercially available from Medtronic, Inc., that has been implanted in an ovine subject. This model lead includes four ring electrodes similar to what is shown as the four electrodes 24 and 26 of leads 20A and 20B, respectively, of FIG. 1. The impedance values were measured at various times following lead implantation in an ovine subject. Impedance values are plotted against the Y axis and time is represented by the X axis. As indicated by the key, four of the plots represent impedance measurements between a respective one of the four lead electrodes (designated electrodes "0" through "3") and the housing of the implantable device. These four plots are labelled, respectively, C-0 through C-3. Six additional plots represent impedance measurements between various pairs of electrodes on the lead and are labeled by the respective electrode designations. For instance, plot 0-1 represents the impedance measurement between lead electrodes 0-1.

Figure 10B:
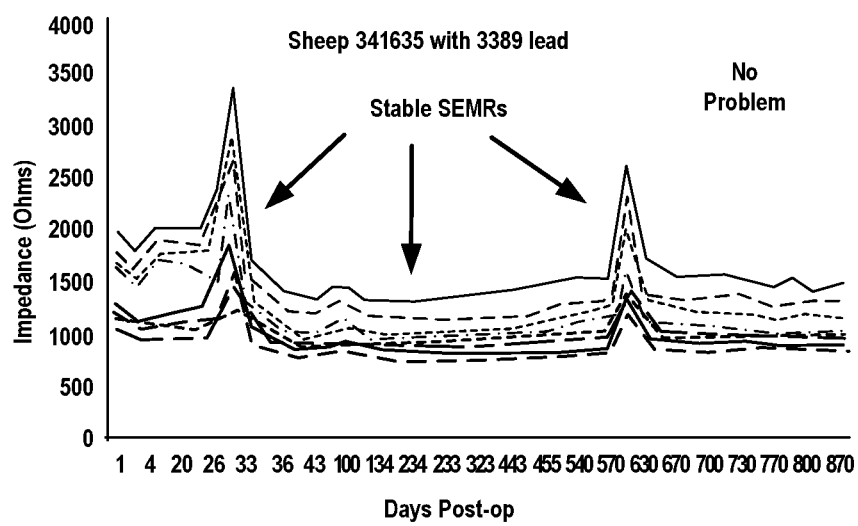
FIG. 10B is a graph of impedance values between various electrode pairs of a system comprising a 3389 model lead commercially available from Medtronic, Inc. which has been implanted in an ovine subject.

In a manner similar to FIG. 10A, FIG. 10B illustrates impedance values between various electrode pairs of a system comprising a 3389 model lead commercially available from Medtronic, Inc. which has been implanted in an ovine subject. The measurements are taken at different times following lead implantation as shown along the X axis. Impedance is plotted against the Y axis. As in FIG. 10A, four of the plots, labeled C-0 through C-3, represent impedance measurements between the four lead electrodes "0" through "3" and the housing of the implantable device. Six additional plots represent impedance measurements between various pairs of electrodes on the lead and are labeled by the respective electrode designations.

FIGS. 10A and 10B each represent impedance data obtained when the evoked responses, i.e, stimulation evoked motor responses (SEMRs), are stable. That is, the evoked responses that were sensed at the time of these impedance measurements were within a range that would be expected in a system with no faults manifesting in either the stimulation or sensing pathways that would affect the sensing or generation of the evoked response. These impedance plots may be considered to represent baseline impedance measurements that would be expected in the absence of faults affecting impedance.

The impedance data similar to that shown in FIGS. 10A and 10B may be used to confirm the possible presence of a fault as indicated by evoked responses measurements. For instance, baseline impedance data for a patient may be measured at one or more times following implant when it is known a fault does not exist within the system. The data may be stored within memories 62 and/or 82. Sometime thereafter, if sensing indicates either loss or degradation of an evoked response, impedance measurements may be taken between various electrode pairs in the system. These impedance measurements may be compared to the previously-stored baseline impedance data. This additional comparison between impedance values may be used to further confirm the presence of the fault.

Figure 10C:
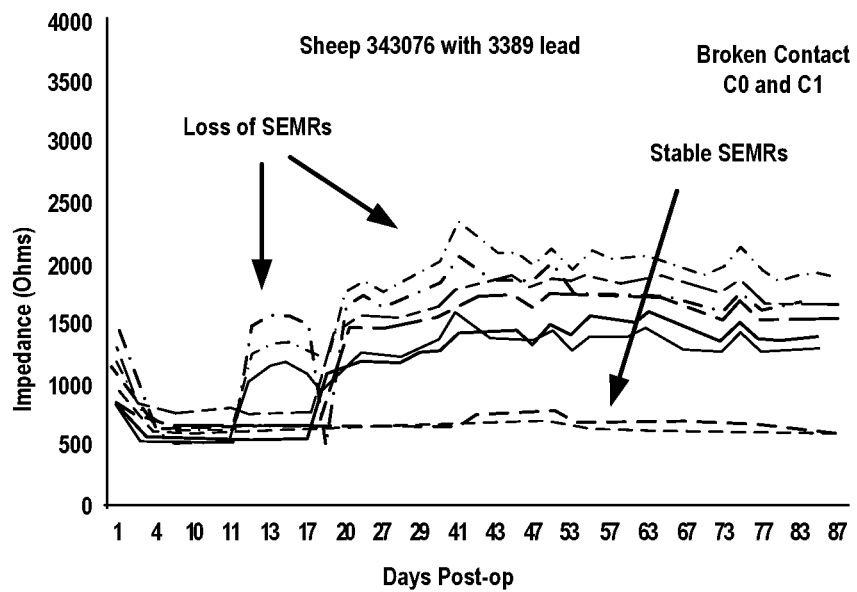
FIG. 10C is a graph of multiple plots of impedance values measured between various electrode pairs of an implantable 3389 model lead implanted in an ovine subject.

In some examples, the impedance data may help pin-point the origin of the fault. For instance, measurements between various electrode pairs can be taken and compared against corresponding baseline measurements to determine if the fault seems to be limited to just one pair of electrodes or multiple pairs. If the impedance data indicates the fault may be limited to just one pair, the evoked response data may be used to determine whether the fault may be associated with the stimulation or the sensing path, as discussed above. On the other hand, if the impedance data indicates multiple impedance values are out-of-range, an evaluation may be performed to determine what logic is in common between the pathways represented by these measurements. This common logic may be identified as the potential source of the fault. FIG. 10C illustrates multiple plots of impedance values measured between various electrode pairs of an implantable 3389 model lead implanted in an ovine subject. As in FIGS. 10A and 10B, impedance is plotted against the Y axis and time is represented by the X axis. The various plots correspond to the various electrode combinations discussed above for FIGS. 10A and 10B, including plots for C-0 through C-3 between electrodes 0-3 and the housing, respectively, and additional plots 0-1, 0-2, 0-3, 1-2, 1-3, and 2-3 for each of the six possible pairs of the electrodes on the four-electrode lead. The impedance values were measured at various times following lead implantation in an ovine subject.

Sometime between day 29 and 35, evoked response measurements indicated that the evoked responses were lost (i.e., were not sensed at all, or substantially degraded) for those measurements involving electrodes "0" and "1". The impedance data also shows that all of the impedance plots involving these electrodes, including C-0, C-1, 0-1, 0-2, 0-3, 1-2, and 1-3 indicate out-of-range impedance values. Only the impedance plots for C-2, C-3 and 2-3 illustrate in-range impedance values such as those that correspond to what is shown in the baseline data for the 3389 model lead in FIG. 10B. Evoked response waveforms sensed for electrodes "2" and "3" confirm that these evoked responses remain stable, confirming that there are likely no faults in the pathways associated with these two electrodes. In this manner, the impedance data confirms the possible fault that was already indicated by the evoked response data for the "0" and "1" electrodes, and also helps confirm that there are likely no faults associated with electrodes "2" and "3".

The set of impedance plots depicted by FIG. 10C, which were obtained in a system known to have broken contacts for electrodes "0" and "1" may, in some cases, be stored as templates. These templates may be compared against out-of-range impedance values to help pin-point the source of a fault. For instance, if a set of out-of-range impedance plots substantially matches a stored set such as shown in FIG. 10C, it may be determined that contacts "0" and "1" are broken. Any number of sets of templates corresponding to known system faults may be stored in this manner for use in further analyzing the source of a system fault.

Figure 10D:
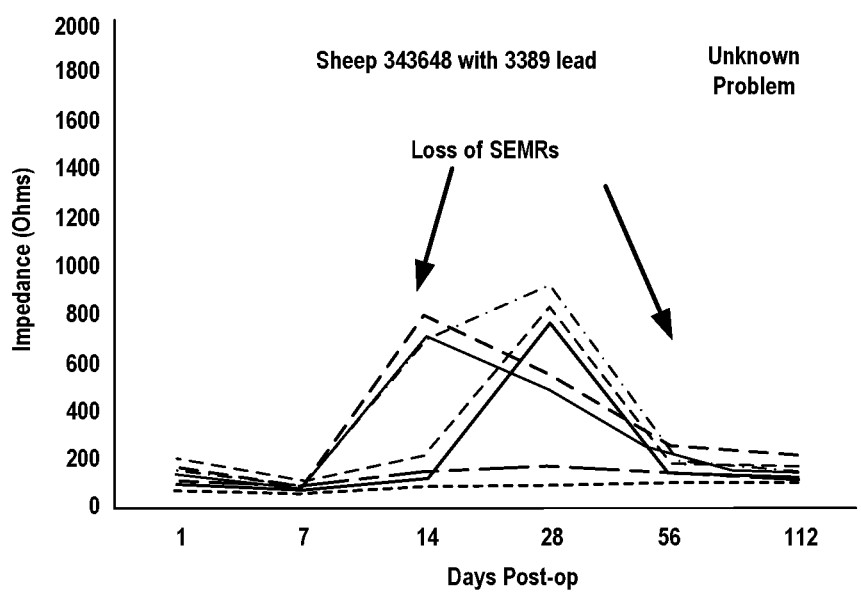
FIG. 10D is another graph of plots of impedance values measured between various electrode pairs of an implantable 3389 model lead implanted in an ovine subject.

FIG. 10D illustrates another set of impedance value plots measured between various electrode pairs of an implantable 3389 model lead implanted in an ovine subject. The same set of electrode pairs are represented by the various plots as those shown in FIGS. 10A-10C, and as in FIGS. 10A and 10C, the Y axis indicating impedance values and the X axis representing time.

The data shown in FIG. 10D is associated with an unknown problem. What is important to note is the correspondence between out-of-range impedance values and the loss of evoked potential. For instance, around day 6, impedance values for many of the electrode pairs begin to climb. At day 14 and after day 28, the evoked response signal is lost or substantially degraded for a subset of those electrode combinations demonstrating out-of-range impedance values. While impedance values for the various combinations of electrodes that are associated with out-of-range impedance begin to drop between days 14 and 28, the values never-the-less remain out-of-range as indicated by a comparison between the data of FIGS. 10B and 10D. The loss of the evoked response signal after day 28 for some of the electrode combinations confirms the possibility of the fault. Thus, by using both evoked response data and the impedance data, the possibility of a failure can be further confirmed and, in some cases, more accurately pin-pointed.

In some cases, out-of-range impedance values may be consistently sensed within the system, indicating the fault is manifesting itself most, or all, of the time within the system. In other cases, the out-of-range impedance values may be obtained only intermittently. This may be the case, for instance, if a lead or lead extension has a fracture that results in an open circuit upon patient motion. For instance, a lead extension that may be tunneled under the skin of the patient's neck, running from the proximal end of the lead located on the patient's head to an implantable device implanted in the patient's torso. A fracture in the lead extension may only present a high-impedance pathway when the patient turns his or her head, causing the fracture to separate.

An intermittent fault of the type resulting in out-of-range impedance measurements may be diagnosed by obtaining impedance measurements substantially real-time. A succession or sequence of impedance values may be obtained over time as, for instance, the patient is undergoing motion. The impedance measurements may be time-correlated with the patient's motion so that opens and shorts occurring as the patient moves will be reflected in the time-sequence of measurements obtained for a particular circuit pathway (e.g., the pathway including multiple electrodes and the conductors coupled to these electrodes.)

As a particular example of the foregoing, a user such as a clinician or patient may provide input such as by interacting with a user interface 86 of a programmer 14 (FIG. 4) or some other external device and/or by tapping on the IMD 34 in a way that may be detected by an on-board accelerometer. Such user input may be provided at a time that corresponds with, or is time-correlated to, the turning of a patient's head or some other movement. Such input may cause a timestamp or some other marker to be stored in memory to indicate time(s) of patient motion. This timestamp or marker data may be introduced into a stream of impedance values by a system clock (e.g., a clock of IMD 34 and/or a clock of programmer 14) or otherwise stored with the data in memory 62. In this way, it may be possible to determine which portion of a sensed signal corresponds to a time at which the motion is occurring.

A sequence of impedance values that includes marker or timestamp information indicating which values correspond with motion may be stored in memory 62 of IMD 34, stored within memory 82 of programmer 14, stored in some other external device (e.g., a clinician workstation a cell phone or PDA, or some other device), and/or uploaded to "the cloud" for storage on a central database. This data may further be used to generate information that may be presented to a clinician. For instance, a display on a screen of programmer 14 may be used to illustrate in a graphical or other format the variation in impedance over time. This graphical or other display could be annotated to indicate the times at which patient movement occurred (e.g., the times of head movement) so that the clinician can determine whether a likely short or open is occurring intermittently with some type of movement.

A display of the type discussed above may also be correlated (e.g., on a common time axis) with a graphical representation of the patient's movement (e.g., a representation of a head performing rotational movements at the same frequency as was performed by the patient) along with a rolling window displaying the stream of impedance data so that a clinician can determine a likely rotational position of a patient's head at the time of an intermittent short of open, and thereby aid in the diagnosis of the system fault.

In a manner similar to the foregoing, other signals may reflect the presence of patient motion. For instance, LFPs, ECoGs, EEGs or some other physiological sensed signals may be acquired at a time of patient motion. In a manner similar to that discussed above in regards to impedance signals, timestamps or other markers may be stored along with a portion of the physiological sensed signal that corresponds temporarily with the motion. These portions of the signals that were sensed during, or substantially during, the occurrence of the patient motion can then be analyzed to determine whether a motion artifact is evident in the signal. Motion artifacts may be manifested as short, high-amplitude, spikes that are non-physiological in nature. Such signals may be characterized as non-physiological because of their consistent non-physiological frequency (e.g., corresponding to frequency of patient motion rather than any frequency naturally occurring within the physiological signal). This may allow the user to more readily determine the likelihood of a fault, and may provide further confirmation of a motion-induced open or short in the system. For instance, a motion artifact may not be evident in an LFP signal sensed within a system that does not have a fault. Conversely, if a system does have a fracture or other intermittent failure, an intermittent leakage path may result that affects noise and/or stimulation rejection, interfering with the sensed signal. This is as shown in FIGS. 11A and 11B.

Figure 11A:
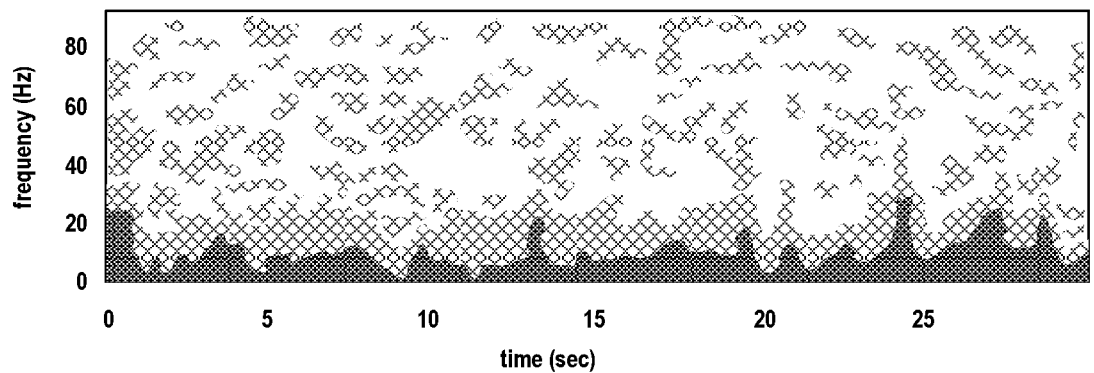
FIG. 11A is a conceptual diagram illustrating the frequency content of an LFP signal over time in a system free of a fault.

FIG. 11A is a conceptual diagram illustrating the frequency content of an LFP signal over time in a system free of a fault. The signal of this example is sensed in the STN of a patient.

The frequency content of the signal is indicated along the Y axis and time is depicted on the X axis. The diagram of FIG. 11A represents a scenario with no system fault and no motion present. The LFP is as would be expected for the patient, and may be considered a baseline LFP signal for a lead implanted in the STN.

Figure 11B:
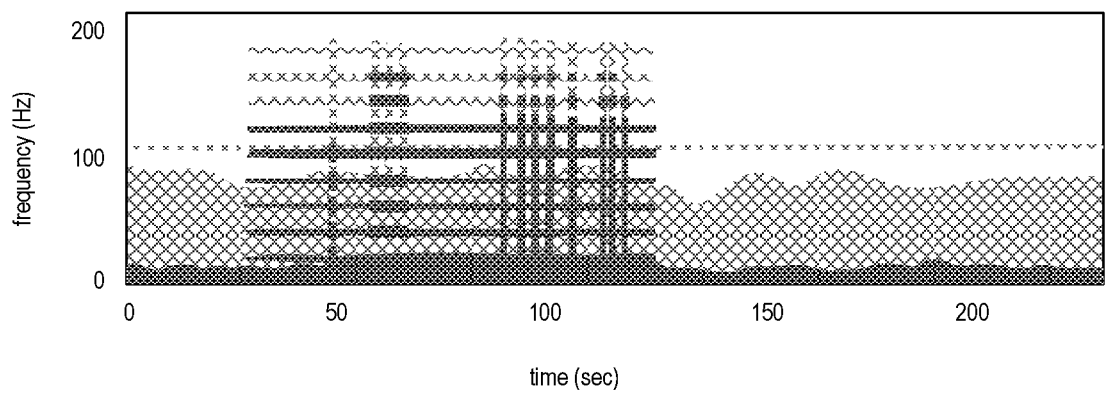
FIG. 11B is a conceptual illustrating the frequency content of an LFP signal over time in a system that includes an intermittent fault in the lead sensing an LFP signal in the STN.

FIG. 11B is a conceptual diagram similar to FIG. 11A illustrating the frequency content of an LFP signal over time in a system that includes an intermittent fault in the lead sensing an LFP signal in the STN. During a portion of the time represented by FIG. 11B, the patient, which is an ovine subject, is moving its head. This causes a break that impacts rejection of the stimulation signal which is being delivered to the patient at the same time as the signal is being sensed. As a result of the compromised stimulation signal rejection during the period of motion (e.g., extending between about 30 and 130 seconds), the sensed LFP signal contains content in frequencies that are harmonics and sub-harmonics of the delivered stimulation. This is shown in FIG. 11B as signal content at about 20 Hz, 40 Hz, 60 Hz, 80 Hz, 100 Hz, and so on, in regular increments.

In the example of FIG. 11B, the artifact introduced into the signal is a stimulation artifact resulting from degraded stimulation rejection. The motion of the patient resulted in the manifestation of the fault, which caused a leakage path resulting in this stimulation degradation. In other cases, the motion itself may cause a motion artifact. This may be apparent as frequency content in the sensed signal that corresponds to the frequency of the patient motion. For instance, the patient may be directed to turn his or head at a frequency of about once every second. This may cause extraneous frequency content of about 1 Hz to appear in the signal.

Regardless of the artifact source, the presence of this artifact in the sensed signal may be used to detect the intermittent failure. This type of signal analysis may uncover a potential fault even in scenarios wherein impedance measurements of the type discussed herein appear normal. For instance, if fracture is small enough, impedance measurements in the affected pathway may not be out-of-range but LFP or other physiological signals sensed with the pathway may still manifest the type of extraneous content depicted in FIG. 11B, thus leading to early diagnosis of the fault.

Figure 12:
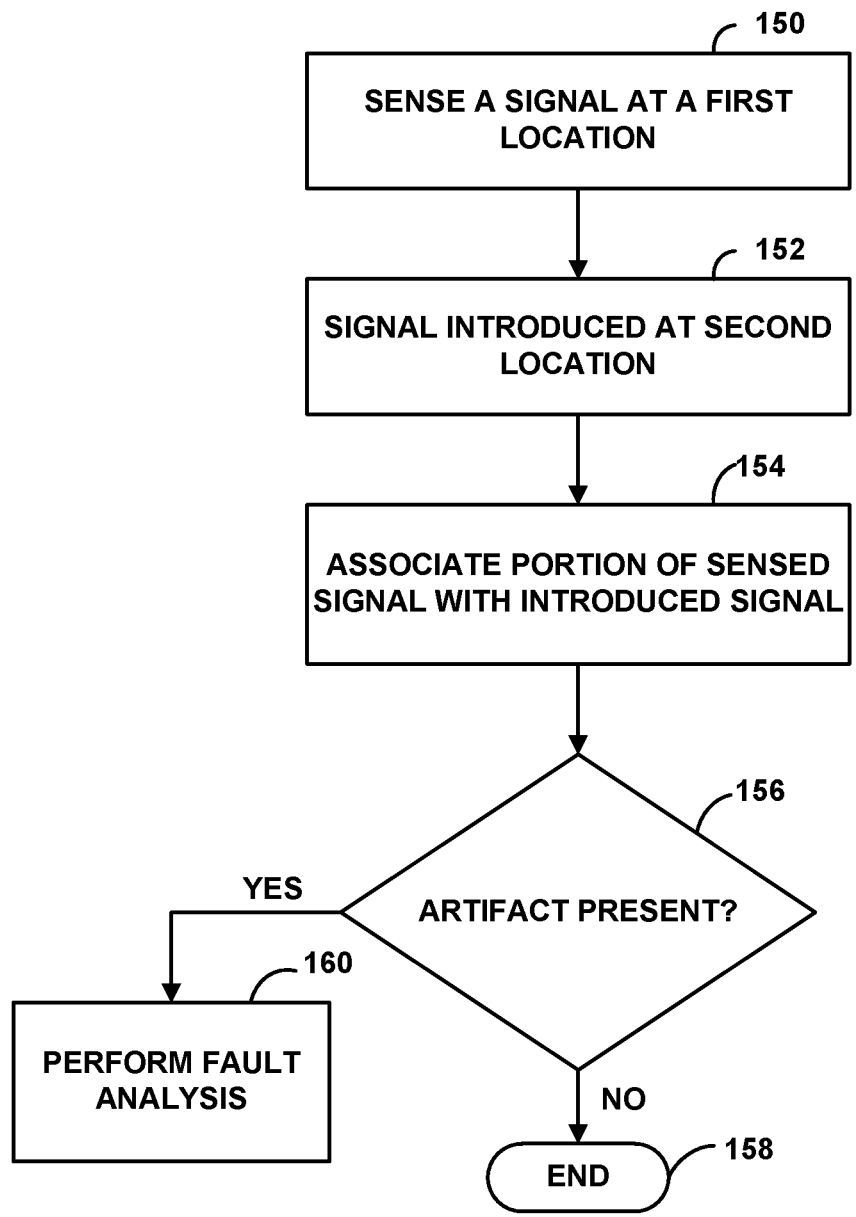
FIG. 12 is a flow diagram illustrating a method of diagnosing a fault by detecting an artifact in the signal.

FIG. 12 is a flow diagram illustrating a method of diagnosing a fault by detecting an artifact in the signal. A signal may be sensed at a first location (150). For instance, the first location may be within a brain of a patient, such as an STN or any other location. A signal may be introduced at a second location that may be different from the first location (152). This signal may comprise stimulation introduced at a second location within the STN or may be delivered to an entirely different structure of the patient's brain. The second location may, or may not, be functionally connected to, or associated with, the first location. In other cases, the introduced signal may be a motion artifact caused by the patient turning his or her head. In yet another example, an artifact may correspond to the beating of a patient's heart or tapping on the housing of a medical device at a predetermined frequency.

A portion of the sensed signal may be associated with the introduced signal (154). For instance, a timestamp or other marker may be stored, or otherwise associated, with the portion of the sensed signal that was sensed while the signal was introduced at the second location. If the signal was introduced at the second location for the entire time the signal was sensed at the first location, the entirety of the sensed signal may be associated with the introduced signal.

It may be determined whether an artifact is present in this associated portion of the sensed signal (156). If not (158), the sensed signal may not indicate the presence of the fault. If an artifact is present, however, fault analysis may be performed (160). This may involve collecting and analyzing other data such as evoked response(s) and impedance measurement according to techniques described herein. It may further involve obtaining patient feedback, such as whether they are experiencing loss of therapy at one or more times (e.g., during periods of patient motion) and so on. As discussed above, in some cases LFP, ECoG, EEG, or other physiological signals may be sensed in real-time or substantially in real-time. Such data may be time-stamped or otherwise tagged to indicate which signal samples correspond to patient motion. An example of such data is shown in FIG. 13.

Figure 13:
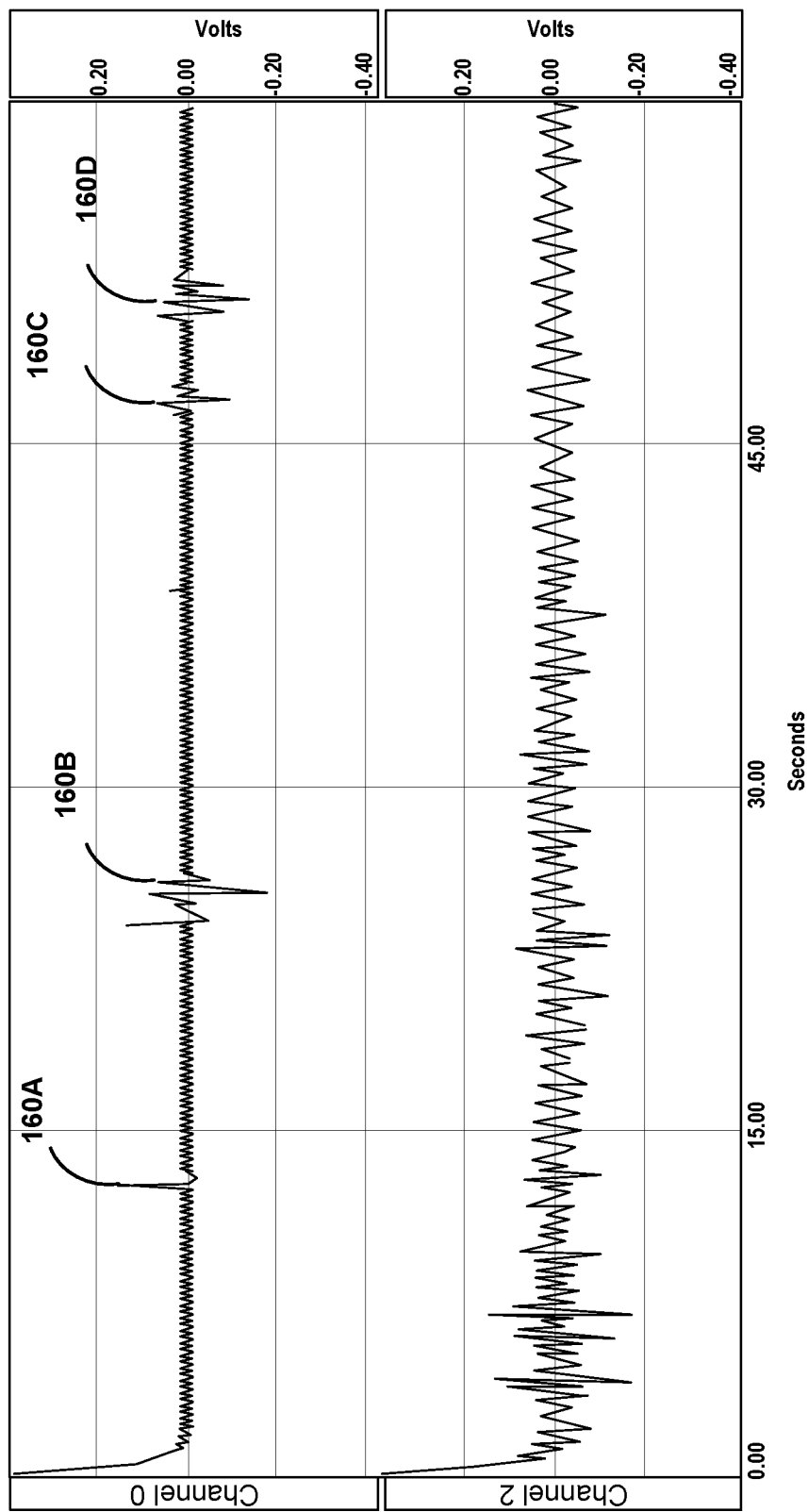
FIG. 13 is a signal diagram of two LFP recordings obtained from the AN and HC of an ovine subject as may be used to determine whether a fault exists within the system.

FIG. 13 is a signal diagram of two LFP recordings obtained from the AN and HC of an ovine subject. The signal amplitude (in volts) is plotted along the Y axis while the X axis represents time (in seconds). The top waveform is that obtained from the AN and reflects the movement artifact occurring when the patient intermittently moved its head, as is represented by one or more signal "spikes" 160A-160D in this signal. The bottom waveform was obtained from the HC of the subject and does not include the signal spikes.

In some examples, the type of LFP recordings shown in FIG. 13 may be obtained by collecting the signal data in real-time or substantially in real-time and storing this data to memories 62 and/or 82 using data streaming, for instance. In some cases, this data may include one or more time-stamps or markers. For instance, a user may be allowed to provide input via a user interface of programmer 14 indicating when the patient moves. This input may result in markers or time-stamps being stored with the data to indicate which data sample(s) correspond with, (or were collected at substantially the same time as), the movement. Alternatively, the movement indication provided by a user may be associated with a time indication and may be stored separately and later used by the system to annotate the data. As still another example, a movement indication may be provided automatically by an accelerometer, gyroscope, or other movement sensor worn by the patient.

In examples, a display may be provided to a user via user interface 86 of programmer 14 or some other user interface that of the LFP data. An LFP waveform may include markers indicating time of motion. Alternatively, a separate waveform illustrating time of motion may be displayed with, or may overlay, the LFP waveform in a time-correlated manner that allows a user to readily determine which portion of the LFP signal corresponds with the motion. In this manner, the user may determine if the motion is causing a motion artifacts, as may be the case if an intermittent fault has occurred in the system. Such faults may not even be apparent from impedance measurements. Therefore, the motion data may help with the early detection of such things as hairline fractures in conductors of a lead or lead extension, a fluid leakage pathway resulting from incomplete sealing or an insulation breach, or some other fault that would otherwise be impossible or difficult to detect with just impedance measurements.

While FIG. 13 illustrates an LFP signal that contains motion artifacts resulting from the turning of a head, other types of motion might cause these artifacts, such as the swinging or other movement of arms and/or hands, twisting of a torso, movement in leads and/or feet, bending at the waist, or the movement (beating) of the patient's heart. As discussed above, the times and/or frequency of this movement data may be stored in memory and used to annotate the sensed LFP data or otherwise used to indicate to the user which portions of the sensed data corresponds with the movement. In some cases, the frequency of the movement (e.g., frequency of the beating heart) will be enough to determine whether the LFP signal is being affected by that movement, since the frequency of the signal artifacts will correspond substantially to that of the movement.

The above example illustrates an artifact in a signal obtained from an electrode in the AN of the patient's brain. Signals obtained from other locations in the patient's brain, such as the STN, may likewise contain similar motion artifacts. Moreover, which the signals of FIG. 13 are LFP signals, other physiological signals may contain motion artifacts and may be used in a similar manner to determine faults. For instance, EEG, ECoG, and other physiological signals may be used in a similar manner.

As described herein, using some type of introduced signal, such as a motion artifact, a cardiac waveform artifact, or stimulation that can be sensed at a remote location may be used in any combination to help detect a fault in a medical device system. This information may help detect a fault even before impedance measurement may indicate that a fault has occurred and may be particularly useful in detecting intermittent faults. Impedance measurements may be used to further confirm a fault exists. In particular, impedance measurements obtained in real-time during patient motion may help detect intermittent faults that are only apparent during such motion.

Another way to uncover a potential fault is determine whether the efficacy of a particular parameter set used to deliver therapy has changed. For instance, if a fault is occurring that is resulting in an increase of impedance of a lead or lead extension in a system that used voltage-controlled stimulation, the therapy received by the patient at a particular stimulation amplitude may no longer be efficacious. To receive the same level of therapy as was previously experienced prior to the fault may require an increase in the stimulation amplitude. This can be determined by periodically performing therapy titration and obtaining patient feedback, as described in reference to FIG. 14.

Figure 14:
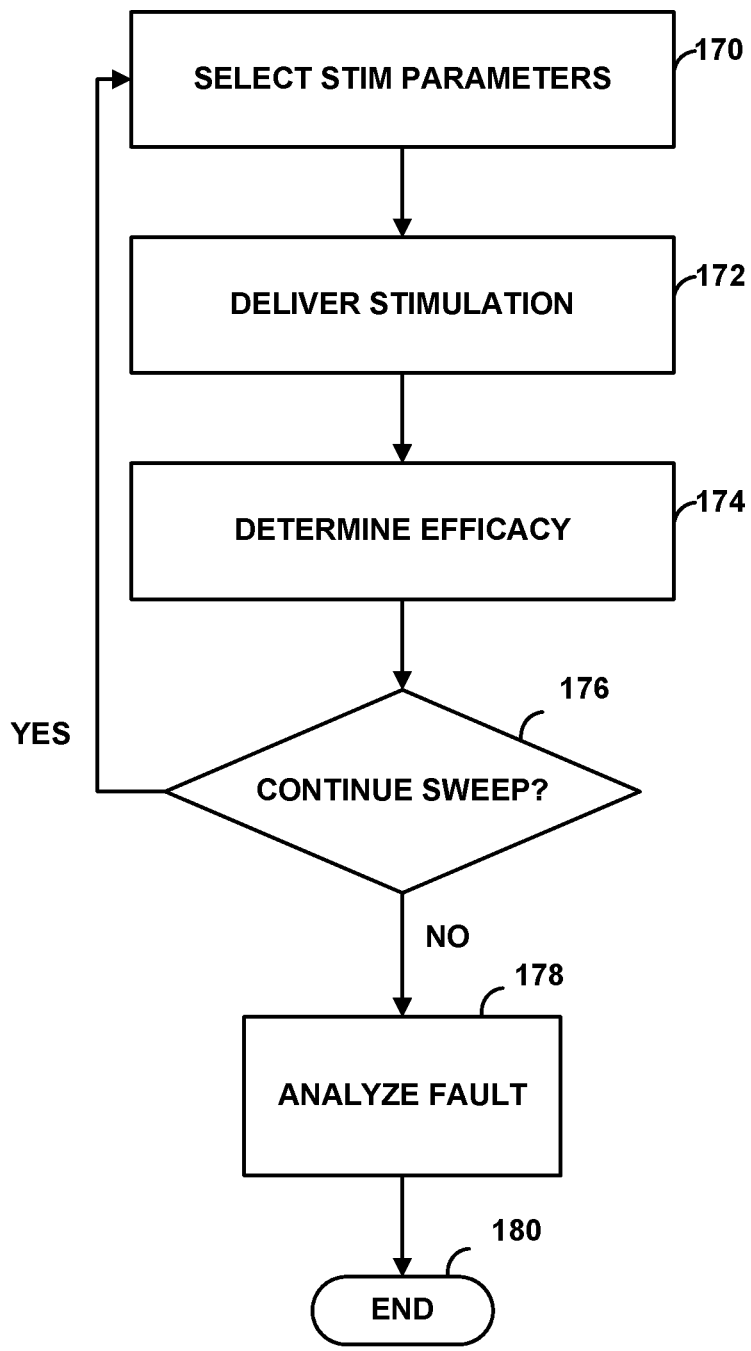
FIG. 14 is a flow diagram illustrating therapy titration performed to determine whether a change in therapy efficacy may have occurred.

FIG. 14 is a flow diagram illustrating therapy titration performed to determine whether a change in therapy efficacy may have occurred. A set of stimulation parameters may be selected for delivering therapy to the patient (170). Therapy may be delivered using these stimulation parameters (172). An efficacy of the stimulation may be determined (174). That efficacy may be determined using clinician observations, such as a clinician assigning a score that indicates how well the patient is responding to therapy. An example of such a score is the Unified Parkinson's Disease Rating Scale (UPDRS) used to rate symptoms of Parkinson's disease. In some cases, automated feedback may be provided as a user performs a task. For instance, accelerometers and/or other motion/activity sensors may be used to access tremor, determine smoothness and/or speed of gait, the quickness of a finger tap exercise, and so on. In some case, a patient may interface with a user interface 85 of a patient programmer 14 of some other user interface to obtain a rating of efficacy that is partially or entirely assigned in an automated manner. In some cases, the patient may provide feedback, as by entering information into an electronic diary.

Next, it may be determined if the parameter sweep is to continue (176). If so, one or more of the stimulation parameters may be altered and steps 172 and 174 repeated to determine if the alternative parameter set increased or decreases efficacy. In some cases, one parameter, such as stimulation amplitude, may be swept from a high to low value or vice versa to find a value that optimally treats patient symptoms. Power consideration may be taken into account when determining whether the parameter value is optimal. For instance, an amplitude that is high enough to get good patient responses, but not so high as to increase energy usage beyond a predetermined rate, may be selected as an optimal amount.

In the foregoing manner, any number of stimulation parameters may be swept, such as stimulation amplitude (voltage or current), pulse width, pulse rate, and burst rate (if non-regular stimulation patterns are being used. A "sweep" may further involve delivering a sequence of stimulation parameters or non-pulsed waveforms to determine which of the sequence and/or waveform is most efficacious. A "sweep" may also involve delivering stimulation using a sequence of different electrode combinations, including bi-polar, unipolar, or multi-polar configurations. The foregoing activity may, in some cases, be performed when a fault is known to be absent in the system. In this case, the parameters that are ultimately selected as the most efficacious provide a baseline set of parameters that may be stored within memory 62 and/or memory 82. These parameters may be used to deliver therapy to a patient for a selected period of time after the titration is performed. In some a case, after the initial sweep is considered complete (176), any fault analysis that is performed (178) will not indicate the presence of a fault.

Periodically, the method of FIG. 14 may be repeated. If a marked change in the parameters that are determined to be most efficacious occurs in steps 170-176, further fault analysis may be performed in step 178 using any of the aforementioned approaches. For instance, if amplitude needed to deliver efficacious therapy to the patient increases above some threshold amount or threshold percentage, it may be determined whether an open or high-impedance condition is developing or has occurred (e.g., due to a fraction in a lead or lead extension) in the stimulation pathway. For instance, impedance measurements may be taken to further confirm whether such a condition is occurring. Additionally, or alternative, this may trigger other tests, such as the system automatically or with the help of a user instructing the patient to perform some motion task while measurements are being taken to determine whether motion artifacts are now present within the sensed signal. In some cases, measurements may be taken to determine whether cardiac artifacts are now being manifested within the signal. In some cases, stimulation may be delivered at a second location while sensing occurs at a first location to determine whether the sensed signal has changed from the baseline signal obtained during a time when no fault was present in the system. In examples, the stimulation may then be delivered at the first location while sensing is performed at a second location to further pinpoint the location of any fault. In this manner, various types of trouble-shooting may occur in an automated or semi-automated manner. Furthermore, testing involving use of sensed signals and artifacts may uncover faults that could not be determined using impedance measurements or efficacy changes alone.

Figure 15:
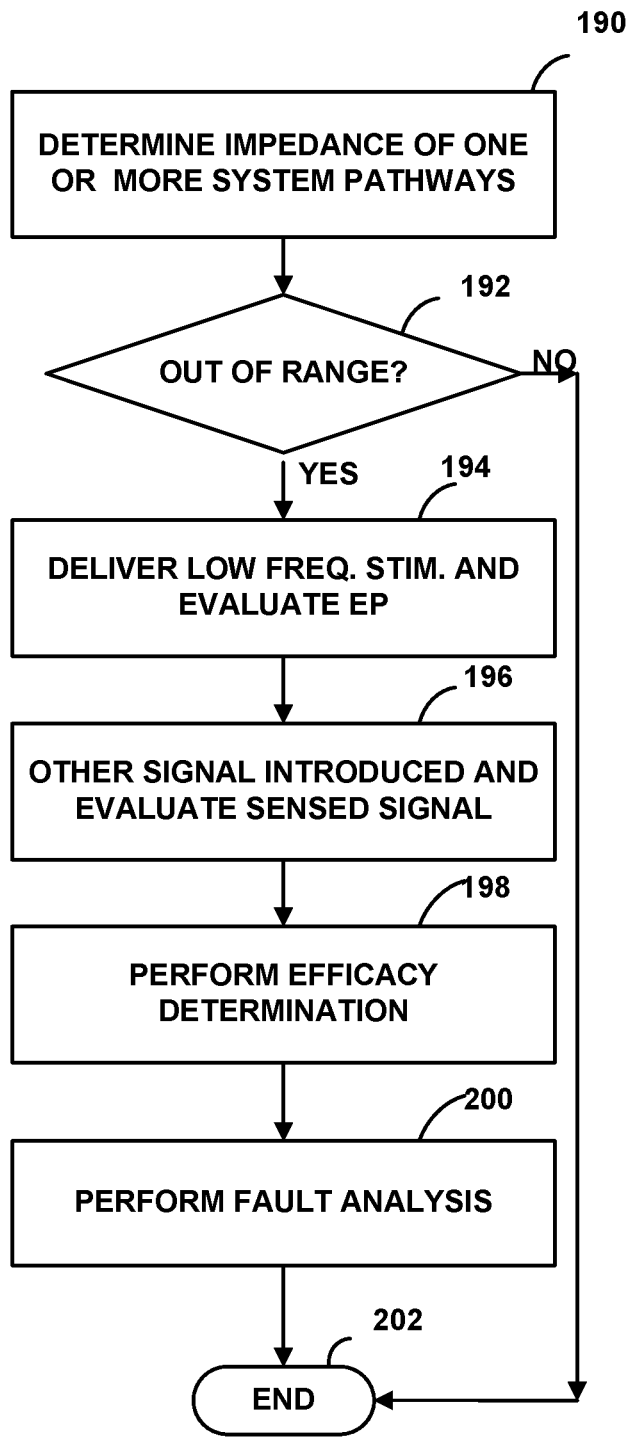
FIG. 15 is a flow diagram illustrating an example method according to the current disclosure.

FIG. 15 is a flow diagram illustrating an example method according to the current disclosure that uses various measurements within the system to diagnose a system fault. It may be determined whether an impedance measurement in one or more system pathways is out of range (190). In some example, further analysis is performed only if the impedance is out of range (192) as shown in FIG. 15. In other examples, even if impedance is out of range, analysis may continue. This alternative approach may be desirable to detect faults that are not necessarily detectible solely by impedance measurements.

If further analysis is desired, low frequency stimulation may be delivered (e.g., at a second stimulation site) and evoked potential signals may be detected (e.g., at a first stimulation site) as shown at step 194. Other signals by further be introduced (e.g., at a second site) and sensing may be conducted (e.g., at a first site), as shown at step 196. Such signals may be, for instance, motion signals introduced by a patient performing a specific motion or task such as turning his or her head. The introduced signals may be the beating of the patient's heart. Other signals introduced into the patient's body may be used in addition to or instead of the aforementioned signals, such as tapping on the "can" of the implantable device. Additional analysis may include per-forming a parameter sweep to determine whether the efficacy of therapy is changing over time, as may help determine whether a low or high impedance pathway is developing in the system (198). Any one or more of the measurements and/or sensed signals may be used to perform fault analysis.

Figure 16:
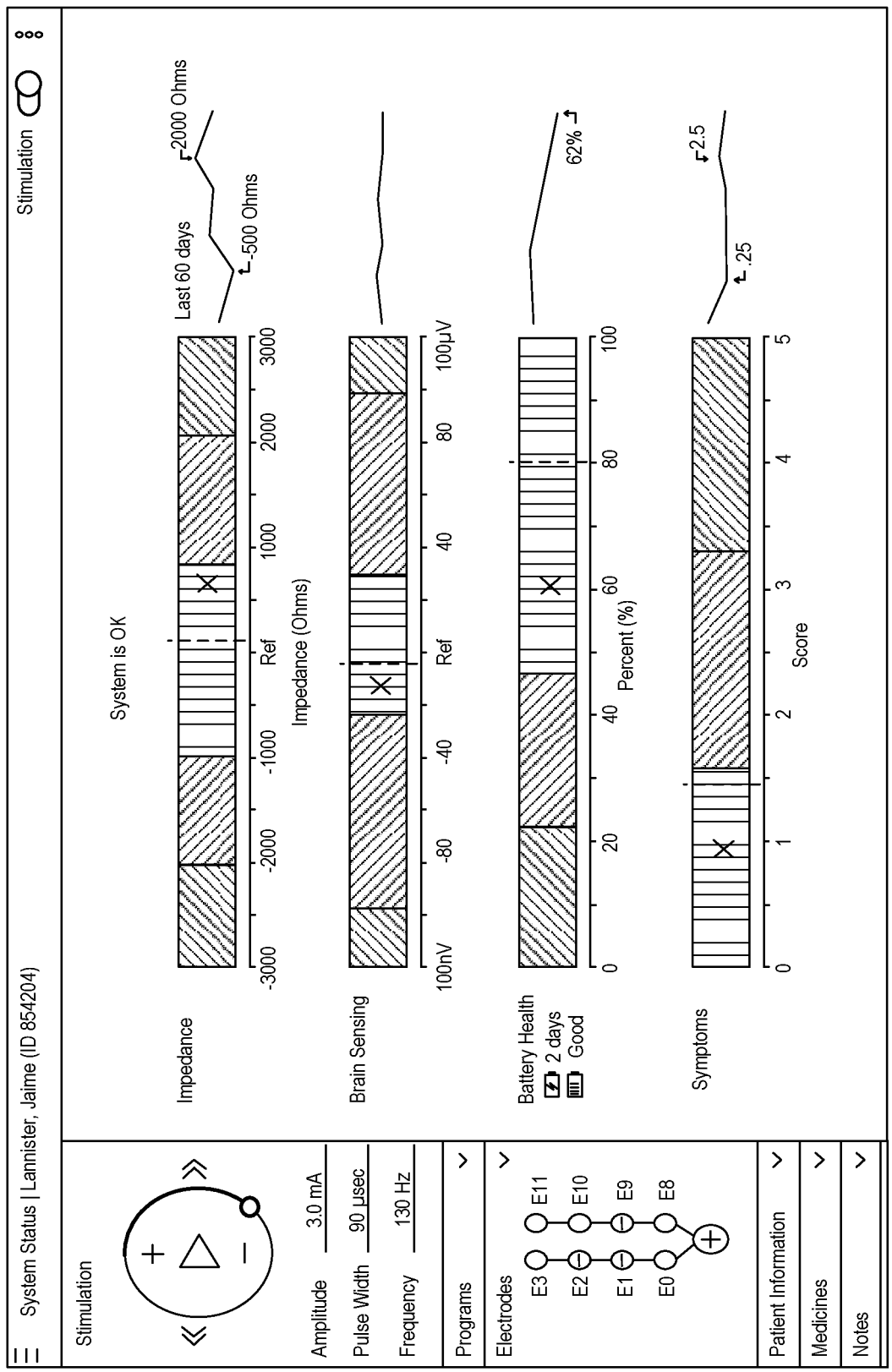
FIG. 16 is an example of a dashboard screen that may be provided to report information used to diagnose potential faults as described herein.

FIG. 16 is an example dashboard screen that may be presented to a user to indicate the result of the type of testing discussed herein. Stimulation parameters are shown along the upper left column along with the electrode configuration in use at the time. An impedance measurement provided in the center top pattern shows impedance (in ohms) as measured in the stimulation pathway, including a trend diagram illustrating any impedance changes over the last sixty days.

Below the impedance measurement data is shown a sensed brain signal (in microvolts) that is obtained at a first site when stimulation is delivered to a second site, as well as trend information shown over the past sixty days. Under this information is provided data showing battery health as a percentage of full capacity, and further indicates the remaining time until next recharge is required, which in this case is 2 days. Trend information is shown for the battery.

At the bottom of the central panel, symptom information is depicted using a rating scale from "1" to "5", with a rating of "5" indicating symptoms that are most severe. A UPDRS is an example of such a score. A trend diagram illustrates how the score has changed over the past sixty days. This score may be provided when the patient is receiving therapy using one or more baseline therapy sets, as discussed above. The information shown in FIG. 16 indicates the system is "OK" and likely fault-free.

Figure 17:
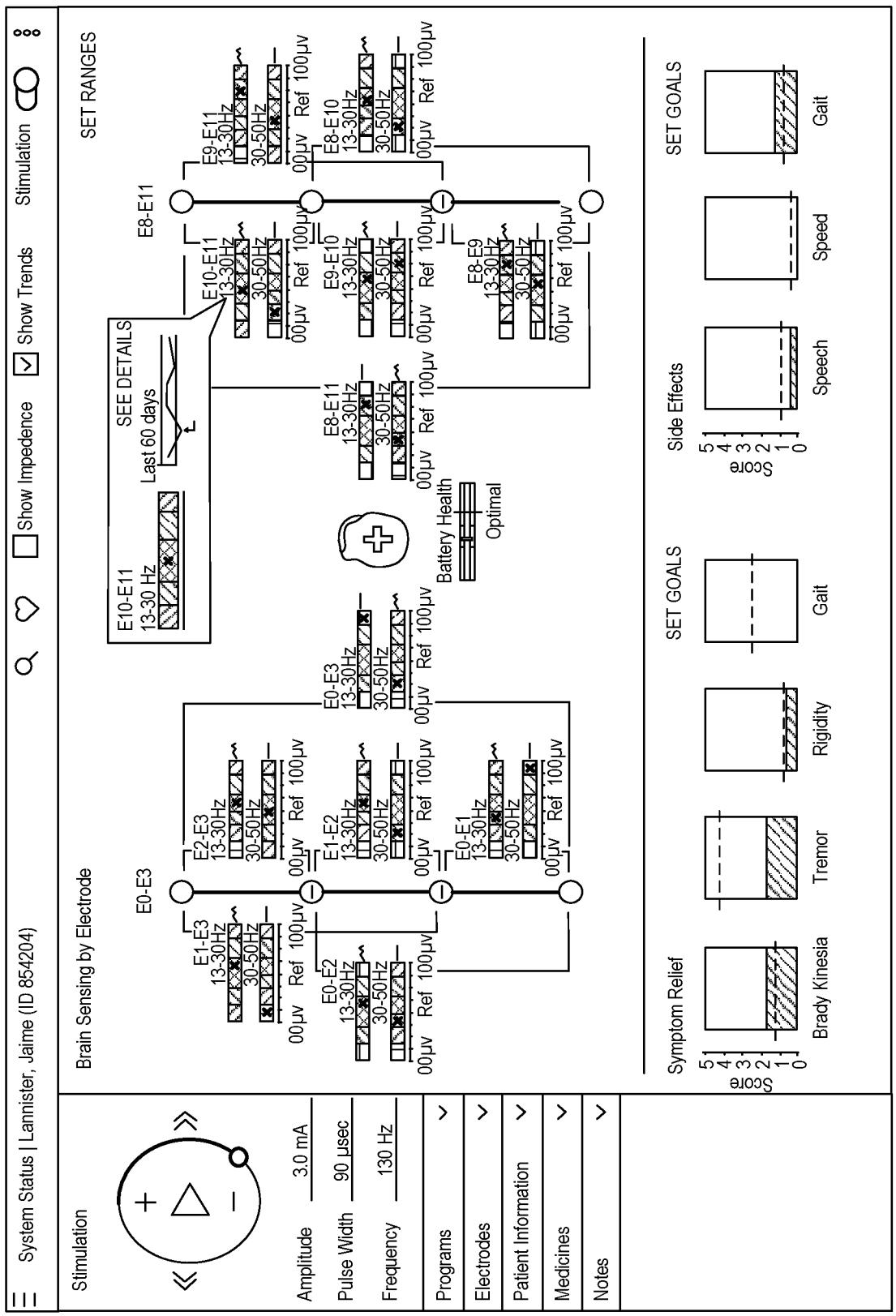
FIG. 17 is another example illustration of a dashboard screen that may provide information to aid in fault diagnosis.

FIG. 17 is another example of a dashboard that may be provided to report the type of information described herein. The left-most panel shows parameters in use at the time of the data collection. The central panel indicates the results of brain sensing between various electrode combinations using the displayed therapy parameters. In particular, the amplitude of the sensed LFP signal is measured, in microvolts, for stimulation delivered at various frequencies. Trend data is further provided for the various electrode combinations. This data may help determine if the expected baseline LFP signal is changing for one or more electrode combinations over time, which may help determine whether a fault is developing, and if so, where in the system that fault is likely to be occurring. On the lower portion of the central panel are patient goals, which provide symptom levels that are those set as goals for the patient's therapy. If the patient's symptoms are at, or below, these goals (as indicated by the dashed line for a particular symptom), good efficacy is being achieved. This goal information may be used to access whether efficacy is changing, as may be the case if a fault is developing or has developed within the system.

Figure 18:
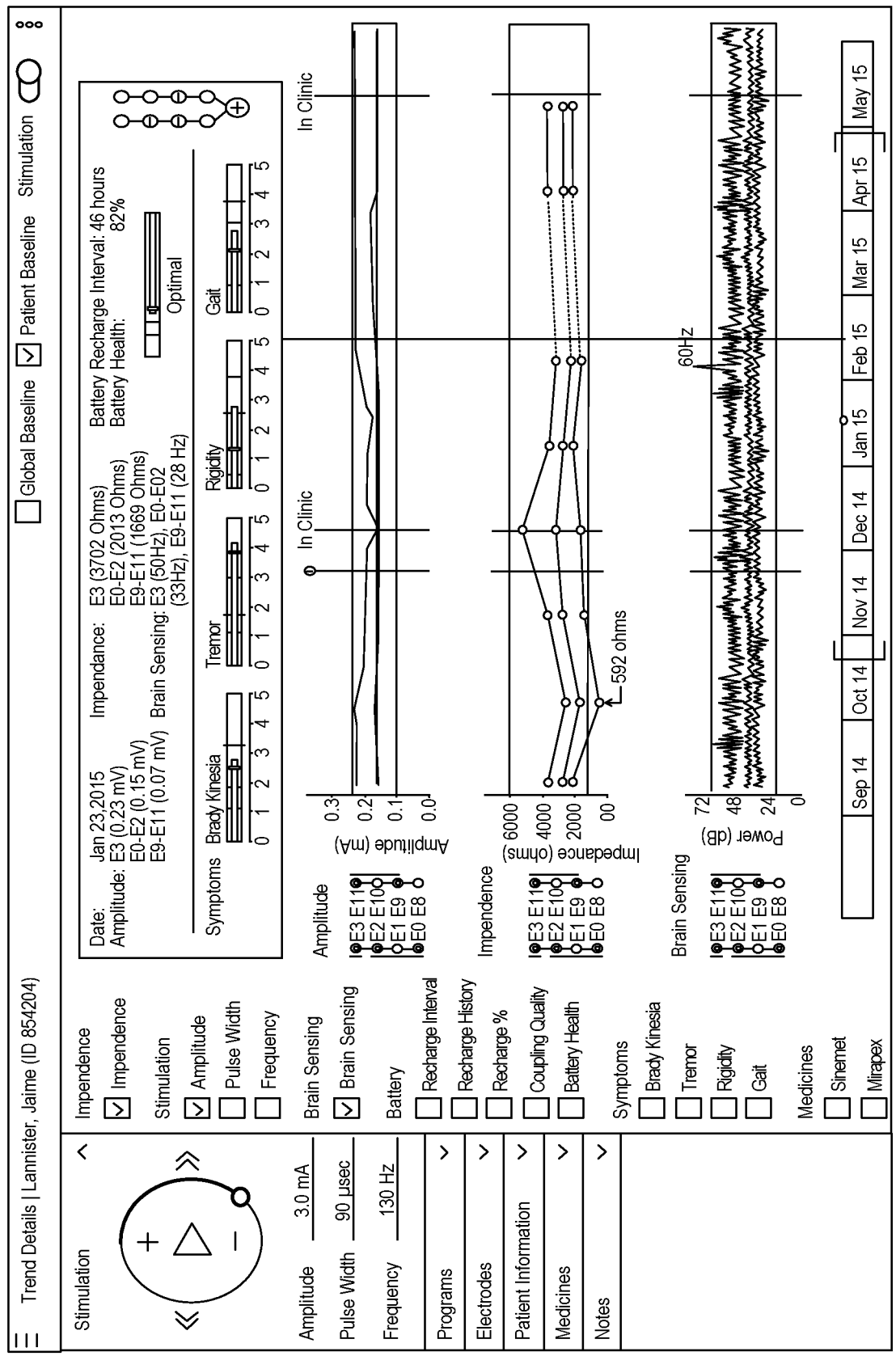
FIG. 18 is an illustration of another dashboard screen that provides information to aid in diagnosing system faults.

FIG. 18 is an illustration of yet another dashboard that provides stimulation parameters in use to deliver therapy along the left-hand side of the screen. The central panel provides summary information along the top. Below the summary information are changes in amplitude over time for the stimulation that is being used to deliver therapy to the patient. An impedance plot of impedance measured within the system between various electrode combinations is shown over the same period of time. Brain sensing information illustrates brain signals (typically expressed in microvolts and/or power (dB)) sensed between various electrode combinations over the same period of time. By plotting this information over a same period of time, a user may compare trends in impedance measurements, sensing data, and stimulation amplitude to determine whether a fault is developing in a given stimulation or sensing pathway.

Figure 19:
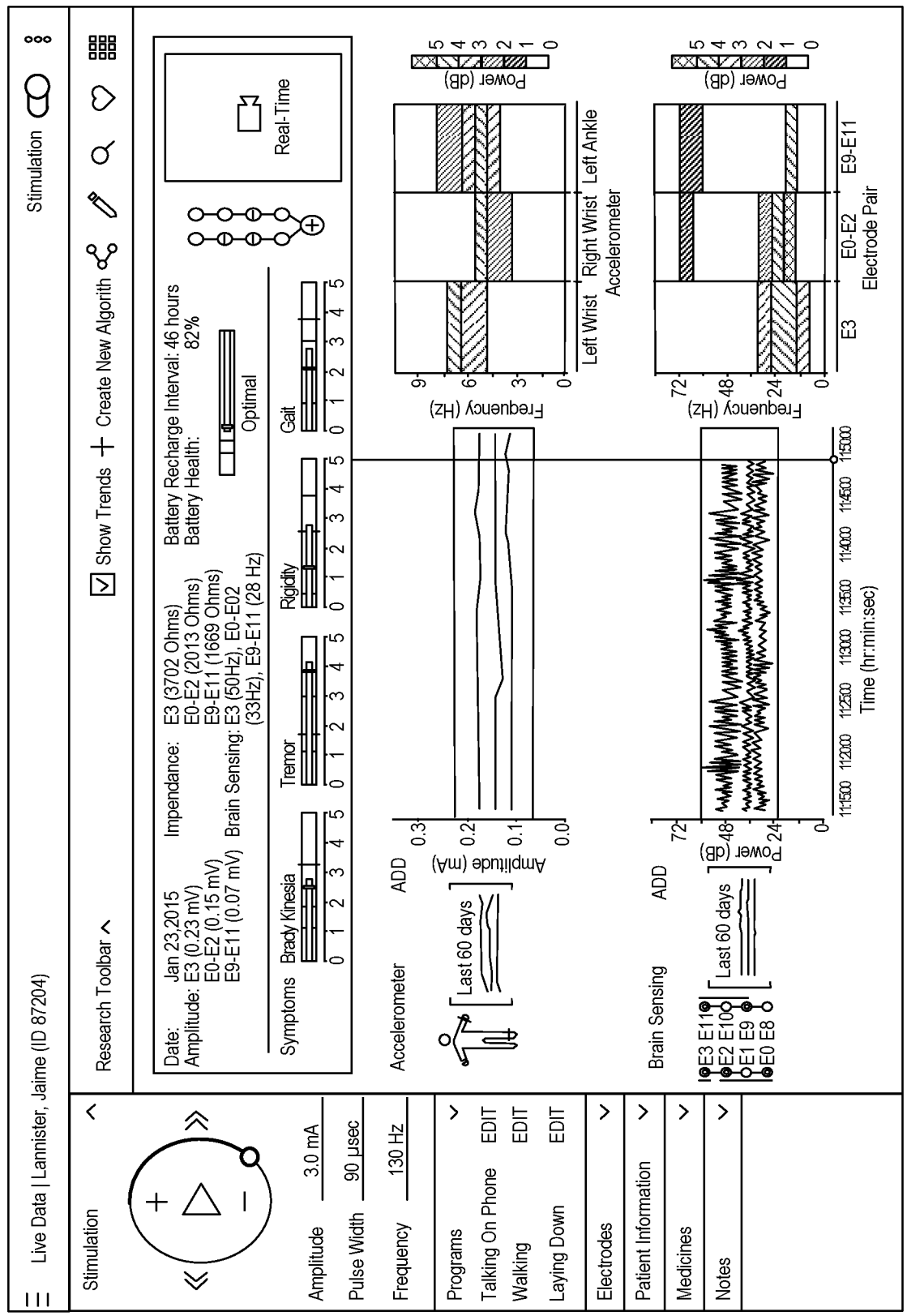
FIG. 19 is another example illustration of a dashboard screen that may be provided to help a user to determine if a system has a fault.

FIG. 19 is yet another example of a dashboard that may be provided to a patient to report a type of data discussed herein. The type of data shown in this diagram includes patient accelerometer data shown in the middle of the central panel. As discussed above, such data may be used to automatically or semi-automatically determine efficacy of therapy and trends associated with patient symptoms. The accelerometer data includes a plot of accelerometer readings obtained by accelerometers located at various points on the patient's body including the left wrist, right wrist, left ankle, and right ankle (shown along the bottom axis of the plot in the lower-right hand corner of the central panel.) This information is graphed against frequency content of the sensed signal shown along the y-axis.

The techniques described in this disclosure, including those attributed to programmer 14, IMD 16, or various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, image processing devices or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. While the techniques described herein are primarily described as being performed by processor 60 of IMD 16 and/or processor 80 of programmer 14, any one or more parts of the techniques described herein may be implemented by a processor of one of IMD 16, programmer 14, or another computing device, alone or in combination with each other. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed to support one or more aspects of the functionality described in this disclosure.

To reiterate, acutely-measured impedance data is currently the only available information regarding an implanted DBS system (device, lead and lead extension) and its interaction with the tissue. Impedance data have been used to detect hardware malfunctions such as breaks or shorts in the DBS system. Whereas, several researchers have reported detecting unusually low or high impedance values associated with verified hardware complications, others have reported detecting abnormal impedance values with no verifiable hardware problems or relatively normal impedance values despite verified hardware complications. In the latter set of cases, a loss of DBS therapy benefit may result from an undetected electrical shunt. There is a strong need to better identify and diagnose DBS system connection integrity issues for gauging the impact on therapy and suggest potential solutions.

In the embodiments set forth herein, a new concept is described in which indicators of compromised DBS leads (e.g. short circuits or electrical shunts) are derived, based on brain sensing from one or more DBS leads. DBS lead integrity is evaluated using an assessment technique involving a combination of: (1) impedance values, (2) evoked potential measurements (EPs), and, (3) identification of movement or ECG artifact detected in the sensed brain signals. A DBS lead is determined to be functioning or non-functioning based on an aggregate outcome of measures. The invention has an advantage over traditional methods, in that it can reveal hidden failures that are masked, which result in impedance values that appear normal despite the DBS lead integrity being compromised.

In one embodiment, epilepsy patients are implanted with DBS leads positioned within the anterior nucleus (therapy) and hippocampus (seizure zone). Impedance measurements of the AN and HC DBS leads are taken, and determined to be in or out of range. Two additional assessments, based on signal processing of LFP signals, are performed to further evaluate the lead and allow for a more refined and accurate assessment. According to some examples, first, a low frequency (e.g., 2-10 Hz) stimulation from the AN DBS therapy lead is conducted, and a determination is made to identify evoked potentials (EP) in LFP signals of the hippocampus. A further step involves comparing the observed EP (see FIG. 9A) to a reference EP (see FIG. 9B), which may be a representative EP (i.e., template, with no prior data) or a sample EP or series of EPs from the patient, which were collected when the lead was known to be functioning. An EP metric is shown in a system log.

According to some examples, second, LFP signals from the DBS leads are evaluated for movement or ECG artifact. Such artifacts will occur when the patient performs a motion task, that flexes the lead extension or lead body (including palpation at the IPG site). Motion or ECG artifacts may also be present via leakage pathways, due to breaks or incomplete sealing/insulation. The assessment for such artifacts in the brain signals may occur during the following INS system routines: montage sweep for guided programming; real-time streaming to assess signal quality; and, background recording during baseline and/or stimulation trials. An example is shown in FIG. 13, in which a movement artifact is observed during real-time streaming. A movement or ECG artifact metric is indicated in a system log. In FIG. 13, LFP recordings are collected during real-time streaming, from both the anterior nucleus (top) and hippocampus (bottom). Note the movement artifact in the top channel, which occurred when the subject intermittently moved its head.

A similar phenomenon has also been observed in other brain structures, including the sub-thalamic nucleus (see FIGS. 11A and 11B). Enabling sensing from the STN lead indicated the DBS lead had intermittent breaks in continuity, where these occurred during movement. In FIGS. 11A and 11B, there is a DBS STN lead with apparent intermittent leakage: As the subject moves its head, a break is created that impacts stimulation rejection. This occurred in DBS lead contact pairs with apparently normal impedances.

A non-functioning or compromised lead is indicated by observing or detecting (via automated template matching algorithms) a degraded evoked response, lack of an evoked response, or significant movement or ECG artifact. This can occur in the presence of impedance values that appear to be normal, which in isolation, would indicate the system is functioning properly. A consequence for this is that a patient would not be receiving stimulation therapy when intended. Lead integrity metrics are shown in a system log for each parameter set that is tested, and may be combined with additional biomarkers for therapy improvement.

The proposed paradigm represents a strategy in which layering occurs in "active monitoring". The montage sweep is passive, and either evoked potentials or a parameter sweep may prove useful as an algorithm for programming assistance. For example, a logical sequence first sweeps through frequencies, identifies one, then with that set sweeps through amplitudes, then looks for cycling opportunity. This could be used for epilepsy and maybe dystonia/MvD/memory.

These are summarized below:

Lead Failure Metrics:

Impedance summary (out of range R values or abnormal trending of R values indicating short or open circuit).

Evoked potentials in LFP signals (in the presence of out of range I values or abnormal trending of I values).

Movement ECG or other electrical artifact in LFP signals (in the presence of the abnormal I and/or R values above).

In some cases, a coincident change in therapeutic window (therapeutic benefits relative to side effect profile)

Safety Metrics:

Presence of after-discharge (AD) detected with stimulation; AD duration.

Automatic AD shut-off.

Therapy Effectiveness Metrics:

LFP suppression index; max suppression (% rms) and duration.

Evoked potential suppression; max suppression (peak amplitude change); area under curve.

After-discharge suppression; (peak and duration).

In a second embodiment, the hippocampal lead may be considered the "therapy lead", and as such, the assessments may be reversed. In a third embodiment, dual lead configurations for other therapeutic areas, including Parkinson's disease, may be used. For example, STN may be used as a therapy site, and motor cortex may be used as a recording site. In a fourth embodiment, single lead configurations may be assessed, with the invention using the DBS from the "other hemisphere" as a reference electrode.

Various examples have been described. These and other examples are within the scope of the following claims.

What is claimed is:

1. A system, comprising:
a sensor configured to sense a first signal at a first location of an anatomy of a patient, and
one or more processors configured to associate a portion of the first signal with a second signal introduced at a second location of the anatomy of the patient and to determine whether a fault exists in the system based on one or more characteristics of the associated portion of the first signal, wherein the second signal is stimulation delivered to the second location; and wherein the sensor is configured to sense a response to the stimulation delivered at the second location and wherein the first location is a hippocampus of the brain and the second location is an anterior nucleus.

2. The system of claim 1, wherein the sensor is an electrode and the first signal is a local field potential signal and is sensed in the brain of the patient.

3. The system of claim 1, wherein the sensor is an electrode, and wherein the system comprises a lead carrying the electrode, and wherein the one or more processors are configured to determine whether the fault exists in the lead.

4. The system of claim 1, wherein the one or more processors are configured to detect that one of a lead or a lead extension of the implantable medical device system is associated with a low impedance pathway based on one or more characteristics of the associated portion of the first signal.

5. The system of claim 1, wherein the stimulation delivered at the second location comprises stimulation delivered at a frequency range of between 2-10 Hz.

6. The system of claim 1, wherein the sensor is an implantable electrode configured to sense a local field potential (LFP) signal.

7. The system of claim 6, wherein the one or more processors are configured to:
determine whether the fault exists in the system based on one or more characteristics of the associated portion of the first signal by identifying an evoked response in the LFP signal and
compare the identified evoked response in the sensed LFP signal to one or more baseline evoked response signals.

8. The system of claim 7, further comprising a memory to store the one or more baseline evoked response signals.

9. The system of claim 1, wherein the second signal comprises an artifact resulting from beating of the patient's heart, and wherein the one or more processors are configured to determine whether the fault exists in the system based on one or more characteristics of the associated portion of the first signal by detecting one or more characteristics of the artifact in the sensed first signal.

10. The system of claim 9, wherein the artifact is an ECG artifact and the sensed first signal is a brain signal.

11. The system of claim 1, wherein the one or more processors are further configured to:
receive one or more values indicative of impedance associated with one or more components of the implantable medical device system; and
determine whether any of the received values are out of range;

and if any of the received values are out of range:
initiate sensing, via the sensor, of the first signal at the first location of the anatomy of a patient;
associate the portion of the first signal with a second signal introduced at a second location of the anatomy of the patient; and
determine whether the fault exists in the system based on one or more characteristics of the associated portion of the first signal.

12. A system, comprising:
a sensor configured to sense a first signal at a first location of an anatomy of a patient and
one or more processors configured to associate a portion of the first signal with a second signal introduced at a second location of the anatomy of the patient and to determine whether a fault exists in the system based on one or more characteristics of the associated portion of the first signal, wherein the second signal is stimulation delivered to the second location, wherein the sensor is configured to sense a response to the stimulation delivered at the second location, and wherein the first location is a location within a first hemisphere of the brain and the second location is a location within a second hemisphere of the brain.

13. A system, comprising:
a sensor configured to sense a first signal at a first location of an anatomy of a patient; and
one or more processors configured to associate a portion of the first signal with a second signal introduced at a second location of the anatomy of the patient and to determine whether a fault exists in the system based on one or more characteristics of the associated portion of the first signal, wherein the second signal is stimulation delivered to the second location, wherein the sensor is configured to sense a response to the stimulation delivered at the second location, and wherein the stimulation delivered at the second location comprises stimulation delivered at a frequency range of between 2-10 Hz.

14. A system, comprising:
a sensor configured to sense a first signal at a first location of an anatomy of a patient; and
one or more processors configured to associate a portion of the first signal with a second signal introduced at a second location of the anatomy of the patient and to determine whether a fault exists in the system based on one or more characteristics of the associated portion of the first signal, wherein the second signal is stimulation delivered to the second location, wherein the sensor is configured to sense a response to the stimulation delivered at the second location, wherein the sensor is an implantable electrode configured to sense a local field potential (LFP) signal, and wherein the one or more processors are configured to:
determine whether the fault exists in the system based on one or more characteristics of the associated portion of the first signal by identifying an evoked response in the LFP signal and
compare the identified evoked response in the sensed LFP signal to one or more baseline evoked response signals.

15. A system, comprising:
a sensor configured to sense a first signal at a first location of an anatomy of a patient; and
one or more processors configured to associate a portion of the first signal with a second signal introduced at a second location of the anatomy of the patient and to determine whether a fault exists in the system based on one or more characteristics of the associated portion of the first signal, wherein the second signal comprises an artifact resulting from beating of the patient's heart, and wherein the one or more processors are configured to determine whether the fault exists in the system based on one or more characteristics of the associated portion of the first signal by detecting one or more characteristics of the artifact in the sensed first signal.

16. A system, comprising:
a sensor configured to sense a first signal at a first location of an anatomy of a patient; and
one or more processors configured to associate a portion of the first signal with a second signal introduced at a second location of the anatomy of the patient and to determine whether a fault exists in the system based on one or more characteristics of the associated portion of the first signal, wherein the one or more processors are further configured to:
receive one or more values indicative of impedance associated with one or more components of the implantable medical device system; and
determine whether any of the received values are out of range;
and if any of the received values are out of range:
initiate sensing, via the sensor, of the first signal at the first location of the anatomy of a patient;
associate the portion of the first signal with a second signal introduced at a second location of the anatomy of the patient; and
determine whether the fault exists in the system based on one or more characteristics of the associated portion of the first signal.

17. A method of detecting a fault in an implantable medical device system, comprising:
sensing a first signal via an electrode at a first location of an anatomy of a patient,
at one or more processors, associating a portion of the first signal with a second signal introduced at a second location of the anatomy of the patient; and
at the one or more processors, determining whether a fault exists in the system based on one or more characteristics of the associated portion of the first signal, wherein one or more of associating a portion of the first signal with the second signal introduced at the second location in the anatomy of the patient and determining whether the fault exists in the system are performed by one or more processors, wherein the second signal is stimulation delivered to the second location; and wherein sensing, via an electrode at a first location of an anatomy of a patient, comprises sensing a response to the stimulation delivered at the second location and wherein the first location is a hippocampus of the brain and the second location is an anterior nucleus.

18. The method of claim 17, wherein the first signal is a local field potential signal.

19. The method of claim 17, wherein the first signal is a signal sensed from the brain of a patient.

20. The method of claim 17, wherein the fault is a fault in one or more of a lead or a lead extension of the implantable medical device system.

21. The method of claim 17, wherein determining whether a fault exists in the system based on one or more characteristics of the associated portion of the first signal comprises detecting that a lead of the implantable medical device system has a short circuit.

22. The method of claim 17, wherein the stimulation delivered at the second location comprises stimulation delivered at a frequency range of between 2-10 Hz.

23. The method of claim 17, wherein sensing a first signal via an electrode at a first location of an anatomy of the patient comprises sensing a local field potential (LFP) signal via the implantable electrode at the first location of the anatomy of the patient.

24. The method of claim 23, wherein determining whether a fault exists in the system based on one or more characteristics of the associated portion of the first signal comprises identifying an evoked response in the LFP signal and further comprising comparing the identified evoked response in the sensed LFP signal to one or more baseline evoked response signals.

25. The method of claim 24, wherein the one or more baseline evoked response signals are representative of evoked response signals that are obtained when it is known that a fault is not present in the system.

26. The method of claim 17, wherein the first location is a location within a first hemisphere of the brain and the second location is a location within a second hemisphere of the brain.

27. The method of claim 17, wherein the second signal comprises an artifact resulting from activity of the patient's heart, and wherein determining whether a fault exists in the system based on one or more characteristics of the associated portion of the first signal comprises detecting one or more characteristics of the artifact in the sensed first signal.

28. The method of claim 27, wherein the artifact is an ECG artifact and the sensed first signal is a brain signal.

29. The method of claim 17, wherein the second signal comprises a movement artifact and wherein determining whether a fault exists in the system based on one or more characteristics of the associated portion of the first signal comprises detecting one or more characteristics of the movement artifact in the sensed first signal.

30. The method of claim 29, wherein the first signal is a brain signal.

31. The method of claim 17, further comprising:
  determining whether one or more impedance values within the implantable medical device system are out of range; and
  if one or more impedance values within the implantable medical device system are out of range, initiating the sensing of the first signal via the electrode at the first location of the anatomy of a patient, the associating of the portion of the first signal with the second signal introduced at the second location of the anatomy of the patient and the determining whether the fault exists in the system based on one or more characteristics of the associated portion of the first signal.

* * * * *